US008334468B2

(12) United States Patent
Palmer et al.

(10) Patent No.: US 8,334,468 B2
(45) Date of Patent: *Dec. 18, 2012

(54) METHOD OF SWITCHING A CORDLESS HAND-HELD ULTRASONIC CAUTERY CUTTING DEVICE

(75) Inventors: Matthew A. Palmer, Miami, FL (US); Kevin W. Smith, Coral Gables, FL (US); Thomas O. Bales, Jr., Coral Gables, FL (US); Derek Dee Deville, Coral Gables, FL (US)

(73) Assignee: Covidien AG (CH)

(*) Notice: Subject to any disclaimer, the term of this patent is extended or adjusted under 35 U.S.C. 154(b) by 110 days.

This patent is subject to a terminal disclaimer.

(21) Appl. No.: 12/868,545

(22) Filed: Aug. 25, 2010

(65) Prior Publication Data
US 2011/0009890 A1    Jan. 13, 2011

Related U.S. Application Data

(60) Division of application No. 12/868,505, filed on Aug. 25, 2010, and a continuation-in-part of application No. 12/547,898, filed on Aug. 26, 2009, now Pat. No. 8,061,014, and a continuation-in-part of application No. 12/547,975, filed on Aug. 26, 2009, and a continuation-in-part of application No. 12/547,999, filed on Aug. 26, 2009.

(60) Provisional application No. 61/236,934, filed on Aug. 26, 2009.

(51) Int. Cl.
*H01H 9/00* (2006.01)
(52) U.S. Cl. ........................................ 200/1 B
(58) Field of Classification Search .................. 200/1 B, 200/1 R, 19.01, 5 R, 5 A, 42.01, 43.17; 227/19, 227/176.1, 175.1, 175.2, 180.1, 179.1; 606/169, 606/139, 219; 600/437, 461, 471; 601/2; 604/22; 433/86, 119; 173/29, 217, 2; 483/16, 483/901; 29/594, 831, 832, 854
See application file for complete search history.

(56) References Cited

U.S. PATENT DOCUMENTS

| 1,813,902 A | 7/1931 | Bovie |
|---|---|---|
| 2,874,470 A | 2/1959 | Richards |
| 2,990,616 A | 7/1961 | Arthur |
| 3,432,691 A | 3/1969 | Shoh |

(Continued)

FOREIGN PATENT DOCUMENTS
EP    0 705 570    4/1996
(Continued)

OTHER PUBLICATIONS

Surgicon, Inc. SpringLock and SpringLock Remover Launch Presentation Materials, Revised Jan. 23, 2002.

(Continued)

*Primary Examiner* — Edwin A. Leon

(57) ABSTRACT

A method for operating an ultrasonic, self-powered surgical device, includes the steps of connecting a self-contained power supply to a surgical device handle, providing a control circuit within at least one of the handle and the power supply, the control circuit being operable to carry out at least two operational conditions of the surgical device, and effecting the at least two operational conditions with a two-stage switch electrically connected to the control circuit, a first stage of the switch effecting a first of the at least two operational conditions and a second stage of the switch effecting a second of the at least two operational conditions different from the first operational condition.

18 Claims, 31 Drawing Sheets

U.S. PATENT DOCUMENTS

| | | | |
|---|---|---|---|
| 3,489,930 A | 1/1970 | Shoh |
| 3,629,726 A | 12/1971 | Popescu |
| 3,668,486 A | 6/1972 | Silver |
| 3,809,977 A | 5/1974 | Balamuth et al. |
| 3,875,945 A | 4/1975 | Friedman |
| 3,924,335 A | 12/1975 | Balamuth et al. |
| 4,012,647 A | 3/1977 | Balamuth et al. |
| 4,300,083 A | 11/1981 | Heiges |
| 4,302,728 A | 11/1981 | Nakamura |
| 4,641,053 A | 2/1987 | Takeda |
| 5,264,925 A | 11/1993 | Shipp |
| 5,275,166 A | 1/1994 | Vaitekunas |
| 5,374,813 A | 12/1994 | Shipp |
| 5,394,187 A | 2/1995 | Shipp |
| 5,408,268 A | 4/1995 | Shipp |
| 5,451,220 A | 9/1995 | Ciervo |
| 5,490,860 A | 2/1996 | Middle et al. |
| 5,593,414 A | 1/1997 | Shipp et al. |
| 5,717,306 A | 2/1998 | Shipp |
| 5,728,130 A | 3/1998 | Ishikawa et al. |
| 5,792,138 A | 8/1998 | Shipp |
| 5,810,859 A | 9/1998 | DiMatteo et al. |
| 5,858,018 A | 1/1999 | Shipp et al. |
| 5,873,873 A | 2/1999 | Smith |
| 5,938,633 A | 8/1999 | Beaupre |
| 5,944,737 A | 8/1999 | Tsonton |
| 5,947,984 A | 9/1999 | Whipple |
| 5,954,736 A | 9/1999 | Bishop et al. |
| 5,993,465 A | 11/1999 | Shipp et al. |
| 5,994,855 A | 11/1999 | Lundell et al. |
| 6,031,526 A | 2/2000 | Shipp |
| 6,036,667 A | 3/2000 | Manna et al. |
| 6,068,647 A | 5/2000 | Witt |
| 6,162,194 A | 12/2000 | Shipp |
| 6,183,426 B1 | 2/2001 | Saida et al. |
| 6,254,623 B1 | 7/2001 | Haibel, Jr. et al. |
| 6,257,241 B1 | 7/2001 | Wampler |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler |
| 6,290,575 B1 | 9/2001 | Shipp |
| 6,306,157 B1 | 10/2001 | Shchervinsky |
| 6,309,400 B2 | 10/2001 | Beaupre |
| 6,325,811 B1 | 12/2001 | Messerly |
| 6,328,751 B1 | 12/2001 | Beaupre |
| 6,350,269 B1 | 2/2002 | Shipp et al. |
| 6,352,532 B1 | 3/2002 | Kramer |
| 6,416,486 B1 | 7/2002 | Wampler |
| 6,423,082 B1 | 7/2002 | Houser et al. |
| 6,432,118 B1 | 8/2002 | Messerly |
| 6,443,968 B1 | 9/2002 | Holthaus |
| 6,449,006 B1 | 9/2002 | Shipp |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,491,708 B2 | 12/2002 | Madan |
| 6,500,188 B2 | 12/2002 | Harper |
| 6,514,267 B2 | 2/2003 | Jewett |
| 6,537,291 B2 | 3/2003 | Friedman |
| 6,561,983 B2 | 5/2003 | Cronin et al. |
| 6,588,277 B2 | 7/2003 | Giordano |
| 6,589,200 B1 | 7/2003 | Schwemberger |
| 6,607,540 B1 | 8/2003 | Shipp |
| 6,623,500 B1 | 9/2003 | Cook et al. |
| 6,626,926 B2 | 9/2003 | Friedman et al. |
| 6,633,234 B2 | 10/2003 | Wiener et al. |
| 6,652,539 B2 | 11/2003 | Shipp et al. |
| 6,652,545 B2 | 11/2003 | Shipp et al. |
| 6,660,017 B2 | 12/2003 | Beaupre |
| 6,662,127 B2 | 12/2003 | Wiener et al. |
| 6,666,875 B1 | 12/2003 | Sakurai et al. |
| 6,678,621 B2 | 1/2004 | Wiener et al. |
| 6,679,899 B2 | 1/2004 | Wiener |
| 6,719,776 B2 | 4/2004 | Baxter |
| 6,752,815 B2 | 6/2004 | Beaupre |
| 6,773,444 B2 | 8/2004 | Messerly |
| 6,869,439 B2 | 3/2005 | White et al. |
| 6,908,472 B2 | 6/2005 | Wiener et al. |
| 6,915,623 B2 | 7/2005 | Dey et al. |
| 6,945,981 B2 | 9/2005 | Donofrio et al. |
| 6,976,969 B2 | 12/2005 | Messerly |
| 7,037,306 B2 | 5/2006 | Podany |
| 7,066,895 B2 | 6/2006 | Podany |
| 7,074,218 B2 | 7/2006 | Washington et al. |
| 7,108,695 B2 | 9/2006 | Witt et al. |
| 7,128,720 B2 | 10/2006 | Podany |
| 7,135,030 B2 | 11/2006 | Schwemberger |
| 7,163,548 B2 | 1/2007 | Stulen et al. |
| 7,179,254 B2 | 2/2007 | Pendekanti |
| 7,179,271 B2 | 2/2007 | Friedman et al. |
| 7,207,997 B2 | 4/2007 | Shipp et al. |
| 7,217,128 B2 | 5/2007 | Atkin et al. |
| 7,244,262 B2 | 7/2007 | Wiener |
| 7,269,873 B2 | 9/2007 | Brewer et al. |
| 7,273,483 B2 | 9/2007 | Wiener et al. |
| 7,300,446 B2 | 11/2007 | Beaupre |
| 7,335,997 B2 | 2/2008 | Wiener |
| 7,337,010 B2 | 2/2008 | Howard et al. |
| 2003/0144680 A1 | 7/2003 | Kellogg et al. |
| 2003/0199794 A1 | 10/2003 | Sakurai |
| 2003/0212363 A1 | 11/2003 | Shipp |
| 2004/0097972 A1 | 5/2004 | Shipp et al. |
| 2004/0116952 A1* | 6/2004 | Sakurai et al. ............ 606/169 |
| 2005/0119677 A1 | 6/2005 | Shipp |
| 2005/0149063 A1 | 7/2005 | Young et al. |
| 2005/0234338 A1 | 10/2005 | Masuda |
| 2005/0234484 A1 | 10/2005 | Houser et al. |
| 2006/0058825 A1 | 3/2006 | Ogura et al. |
| 2006/0087286 A1 | 4/2006 | Phillips |
| 2006/0129168 A1 | 6/2006 | Shipp |
| 2006/0178667 A1 | 8/2006 | Sartor |
| 2006/0194567 A1 | 8/2006 | Kelly |
| 2006/0206100 A1 | 9/2006 | Eskridge |
| 2006/0217729 A1 | 9/2006 | Eskridge et al. |
| 2007/0149881 A1 | 6/2007 | Rabin |
| 2007/0166663 A1 | 7/2007 | Telles et al. |
| 2007/0175960 A1 | 8/2007 | Shelton, IV et al. |
| 2007/0239028 A1 | 10/2007 | Houser et al. |
| 2007/0239101 A1 | 10/2007 | Kellogg |
| 2008/0051693 A1 | 2/2008 | Babaev |
| 2008/0200940 A1* | 8/2008 | Eichmann et al. ............ 606/169 |
| 2008/0245841 A1 | 10/2008 | Smith |
| 2009/0118751 A1* | 5/2009 | Wiener et al. ............ 606/169 |
| 2009/0143805 A1 | 6/2009 | Palmer |
| 2009/0223033 A1 | 9/2009 | Houser |

FOREIGN PATENT DOCUMENTS

| | | |
|---|---|---|
| EP | 0 908 148 | 4/1999 |
| EP | 1 594 209 | 11/2005 |
| EP | 1 707 131 | 10/2006 |
| EP | 2 200 145 | 6/2010 |
| WO | 2006/119376 | 11/2006 |
| WO | 2007/047380 | 4/2007 |

OTHER PUBLICATIONS

European Search Report of European App. No. 08858351.3.
European Search Report of European App. No. 11010043.5.
European Search Report of European App. No. 11010007.0.
European Search Report of European Patent App. No. 12164202.9 dated Aug. 7, 2012.

* cited by examiner

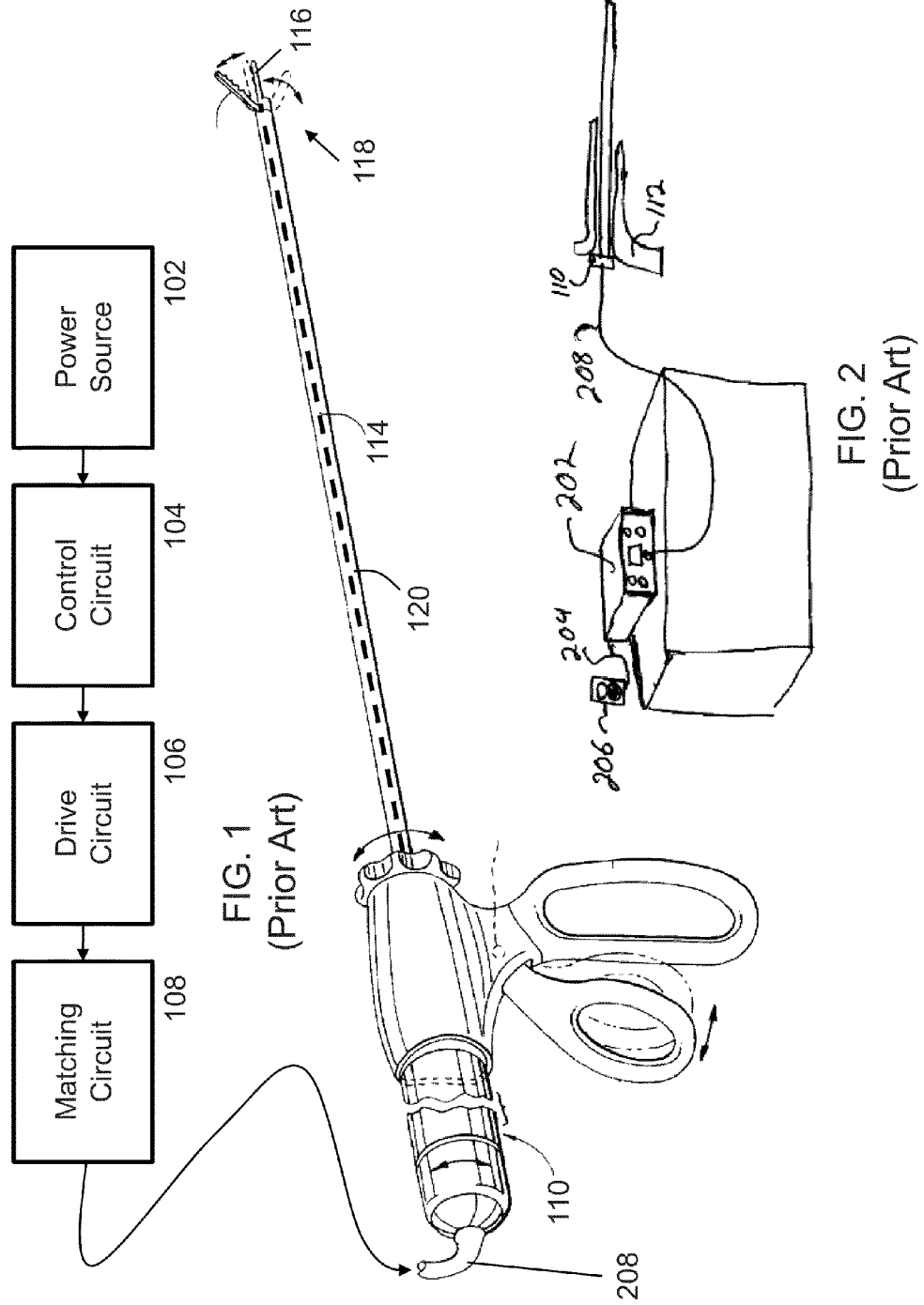

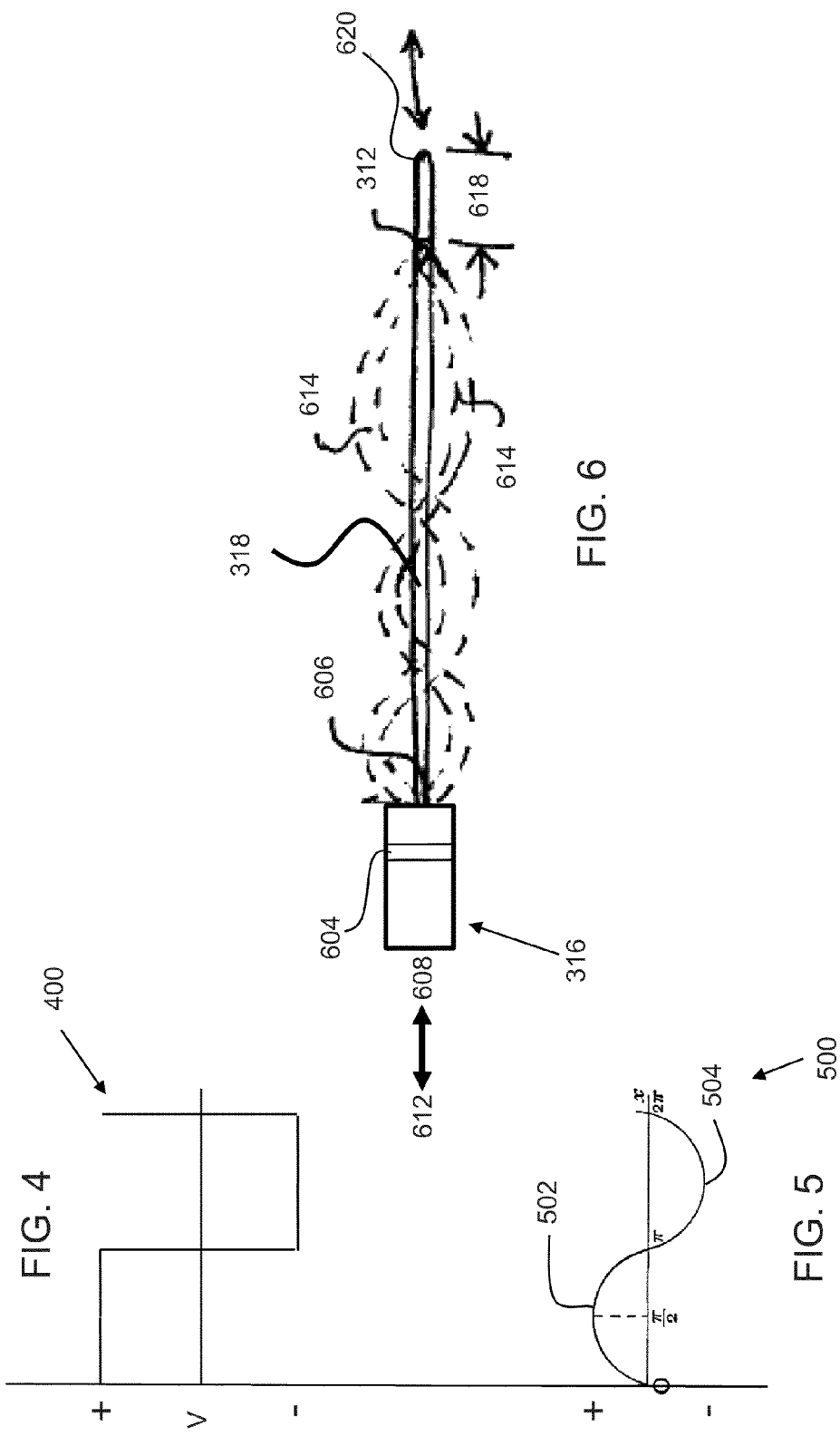

METHOD OF SWITCHING A CORDLESS HAND-HELD ULTRASONIC CAUTERY CUTTING DEVICE

CROSS-REFERENCE TO RELATED APPLICATIONS

This application:
claims the priority, under 35 U.S.C. §119, of U.S. Provisional Patent Application Ser. No. 61/236,934, filed on Aug. 26, 2009; and
is a divisional of U.S. patent application Ser. No. 12/868,505, filed Aug. 25, 2010; and
is a continuation-in-part of:
U.S. patent application Ser. No. 12/547,898, filed on Aug. 26, 2009;
U.S. patent application Ser. No. 12/547,975, filed on Aug. 26, 2009; and
U.S. patent application Ser. No. 12/547,999, filed on Aug. 26, 2009,
each of these three applications being divisional applications of the other and each being a continuation-in-part of U.S. patent application Ser. Nos. 12/266,101 filed on Nov. 6, 2008; 12/266,146 filed on Nov. 6, 2008; 12/266,226 filed on Nov. 6, 2008; 12/266,252 filed on Nov. 6, 2008; 12/266,320 filed on Nov. 6, 2008; 12/266,664 filed on Nov. 7, 2008; 12/269,544 filed on Nov. 12, 2008; 12/269,629 filed on Nov. 12, 2008; and 12/270,146 filed on Nov. 13, 2008,
the entire disclosures of which are all hereby incorporated herein by reference in their entireties.

BACKGROUND OF THE INVENTION

1. Field of the Invention

The present invention relates generally to an ultrasonic cutting device and, more particularly, relates to a method of switching a cordless, hand-held, fully electrically powered and controlled, surgical ultrasonic cutting device.

2. Description of the Related Art

Ultrasonic instruments are effectively used in the treatment of many medical conditions, such as removal of tissue and cauterization of vessels. Cutting instruments that utilize ultrasonic waves generate vibrations with an ultrasonic transducer along a longitudinal axis of a cutting blade. By placing a resonant wave along the length of the blade, high-speed longitudinal mechanical movement is produced at the end of the blade. These instruments are advantageous because the mechanical vibrations transmitted to the end of the blade are very effective at cutting organic tissue and, simultaneously, coagulate the tissue using the heat energy produced by the ultrasonic frequencies. Such instruments are particularly well suited for use in minimally invasive procedures, such as endoscopic or laparoscopic procedures, where the blade is passed through a trocar to reach the surgical site.

For each kind of cutting blade (e.g., length, material, size), there are one or more (periodic) driving signals that produce a resonance along the length of the blade. Resonance results in optimal movement of the blade tip and, therefore, optimal performance during surgical procedures. However, producing an effective cutting-blade driving signal is not a trivial task. For instance, the frequency, current, and voltage applied to the cutting tool must all be controlled dynamically, as these parameters change with the varying load placed on the blade and with temperature differentials that result from use of the tool.

FIG. 1 shows a block schematic diagram of a prior-art circuit used for applying ultrasonic mechanical movements to an end effector. The circuit includes a power source 102, a control circuit 104, a drive circuit 106, a matching circuit 108, a transducer 110, and also includes a handpiece 112, and a waveguide 114 secured to the handpiece 112 (diagrammatically illustrated by a dashed line) and supported by a cannula 120. The waveguide 114 terminates to a blade 116 at a distal end. A clamping mechanism, referred to as an "end effector" 118, exposes and enables the blade portion 116 of the waveguide 114 to make contact with tissue and other substances. Commonly, the end effector 118 is a pivoting arm that acts to grasp or clamp onto tissue between the arm and the blade 116. However, in some devices, the end effector 118 is not present.

The drive circuit 104 produces a high-voltage self-oscillating signal. The high-voltage output of the drive circuit 104 is fed to the matching circuit 108, which contains signal-smoothing components that, in turn, produce a driving signal (wave) that is fed to the transducer 110. The oscillating input to the transducer 110 causes the mechanical portion of the transducer 110 to move back and forth at a magnitude and frequency that sets up a resonance along the waveguide 114. For optimal resonance and longevity of the resonating instrument and its components, the driving signal applied to the transducer 110 should be as smooth a sine wave as can practically be achieved. For this reason, the matching circuit 108, the transducer 110, and the waveguide 114 are selected to work in conjunction with one another and are all frequency sensitive with and to each other.

Because a relatively high-voltage (e.g., 100 V or more) is required to drive a typical piezoelectric transducer 110, the power source that is available and is used in all prior-art ultrasonic cutting devices is an electric mains (e.g., a wall outlet) of, typically, up to 15 A, 120 VAC. Therefore, all known ultrasonic cutting devices resemble that shown in FIGS. 1 and 2 and utilize a countertop box 202 with an electrical cord 204 to be plugged into the electrical mains 206 for supply of power. Resonance is maintained by a phase locked loop (PLL), which creates a closed loop between the output of the matching circuit 108 and the drive circuit 106. For this reason, in prior art devices, the countertop box 202 always has contained all of the drive and control electronics 104, 106 and the matching circuit(s) 108. A typical retail price for such boxes is in the tens of thousands of dollars.

A supply cord 208 delivers a sinusoidal waveform from the box 202 to the transducer 110 within the handpiece 112 and, thereby, to the waveguide 114. The prior art devices present a great disadvantage because the cord 208 has a length, size, and weight that restricts the mobility of the operator. The cord 208 creates a tether for the operator and presents an obstacle for the operator and those around him/her during any surgical procedure using the handpiece 112. In addition, the cord must be shielded and durable and is very expensive.

Another disadvantage exists in the prior art due to the frequency sensitivity of the matching circuit 108, the transducer 110, and the waveguide 114. By having a phase-locked-loop feedback circuit between the output of the matching circuit 108 and the drive circuit 104, the matching circuit 108 is required always to be located in the box 202, near the drive circuit 108, and separated from the transducer 110 by the length of the supply cord 208. This architecture introduces transmission losses and electrical parasitics, which are common products of ultrasonic-frequency transmissions.

In addition, prior-art devices attempt to maintain resonance at varying waveguide 114 load conditions by monitoring and maintaining a constant current applied to the transducer.

However, the only predictable relationship between current applied to the transducer 110 and amplitude is at resonance. Therefore, with constant current, the amplitude of the wave along the waveguide 114 is not constant across all frequencies. When prior art devices are under load, therefore, operation of the waveguide 114 is not guaranteed to be at resonance and, because only the current is being monitored and held constant, the amount of movement on the waveguide 114 can vary greatly. For this reason, maintaining constant current is not an effective way of maintaining a constant movement of the waveguide 114.

Furthermore, in the prior art, handpieces 112 and transducers 110 are replaced after a finite number of uses, but the box 202, which is vastly more expensive than the handpiece 112, is not replaced. As such, introduction of new, replacement handpieces 112 and transducers 110 frequently causes a mismatch between the frequency-sensitive components (108, 110, and 112), thereby disadvantageously altering the frequency introduced to the waveguide 114. The only way to avoid such mismatches is for the prior-art circuits to restrict themselves to precise frequencies. This precision brings with it a significant increase in cost.

Some devices claim to be able to contain all necessary components for ultrasonic procedures within a single handle. These devices, however, do not currently appear in the marketplace and the written descriptions of each disclose virtually no details of how their circuitry is enabled. At least one such device is described as being completely sealed and all of the device's electronic components, such as the power supply and the transducer, are non-replaceable. This design is self-evident, because the tool, used in surgery, must be sterilizable. However, in some surgeries, a cutting tool reaches its maximum lifespan within very few surgeries or, in some cases, even before the surgery is finished. With a sealed device design, the entire device must be disposed, including its expensive internal components.

In addition, this device is described as using inductive charging. It was not designed or envisioned to use modern, long-lasting, high-power batteries, such as lithium-ion (Li) batteries. As is known in the art, Lithium batteries cannot be charged in a series configuration of multiple cells. This is because, as the voltage increases in a particular cell, it begins to accept charging energy faster than the other lower-voltage cells. Therefore, each cell must be monitored so that a charge to that cell can be controlled individually. When a Lithium battery is formed from a group of cells, a multitude of wires extending from the exterior of the device to the battery is needed. Sakurai cannot provide this necessary feature because, by design, the sealed autoclavable Sakurai device does not and cannot have a plurality of external exposed contacts to be coupled to a charging device. In fact, the inductive charging feature for the sealed device is entirely at odds with exposed contacts.

Some electronic surgical devices have been manufactured with two or more separate switches and corresponding buttons that move the device from a first power level to a second power level. These two-switch devices require the operator to differentiate between the low-power switch and the higher-power switch. This requirement for differentiation leads to either the operator having to visually look at the device, most often to a portion of the device that is not easily visible from the operator's current view, or to leads to mistakes, which, during surgery, can be devastating.

Therefore, a need exists to overcome the problems associated with the prior art, for example, those discussed above.

SUMMARY OF THE INVENTION

Briefly, in accordance with exemplary embodiments of the present invention, a method of switching a cordless handheld apparatus that is capable of performing continuous ultrasonic cutting and cauterizing is disclosed. The invention includes a power supply, a control circuit, a drive circuit, and a matching circuit—all located within a handpiece of the ultrasonic cutting device and all operating and generating waveforms at battery voltages. Advantageously, the invention allows components to be replaced or moved between different devices.

The present invention, according to several embodiments, allows components of the device to be removed, replaced, serviced, and/or interchanged. Some components are "disposable," which, as used herein, means that the component is used for only one procedure and is then discarded. Still other components are "reusable," which, as used herein, means that the component can be aseptically cleaned and then used for at least a second time. As will be explained, other components are provided with intelligence that allows them to recognize the device to which they are attached and to alter their function or performance depending on several factors.

The invention provides a method of switching a cordless hand-held ultrasonic cautery cutting device that overcomes the hereinafore-mentioned disadvantages of the heretofore-known devices and methods of this general type and that require disposal of and prevent advantageous reuse of costly components.

With the foregoing and other objects in view, there is provided, in accordance with the invention, a method for operating an ultrasonic, self-powered surgical device, including the steps of connecting a self-contained power supply to a surgical device handle, providing a control circuit within at least one of the handle and the power supply, the control circuit being operable to carry out at least two operational conditions of the surgical device, and effecting the at least two operational conditions with a two-stage switch electrically connected to the control circuit, a first stage of the switch effecting a first of the at least two operational conditions and a second stage of the switch effecting a second of the at least two operational conditions different from the first operational condition.

In accordance with another mode of the invention, the control circuit controls an amount of power delivered from the power supply.

In accordance with a further mode of the invention, the first operational condition is a first amount of power delivered from the power supply and the second operational condition is a second amount of power delivered from the power supply.

In accordance with an added mode of the invention, a first amount of power is delivered from the power supply in the first operational condition and a second amount of power different from the first amount is delivered from the power supply in the second operational condition.

In accordance with an additional mode of the invention, the first amount of power is less than the second amount.

In accordance with yet another mode of the invention, the first and second operational conditions are effected using at least one electrical contact of the two-stage switch to electrically close the control circuit.

In accordance with yet a further mode of the invention, the first and second operational conditions are effected using at least one electrical contact of the two-stage switch to electrically break the control circuit.

In accordance with yet an added mode of the invention, changing a position of the two-stage switch switches between the first and second stages.

In accordance with yet an additional mode of the invention, the two-stage switch is in the first stage when in a first position and in the second stage when in a second position.

In accordance with again another mode of the invention, the first and second positions are operably connected in a stacked configuration.

In accordance with again a further mode of the invention, partially depressing the two-stage switch switches to the first stage and fully depressing the two-stage switch switches to the second stage.

In accordance with again an added mode of the invention, a plunger is coupled to the two-stage switch and applying pressure to the plunger changes the position of the two-stage switch. The plunger is spring-biased.

In accordance with again an additional mode of the invention, a variable amount of pressure is applied to the plunger to cause the two-stage switch to change position.

In accordance with still another mode of the invention, an amount of pressure needed to position the two-stage switch in the first stage is less than the amount of pressure needed to position the two-stage switch in the second stage.

In accordance with a concomitant mode of the invention, the two-stage switch is comprised of at least a first sub-switch and a second sub-switch, the first sub-switch effecting the first operational condition and the second sub-switch effecting the second operational condition.

Although the invention is illustrated and described herein as embodied in a method of switching a cordless hand-held ultrasonic cautery cutting device, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

While the specification concludes with claims defining the features of the invention that are regarded as novel, it is believed that the invention will be better understood from a consideration of the following description in conjunction with the drawing figures, in which like reference numerals are carried forward. Accordingly, the apparatus components and method steps have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

DETAILED DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIG. 1 is a diagrammatic illustration of components of a prior-art ultrasonic cutting device with separate power, control, drive and matching components in block diagram form.

FIG. 2 is a diagram illustrating the prior-art ultrasonic cutting device of FIG. 1.

FIG. 4 is graph illustrating a square waveform input to the matching circuit in accordance with an exemplary embodiment of the present invention.

FIG. 5 is graph illustrating a sinusoidal waveform output from the matching circuit in accordance with an exemplary embodiment of the present invention.

FIG. 6 is a diagrammatic illustration of the effect that a resonant sine wave input to a transducer has on a waveguide of the ultrasonic cutting device in accordance with an exemplary embodiment of the present invention with the sinusoidal pattern shown representing the amplitude of axial motion along the length of the waveguide.

DETAILED DESCRIPTION OF THE EMBODIMENTS

Figure 3:
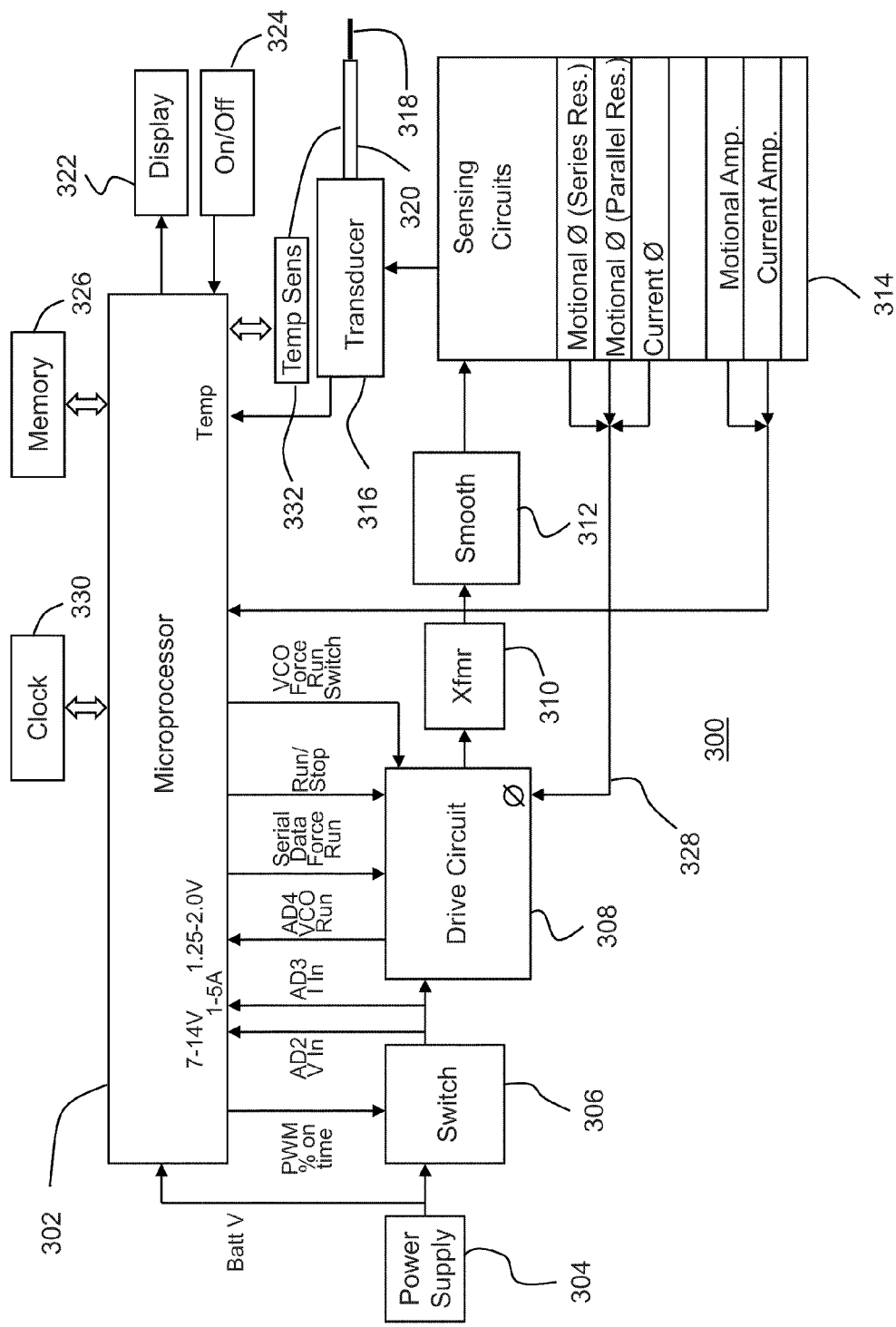
FIG. 3 is a block circuit diagram of an ultrasonic cutting device in accordance with an exemplary embodiment of the present invention.

It is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. Further, the terms and phrases used herein are not intended to be limiting; but rather, to provide an understandable description of the invention.

Before the present invention is disclosed and described, it is to be understood that the terminology used herein is for the purpose of describing particular embodiments only and is not intended to be limiting. In this document, the terms "a" or "an", as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. Relational terms such as first and second, top and bottom, and the like may be used solely to distinguish one entity or action from another entity or action without necessarily requiring or implying any actual such relationship or order between such entities or actions. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the object being described.

It will be appreciated that embodiments of the invention described herein may be comprised of one or more conventional processors and unique stored program instructions that control the one or more processors to implement, in conjunction with certain non-processor circuits and other elements, some, most, or all of the functions of ultrasonic cutting devices described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could also be used. Thus, methods and means for these functions have been described herein.

The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

The present invention, according to one embodiment, overcomes problems with the prior art by providing a lightweight, hand-holdable, ultrasonic cutting device that is powered by and controlled with components that fit entirely within a handle of the device. The hand-held device allows a surgeon to perform ultrasonic cutting and/or cauterizing in any surgical procedure without the need for external power and, particularly, without the presence of cords tethering the surgeon to a stationary object and constricting the ability of the surgeon while performing the surgical procedure.

Ultrasonic Surgical Device

Described now is an exemplary apparatus according to one embodiment of the present invention. Referring to FIG. 3, a block circuit diagram shows the invention 300, which includes a microprocessor 302, a clock 330, a memory 326, a power supply 304 (e.g., a battery), a switch 306 (e.g., a MOSFET power switch), a drive circuit 308 (PLL), a transformer 310, a signal smoothing circuit 312 (also referred to as a matching circuit and can be, e.g., a tank circuit), a sensing circuit 314, a transducer 316, and a waveguide, which terminates into an ultrasonic cutting blade 318, referred to herein simply as the waveguide 318. The invention also includes a cannula 320 for covering and supporting the waveguide 318. As used herein, the "waveguide-movement-generation assembly" is a sub-assembly including at least the transducer 316, but can also include other components, such as the drive circuit 308 (PLL), transformer 310, signal smoothing circuit 312, and/or the sensing circuit 314.

Ultrasonic cutting blades and waveguides are known in the art. The present invention's ability to provide all of the necessary components of an ultrasonic cutting tool in a hand-held package provides a great advantage over prior-art devices, which house a majority of the device components within a very expensive and heavy desktop box 202, as shown in FIG. 2, and create an expensive and bulky tether 208 between the device's handpiece 112 and the box 202.

One feature of the present invention that severs the dependency on high voltage (120 VAC) input power (a characteristic of all prior-art ultrasonic cutting devices) is the utilization of low-voltage switching throughout the wave-forming process and amplification of the driving signal only directly before the transformer stage. For this reason, in one exemplary embodiment of the present invention, power is derived from only a battery, or a group of batteries, small enough to fit either within the handpiece 112 or within a small box that attaches to the user, for example, at a waistband. State-of-the-art battery technology provides powerful batteries of a few centimeters in height and width and a few millimeters in depth. By combining the features of the present invention to provide an entirely self-contained and self-powered ultrasonic device, the capital outlay of the countertop box 202 is eliminated—resulting in almost a ten-fold reduction of manufacturing cost.

The output of the battery 304 is fed to and powers the processor 302. The processor 302 receives and outputs signals and, as will be described below, functions according to custom logic or in accordance with computer programs that are executed by the processor 302. The device 300 can also include a main memory 326, preferably, random access memory (RAM), that stores computer-readable instructions and data.

The output of the battery 304 also goes to a switch 306 that has a duty cycle controlled by the processor 302. By controlling the on-time for the switch 306, the processor 302 is able to dictate the total amount of power that is ultimately delivered to the transducer 316. In one embodiment, the switch 306 is an electrically controlled metal-oxide-semiconductor field-effect transistor (MOSFET), although other switches and switching configurations are adaptable as well. The output of the switch 306 is fed to a drive circuit 308 that contains, for example, a phase detecting PLL and/or a low-pass filter and/or a voltage-controlled oscillator. The output of the switch 306 is sampled by the processor 302 to determine the voltage and current of the output signal (referred to in FIG. 3 respectively as AD2 V In and AD3 I In). These values are used in a feedback architecture to adjust the pulse width modulation of the switch 306. For instance, the duty cycle of the switch 306 can vary from about 20% to about 80%, depending on the desired and actual output from the switch 306.

The drive circuit 308, which receives the signal from the switch 306, includes an oscillatory circuit that turns the output of the switch 306 into an electrical signal having a single ultrasonic frequency, e.g., 55 kHz (referred to as VCO in FIG. 3). As will be explained below, a smoothed-out version of this ultrasonic waveform is ultimately fed to the transducer 316 to produce a resonant sine wave along the waveguide 318. Resonance is achieved when current and voltage are substantially in phase at the input of the transducer 316. For this reason, the drive circuit 308 uses a PLL to sense the current and voltage input to the transducer 316 and to synchronize the current and voltage with one another. This sensing is performed over line 328. However, unlike prior-art devices that simply match the phase of the input current to the phase of the input voltage, the present invention utilizes the inventive concept of matching the current phase with a phase of the "motional" voltage and/or matches the input voltage phase with a phase of the "motional" current. The concept and technique of measuring motional voltage will be explained in detail below and in conjunction with the figures.

At the output of the drive circuit 308 is a transformer 310 able to step up the low voltage signal(s) to a higher voltage. It is noted that all upstream switching, prior to the transformer 310, has been performed at low (i.e., battery driven) voltages, something that, to date, has not been possible for ultrasonic cutting and cautery devices. This is at least partially due to the fact that the drive circuit 308 advantageously uses low on-resistance MOSFET switching devices. Low on-resistance MOSFET switches are advantageous, as they produce less heat than traditional MOSFET device and allow higher current to pass through. Therefore, the switching stage (pre transformer) can be characterized as low voltage/high current.

In one embodiment of the present invention, the transformer 310 steps up the battery voltage to 120V RMS. Transformers are known in the art and are, therefore, not explained here in detail. The output of the transformer 310 resembles a square wave 400, an example of which is shown in FIG. 4, which waveform is undesirable because it is injurious to certain components, in particular, to the transducer 316. The square wave also generates interference between components. The matching circuit 312 of the present invention substantially reduces or eliminates these problems.

The wave shaping or matching circuit 312, sometimes referred to as a "tank circuit," smoothes the square wave 400 output from the transformer 310 and turns it into a driving wave 500 (e.g., a sine wave) an approximation of which is shown in FIG. 5. The matching circuit 312, in one embodiment of the present invention, is a series L-C circuit and is controlled by the well-known principles of Kirchhoff's circuit laws. However, any matching circuit can be used here. The smooth sine wave 500 output from the matching circuit 312 is, then, fed to the transducer 316. Of course, other driving signals can be output from the matching circuit 312 that are not smooth sine waves.

A transducer 316 is an electro-mechanical device that converts electrical signals to physical movement. In a broader sense, a transducer is sometimes defined as any device that converts a signal from one form to another. An analogous transducer device is an audio speaker, which converts electrical voltage variations representing music or speech to mechanical cone vibration. The speaker cone, in turn, vibrates air molecules to create acoustical energy. In the present invention, the driving wave 500 is input to the transducer 316, which then imparts physical movements to the waveguide 318. As will be shown, this movement sets up a resonating wave on the waveguide 318, resulting in motion at the end of the waveguide 318.

FIG. 6 provides a diagrammatic illustration of the effect that a resonant sine wave input to a transducer has on a waveguide of the ultrasonic cutting device in accordance with an exemplary embodiment of the present invention with the sinusoidal pattern shown representing the amplitude of axial motion along the length of the waveguide. As can be seen in FIG. 6, the transducer 316 is coupled to the waveguide 318. Responding to a positive portion 502 of the driving sine wave 500, the transducer 316 moves a portion 604 of the transducer 316, which is physically attached to a portion 606 of the attached waveguide 318, in a first direction 608. Likewise, the transducer 316 responds to a negative portion 504 of the driving wave 500 and moves the portion 604 of the transducer 316 in a second direction 612. A smooth sine wave 500, in contrast to the square wave 400, allows the transducer 316 and waveguide 318 to slow before changing directions. The smoother movement is less injurious to the device's components. One exemplary embodiment of the portion 604 is a stack of piezo-electric crystals.

The alternating movement 608, 612 of the transducer portion 604 places a sinusoidal wave 614 along the length of the waveguide 318. The wave 614 alternatively pulls the end 620 of the waveguide 318 toward the transducer 316 and pushes it away from the transducer 316, thereby longitudinally moving the tip 620 of the waveguide 318 along distance 618. The tip is considered an "anti-node," as it is a moving point of the sine wave 614. The resulting movement of the waveguide 318 produces a "sawing" movement along distance 618 at the end of the waveguide 318. (The wave 614 and linear movement along distance 618 are greatly exaggerated in FIG. 6 for ease of discussion.) This high-speed movement along distance 618, as is known in the art, provides a cutting waveguide that is able to slice easily through many materials, such as tissue and bone. The waveguide 318 also generates a great deal of frictional heat when so stimulated, which heat is conducted within the tissue that the waveguide 318 is cutting. This heat is sufficient to cauterize instantly blood vessels within the tissue being cut.

If the driving wave 614 traveling along the waveguide 318 is not a resonant wave, the last anti-node of the wave 614 will not appear at the tip 620 of the waveguide 318. In such a case, the tip 620 of the waveguide 318 may move transverse to the longitudinal axis of the waveguide 318, creating an incorrect mode, e.g. the tip 620 not moving, a slapping motion with the tip 620, or several others. This incorrect mode is not ideal and is not reliable for providing adequate cutting and surgical cautery. The invention, however, utilizes the PLL in the drive circuit 308 to ensure that the movement 608, 612 of the waveguide 318 remains resonant along the waveguide 318 by monitoring the phase between the motional current and motional voltage waveforms fed to the transducer 316 and sending a correction signal back to the drive circuit 308. As an added feature, the present invention can be provided with piezo-electric crystal stacks 604 that are cut in a different plane, thereby creating a torsional, or twisting motion of the blade rather than only a sawing motion. The present invention can easily be adapted to a full set of uses using requiring a drilling-type motion instead of or with the sawing motion just described.

Transducer Circuit Model

Figure 7:
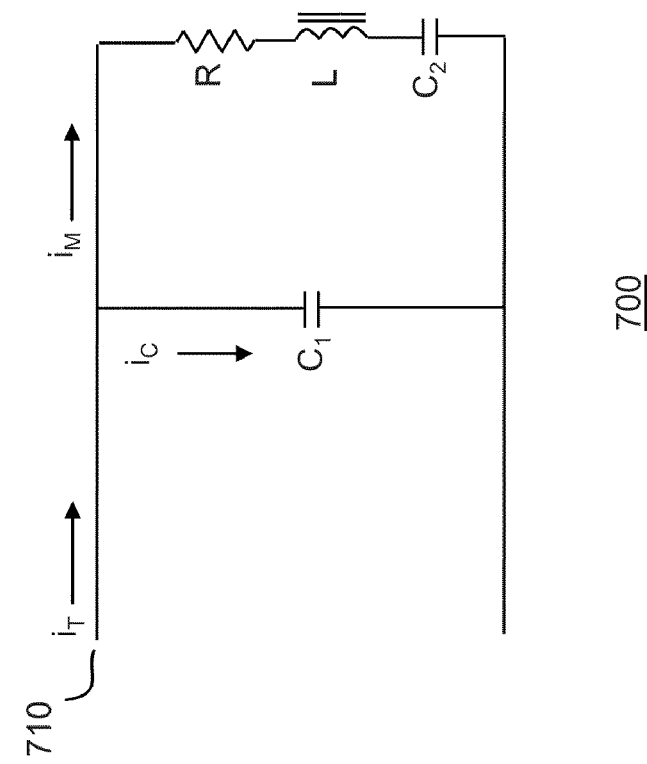
FIG. 7 is a fragmentary, schematic circuit diagram of an elemental series circuit model for a transducer in accordance with an exemplary embodiment of the present invention.

FIG. 7 is a schematic circuit diagram of a model transducer 700, such as transducer 316, which contains piezo-electric material. Piezo-electric transducers are well known in the art. The mass and stiffness of the piezo-electric material creates a mechanically resonant structure within the transducer. Due to the piezo-electric affect, these mechanical properties manifest themselves as electrically equivalent properties. In other words, the electrical resonant frequency seen at the electrical terminals is equal to the mechanical resonant frequency. As shown in FIG. 7, the mechanical mass, stiffness, and damping of the transducer 316 may be represented by a series configuration of an inductor/coil L, a capacitor $C_2$, and a resistor R, all in parallel with another capacitor $C_1$. The electrical equivalent transducer model 700 is quite similar to the well-known model for a crystal.

Flowing into an input 710 of the electrical equivalent transducer model 700 is a transducer current $i_T$. A portion $i_C$ of $i_T$ flows across the parallel capacitor $C_1$, which is of a selected type and value that, for the majority of the expected frequency range, retains a substantially static capacitive value. The remainder of $i_T$, which is defined as $i_M$, is simply $i_T - i_C$ and is the actual working current. This remainder current $i_M$ is referred to herein as the "motional" current. That is, the motional current is that current actually performing the work to move the waveguide 318.

Known prior-art designs regulate and synchronize with the total current $i_T$, which includes $i_C$ and is not an indicator of the actual amount of current actually causing the motion of the waveguide 318 of the transducer 316. For instance, when the blade of a prior-art device moves from soft tissue, to more dense material, such as other tissue or bone, the resistance R increases greatly. This increase in resistance R causes less current $i_M$ to flow through the series configuration R-L-$C_2$, and more current $i_C$ to flow across capacitive element $C_1$. In such a case, the waveguide 318 slows down, degrading its performance. It may be understood by those skilled in the art that regulating the overall current is not an effective way to maintain a constant waveguide speed. As such, one novel embodiment of the present invention advantageously monitors and regulates the motional current $i_M$ flowing through the transducer 316. By regulating the motional current $i_M$, the movement distance of the waveguide 318 can be regulated easily.

Surgical Device Circuit Model

Figure 8:
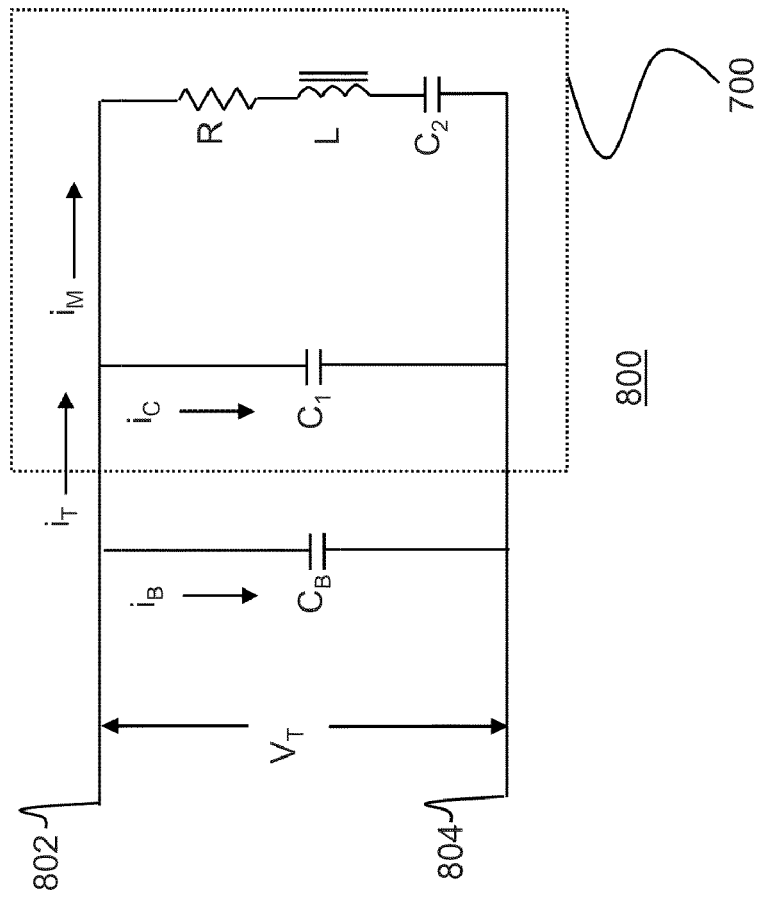
FIG. 8 is a fragmentary, schematic circuit diagram of an inventive circuit with the circuit of FIG. 7 and is useful for monitoring a motional current of a transducer in accordance with an exemplary embodiment of the present invention.

FIG. 8 is a schematic circuit diagram of an inventive circuit 800 useful for understanding how to obtain the motional current $i_M$ of a transducer 700. The circuit 800 has all of the circuit elements of the transducer 700 plus an additional bridging capacitive element $C_B$ in parallel with the transducer 700 of FIG. 7. However, the value of $C_B$ is selected so that $C_1/C_B$ is equal to a given ratio r. For efficiency, the chosen value for $C_B$ should be relatively low. This limits the current that is diverted from $i_M$. A variable power source $V_T$ is applied across the terminals 802 and 804 of the circuit 800, creating a current $i_B$ through the capacitive element $C_B$, a current $i_T$ flowing into the transducer 700, a current $i_C$ flowing through capacitor $C_1$, and, finally, the motional current $i_M$. It then follows that $i_M = i_T - r \cdot i_B$. This is because:

$$i_B = C_B \cdot \frac{\partial V_T}{\partial t} = \frac{C_1}{r} \cdot \frac{\partial V_T}{\partial t} \text{ and } i_C = C_1 \cdot \frac{\partial V_T}{\partial t}$$

Therefore, $i_C = r \cdot i_B$ and, substituting for $i_C$ in the equation $i_M = i_T - i_C$, leads to: $i_M = i_T - r \cdot i_B$.

Now, by knowing only the total current and measuring the current through the bridge capacitor $i_B$, variations of the transducer's motional current $i_M$ can be identified and regulated. The driver circuit 308, then, acts as a current controller and regulates the motional current $i_M$ by varying an output of the transformer 310 based on the product of the current flowing through the bridge capacitance $C_B$ multiplied by the ratio r subtracted from a total current $i_T$ flowing into the transducer 700. This regulation maintains a substantially constant rate of movement of the cutting blade portion of the waveguide 318 across a variety of cutting loads—something that has not been possible to date. In one embodiment, the sensing circuits 314 measure the motional voltage and/or motional current. Current and voltage measuring devices and circuit configurations for creating voltage meters and current meters are well known in the art. Values of current and voltage can be determined by the present invention in any way now known or later developed, without limitation.

Regulation of the motional current $i_M$ is a true way to maintain the integrity of the instrument and ensure that it will operate at its peak performance under substantially all conditions expected in an operating environment. In addition, such regulation provides these advantages within a package small enough and light enough to be easily held in one hand—a configuration that has never occurred in the field.

Transducer Circuit Model

Figure 9:
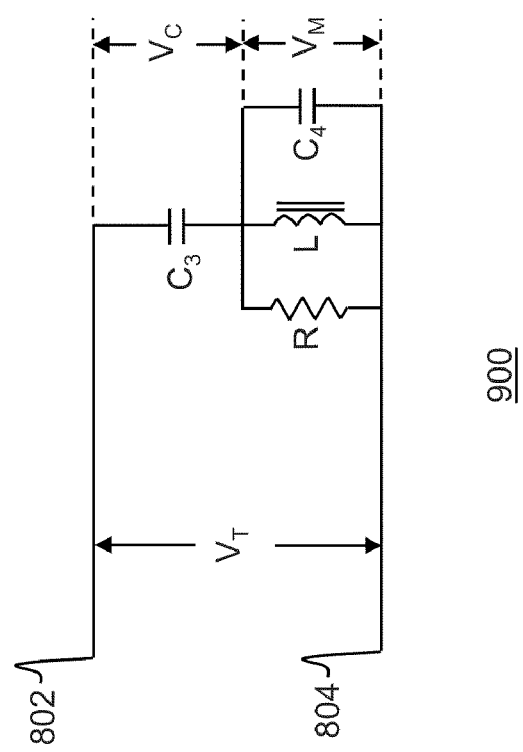
FIG. 9 is a fragmentary, schematic circuit diagram of an elemental parallel circuit model of a transducer in accordance with an exemplary embodiment of the present invention.

FIG. 9 shows another embodiment of the present invention, where the transducer 316 is schematically represented as a parallel configuration of a resistive element R, an inductive element L, and a capacitive element $C_4$. An additional capacitive element $C_3$ is in a series configuration between an input 802 and the parallel configuration of the resistive element R, the inductive element L, and the capacitive element $C_4$. This parallel representation models the action of the transducer in the "antiresonant" mode of operation, which occurs at a slightly different frequency. A transducer voltage $V_T$ is applied between the input terminals 802, 804 of the transducer 316. The transducer voltage $V_T$ is split between a voltage $V_C$ across capacitive element $C_3$ and a motional voltage $V_M$ across the parallel configuration of the resistive element R, the inductive element L, and the capacitive element $C_4$. It is the motional voltage $V_M$ that performs the work and causes the waveguide 318 to move. Therefore, in this exemplary embodiment, it is the motional voltage that should be carefully regulated.

Surgical Device Circuit Model

Figure 10:
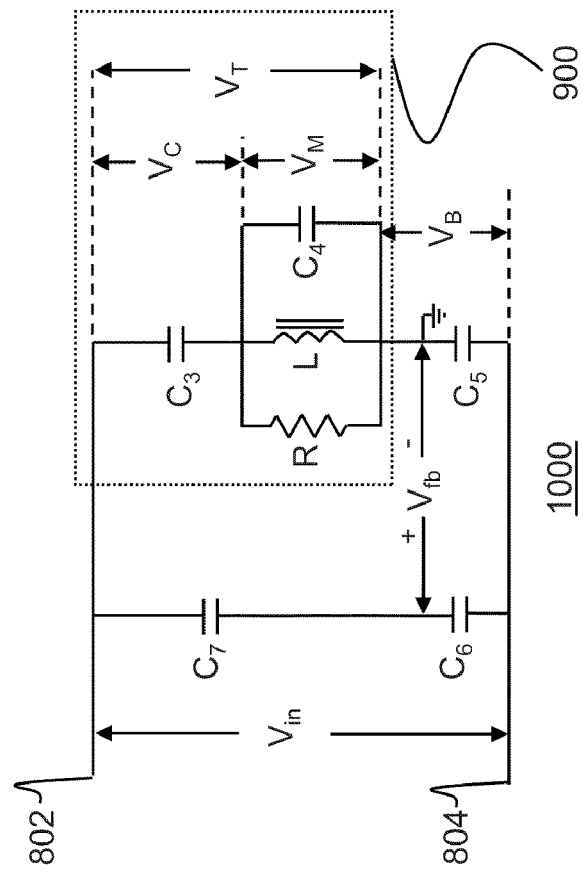
FIG. 10 is fragmentary, schematic circuit diagram of an inventive circuit with the circuit of FIG. 9 and is useful for monitoring the motional current of a transducer in accordance with an exemplary embodiment of the present invention.

FIG. 10 shows an exemplary embodiment of an inventive circuit configuration 1000, according to the present invention. The circuit configuration 1000 includes the transducer 900 of FIG. 9 and adds to it three additional capacitive elements $C_5$, $C_6$, and $C_7$. Capacitive element $C_5$ is in series with the transducer circuit 900 of FIG. 9 while the capacitive elements $C_6$ and $C_7$ are in series with one another and, together, are in parallel with the series combination of the capacitive element $C_5$ and the transducer circuit 900.

This circuit is analogous to a Wheatstone bridge measuring instrument. Wheatstone bridge circuits are used to measure an unknown electrical resistance by balancing two legs of a bridge circuit, one leg of which includes the unknown component. In the instant circuit configuration shown in FIG. 10, a motional voltage $V_M$, which equals $V_T - V_C$, is the unknown. By determining and regulating the motional voltage $V_M$, the inventive configuration allows a consistent waveguide movement to be maintained as set forth below.

Advantageously, the capacitive element $C_7$ is selected so that its value is a ratio A of capacitive element $C_3$, with A being less than one. Likewise, the capacitive element $C_6$ is selected so that its value is the same ratio A of the capacitive element $C_5$. The ratio of $C_5/C_3$ is also the ratio A.

Because the ratio of $C_3/C_7$ is A and the ratio of $C_5/C_6$ is also A, the bridge is balanced. It then follows that the feedback voltage $V_{fb}$, divided by the motional voltage $V_M$, is also the ratio A. Therefore, $V_m$ can be represented as simply $A \cdot V_{fb}$.

If the voltage across the transducer 900 is still $V_T$, an input voltage $V_{in}$ equals $V_T$ plus the voltage $V_B$ across the capacitive element $C_5$. The feedback voltage $V_{FB}$ is measured from a first point located between capacitive elements $C_6$ and $C_7$ and a second point located between the transducer and the capacitive element $C_5$. Now, the upstream components of the circuit 300 act as a voltage controller and vary the power $V_{in}$ to maintain a constant feedback voltage $V_{fb}$, resulting in a substantially constant motional voltage and maintaining a substantially constant rate of movement of the cutting blade portion of the waveguide 318 across a variety of cutting loads. Again, unlike the prior art, the present invention is not simply regulating the input voltage $V_{in}$, it is varying the input voltage $V_{in}$ for the purpose of regulating the motional voltage $V_M$—which is novel in the art.

Figure 11:
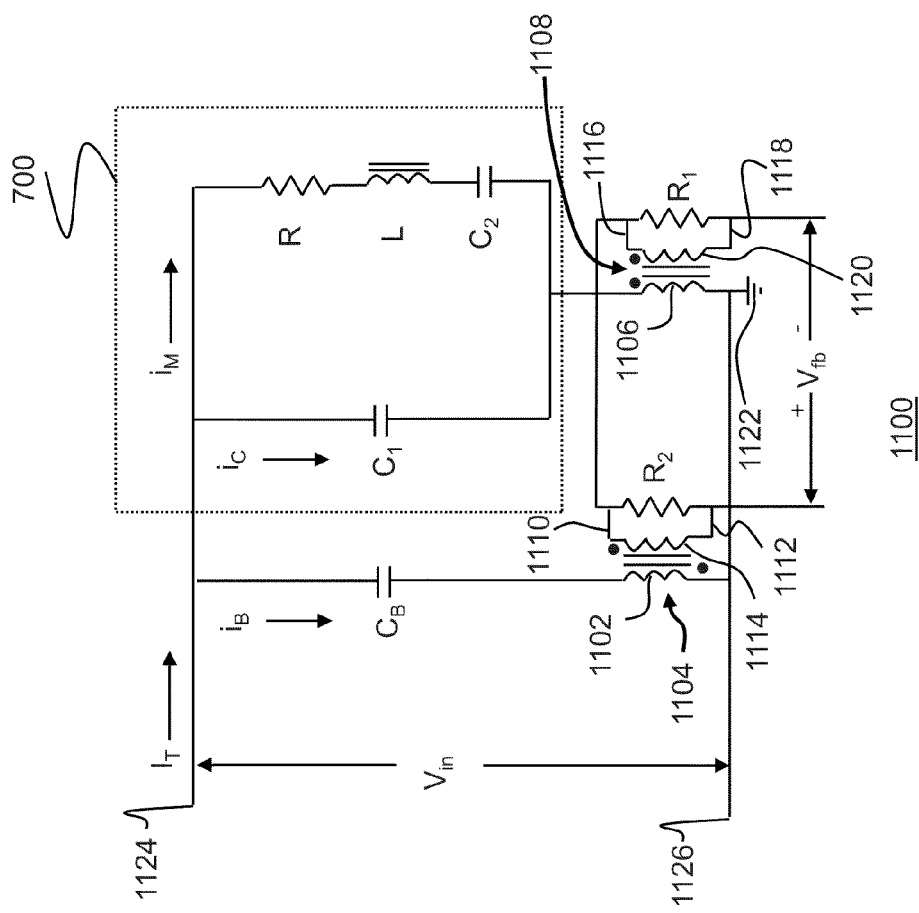
FIG. 11 is a fragmentary, schematic circuit diagram of an inventive circuit with the circuit of FIG. 7 and is useful for monitoring the motional current of a transducer in accordance with an exemplary embodiment of the present invention.

FIG. 11 shows another embodiment of the present invention where the transducer 700 is of the circuit configuration shown in FIG. 7. The configuration of FIG. 11 works similarly to that shown in FIG. 8 and as described above in connection with FIG. 8. However, in this circuit configuration 1100, a pair of transformers 1104 and 1108 is used to determine and monitor the motional voltage $V_M$. In this embodiment, a primary winding 1102 of the first transformer 1104 is in a series configuration with a bridge capacitor $C_B$. Similarly, a primary winding 1106 of the second transformer 1108 is in a series configuration with the transducer 700. The leads 1110 and 1112 of the secondary winding 1114 of the first transformer 1104 are coupled through a resistor $R_2$. The leads 1116 and 1118 of the secondary winding 1120 of the second transformer 1108 are coupled through a resistor $R_1$. In addition, the first lead 1110 of the secondary winding 1114 of the first transformer 1104 is directly connected to the first lead 1116 of the secondary winding 1120 of the second transformer 1108.

Current $i_B$ passing through the primary winding 1102 of the first transformer 1104 induces a current in the secondary winding 1114 of the first transformer 1104. Similarly, the currents including $i_C$ passing through the capacitive element $C_1$ of the transducer 700 and the motional current $i_M$ of the transducer 700 combine and go through the primary winding 1106 of the second transformer 1108 to find ground 1122. The current in the primary winding 1106 induces a current on the secondary winding 1120. As noted by the dots ("●") on the transformers 1104, 1108, the secondary windings 1114 and 1120 are in opposite directions from one another, with reference to the primary windings 1102, 1106, respectively, and induce a voltage $V_{fb}$ across resistors $R_1$ and $R_2$. By selecting values for $R_1$ and $R_2$ so that a ratio of $R_1/R_2$ is equal to the ratio of the values $C_B/C_1$, the feedback voltage $V_{fb}$ will always be proportional to the motional current $i_M$. Now, the upstream components of the circuit 300 (see FIG. 3) act as a voltage controller and vary the input power ($V_{in}$ and $I_T$) to maintain a constant feedback voltage $V_{fb}$, resulting in a substantially constant motional current $i_M$ and maintaining a substantially constant rate of movement of the cutting blade portion of the waveguide 318 across a variety of cutting loads. Again, unlike the prior art, the present invention is not simply regulating the input voltage $V_{in}$, it is varying the input current $I_T$ for the purpose of regulating the motional current $i_M$—which is novel in the art.

Figure 12:
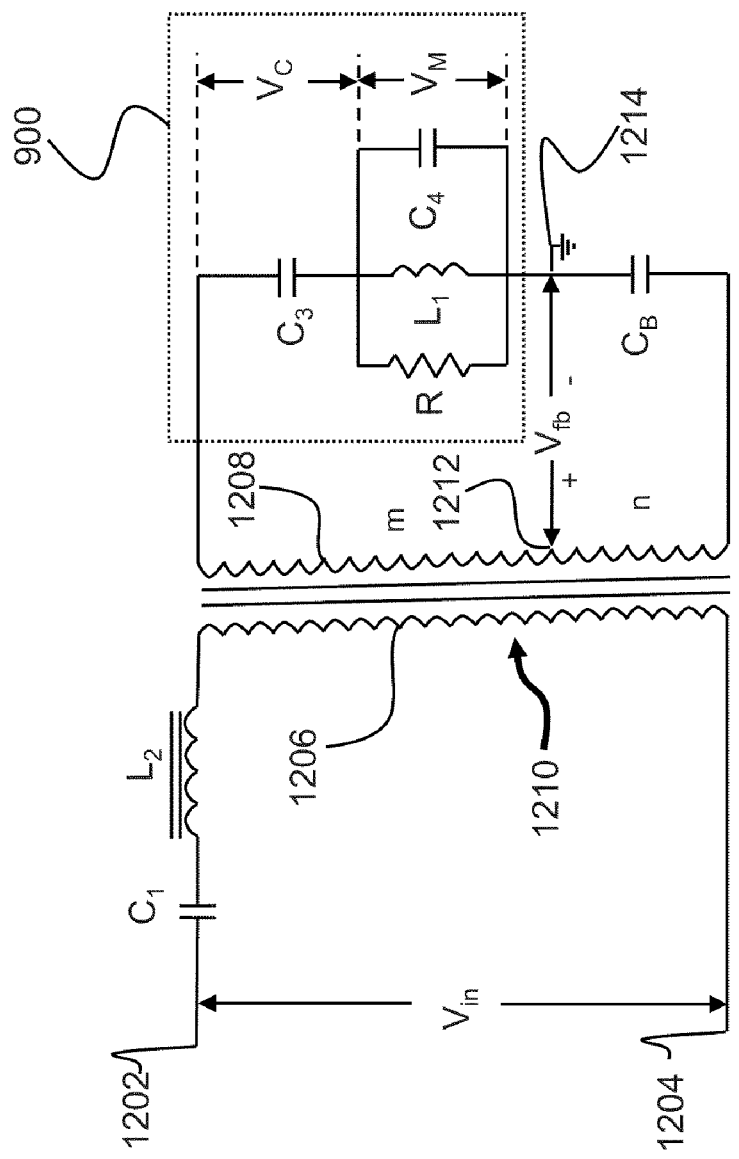
FIG. 12 is a fragmentary, schematic circuit diagram of an inventive circuit with the circuit of FIG. 9 and is useful for monitoring the motional current of a transducer in accordance with an exemplary embodiment of the present invention.

FIG. 12 shows another embodiment of the present invention where the transducer 900 is modeled by the circuit configuration shown in FIG. 9. The configuration of FIG. 12 works similarly to that shown in FIG. 10 and as described above in connection with FIG. 10. However, in this circuit configuration 1200, a transformer 1210 is used to determine and monitor the motional voltage $V_M$ of the transducer 900. In this embodiment, a primary winding 1206 of the transformer 1210 is in a series circuit configuration with an inductive element $L_2$ and a capacitive element $C_1$. A voltage $V_{in}$ is applied across input leads 1202 and 1204 of the circuit formed by the primary winding 1206 of the transformer 1210, the inductive element $L_2$, and the capacitive element $C_1$. A current through the primary winding 1206 induces a corresponding current in the secondary winding 1208 of the transformer 1210. The secondary winding 1208 of the transformer 1210 is in a parallel configuration with a combination of the transducer 900 and a bridge capacitor $C_B$. The two components forming the combination are in a series configuration.

In this embodiment, the secondary winding 1208 is tapped at a point 1212. By tapping the secondary winding 1208 at a point where a first portion of the secondary winding 1208 has m turns and a second portion of the secondary winding 1208 has n turns (where n is less than m), a selectable percentage of the induced voltage on the secondary winding 1208 appears from point 1212 to ground 1214.

Again, this circuit is analogous to a Wheatstone bridge measuring instrument. One leg is the first secondary winding m, the second leg is the second secondary winding n, the third leg is the transducer 900, and the fourth leg is the capacitor $C_B$. In the instant circuit configuration shown in FIG. 12, the voltage $V_M$ is the unknown. By determining and regulating the motional voltage $V_M$, a consistent waveguide movement is maintained.

By selecting a value of the bridge capacitor $C_B$ to be less than the transducer capacitance $C_3$ by the same percentage that the number of turns n is less than the number of turns m (i.e., $m/n=C_3/C_B$), the value of a feedback voltage $V_{fb}$ will reflect the motional voltage $V_M$. The invention can determine whether the motional voltage $V_M$ is changing by monitoring the feedback voltage $V_{fb}$ for changes.

By using the equivalent-circuit transducer model 900, which models a parallel-resonant (or "anti-resonant") transducer, the transducer may be driven in the parallel resonant mode of operation, where motion is proportional to voltage. The advantage of this mode of operation is that the required constant-voltage-mode power supply is simpler to design and safer to operate than a constant-current-mode power supply. Also, because the transducer has a higher impedance when unloaded (rather than a lower impedance when unloaded in the series-resonant mode of operation), it naturally tends to draw less power when unloaded. The parallel-resonant mode of operation, however, is more difficult to maintain because the resonant bandwidth is narrower than that of the series-resonant mode and it has a slightly different natural resonant frequency; hence, the mechanical components of the device must be specifically configured to operate at either the series resonant or parallel-resonant mode of operation.

Now, the upstream components of the circuit 300 act as a voltage controller and vary the power $V_{in}$ to maintain a constant feedback voltage $V_{fb}$, resulting in a substantially constant motional voltage $V_M$ and maintaining a substantially constant rate of movement of the cutting blade portion of the waveguide 318 across a variety of cutting loads. Again, unlike the prior art, the present invention is not simply regulating the input voltage $V_{in}$, it is varying the input voltage $V_{in}$ for the purpose of regulating the motional voltage $V_M$—which is novel in the art.

In each of the circuit configurations described and shown in FIGS. 7-12, circuit component degradation can impact negatively the entire circuit's performance. One factor that directly affects component performance is heat. Known circuits generally monitor switching temperatures (e.g., MOSFET temperatures) However, because of the technological advancements in MOSFET designs, and the corresponding reduction in size, MOSFET temperatures are no longer a valid indicator of circuit loads and heat. For this reason, the present invention senses with the sensing circuit 314 the temperature of the transformer 310 according to an exemplary embodiment. This temperature sensing is very advantageous as transformer 310 is run at or very close to its maximum temperature during use of the device. Additional temperature will cause the core material, e.g., the ferrite, to break down and permanent damage can occur. The present invention can respond to a maximum temperature of the transformer 310 by, for example, reducing the driving power in the transformer 310, signaling the user, turning the power off completely, pulsing the power, or other appropriate responses.

Referring back to FIG. 1, in one embodiment, the processor 302 is communicatively coupled to the clamping mechanism 118, which is used to place material in physical contact with the blade portion of the waveguide 318. The clamping mechanism 118 has a range of clamping force values and the processor 302 varies the motional voltage $V_M$ based upon the received clamping force value. Because high force values combined with a set motional rate can result in high blade temperatures, a temperature sensor 322 can be communicatively coupled to the processor 302, where the processor 302 is operable to receive and interpret a signal indicating a current temperature of the blade from the temperature sensor 322 and determine a target frequency of blade movement based upon the received temperature.

According to an embodiment of the present invention, the PLL 308, which is coupled to the processor 302, is able to determine a frequency of waveguide (318) movement and communicate the frequency to the processor 302. The processor 302 stores this frequency value in the memory 326 when the device is turned off. By reading the clock 330, the processor 302 is able to determine an elapsed time after the device is shut off and retrieve the last frequency of waveguide movement if the elapsed time is less than a predetermined value. The device can then start up at the last frequency, which, presumably, is the optimum frequency for the current load.

Transducer

FIGS. 13 to 30 show various exemplary embodiments of a "gun" type device 1300, 1800, 2300 suitable to hold and/or contain the entire inventive device illustrated in the diagram of FIG. 3. More specifically, as shown in the cutaway view of FIG. 14, the ultrasonic surgical device 1300 includes a disposable ultrasonic cutting tool handle 1408 that has a watertight sealable battery-holding compartment 1422, a driving-wave generation circuit 1420 in electrical contact with the battery-holding compartment 1422, a transducer attachment dock 1404 accessible from an exterior of the handle and operable to releasably physically couple the transducer 1302 to a waveguide 1310 (represented as a dotted line in FIG. 13) coupled to the handle 1408 through a waveguide attachment dock 1406 that is disposed to accept and physically couple the ultrasonic waveguide 1310 to the transducer 1302.

Figure 41:
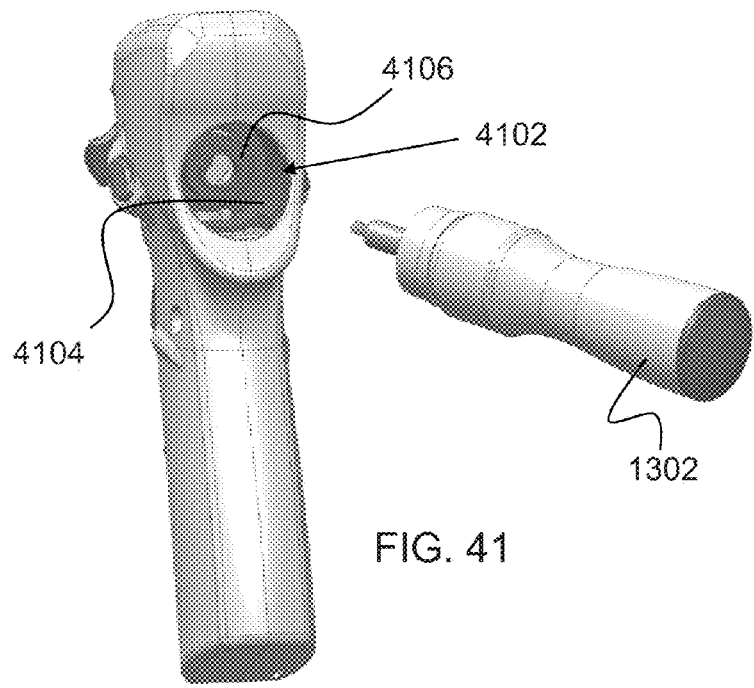
FIG. 41 is a perspective rear view of view of the exemplary handle of FIG. 13 with the transducer removed in accordance with an exemplary embodiment of the present invention.
Figure 42:
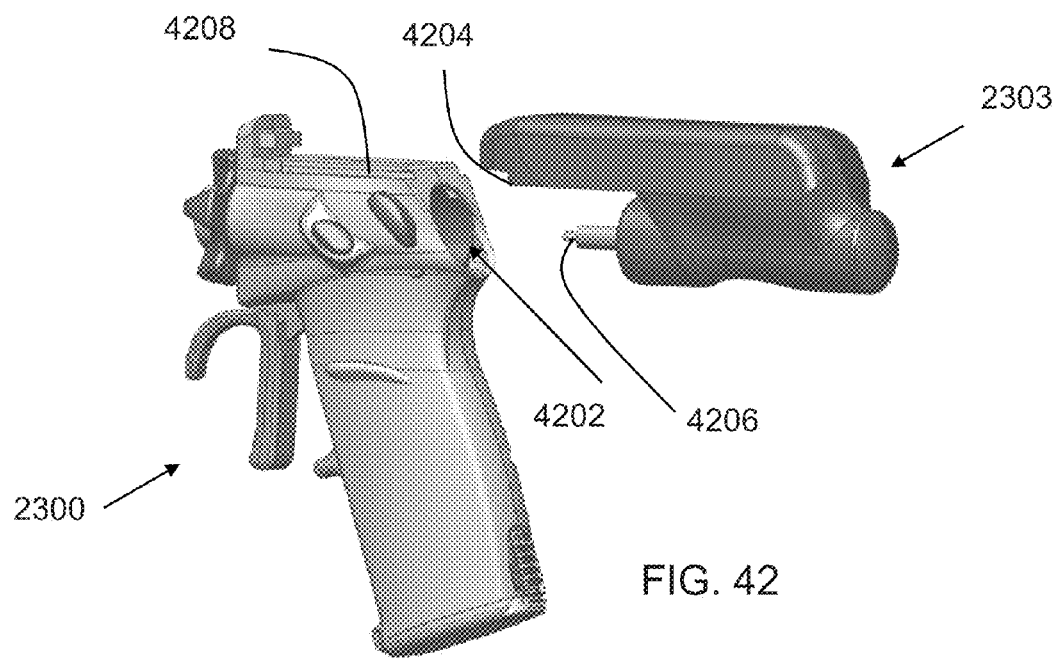
FIG. 42 is a perspective view of the exemplary handle of FIG. 23 with the waveguide-movement-generation assembly removed in accordance with an exemplary embodiment of the present invention.
Figure 43:
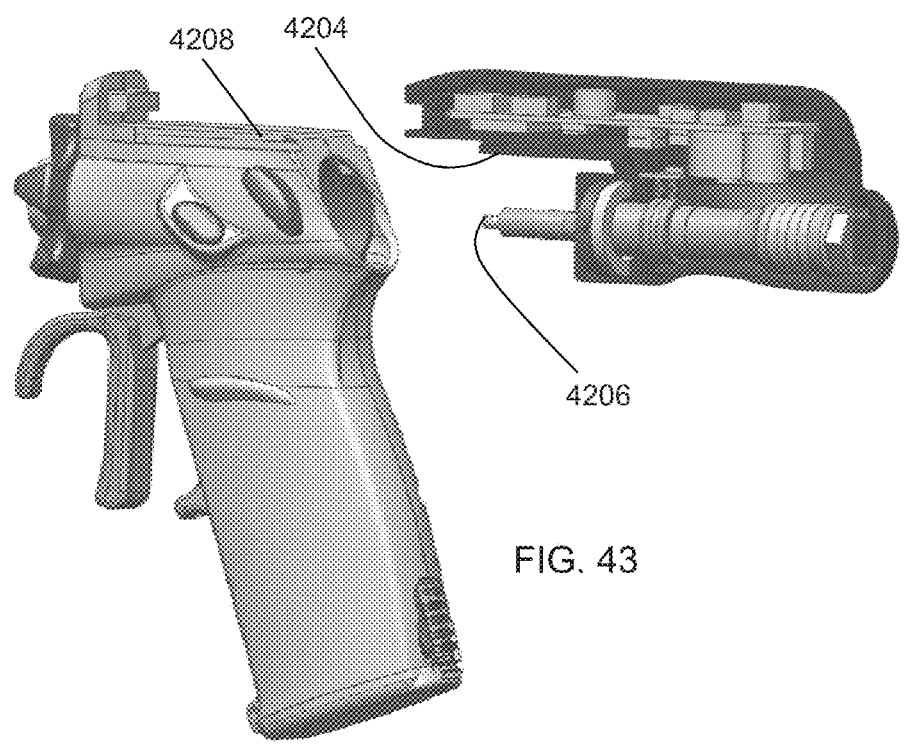
FIG. 43 is a perspective cutaway view of the exemplary removed waveguide-movement-generation assembly of FIG. 43 in accordance with an exemplary embodiment of the present invention.

The ultrasonic surgical device 1300 includes a disposable handle body 1308 defining a battery-holding compartment 1422 shaped to receive a battery 1700 therein and operable to couple a proximal end of the ultrasonic waveguide 1310 to the ultrasonic transducer 1302 therethrough. The handle body 1308 has a transducer dock 4102 (shown best in FIG. 41) exposed to the environment and shaped to interchangeably house at least a portion of the transducer 1302 thereat. The handle body 1308 further includes a waveguide attachment dock 1428 shaped to align and attach the proximal end of the waveguide 1310 to the transducer 1302 and thereby hold the waveguide 1310 and the transducer 1302 at least partially within the body when the transducer 1302 is docked in the transducer dock 4102 and the waveguide 1310 is docked in the waveguide attachment dock 1428.

An upper portion of the handle body 1308 houses a disposable driving-wave generation circuit 1420 that is in electrical contact with the battery 1700 and the transducer 1302 when the battery 1700 and transducer are disposed, respectively, in the battery-holding compartment 1422 and the transducer dock 4102. The generation circuit 1420 is operable to generate an output waveform sufficient to generate ultrasonic movement along the waveguide by exciting the transducer when the transducer is coupled to the waveguide 1310.

The transducer 1302 is generally secured by screwing the transducer 1302 onto a waveguide 1310, both being at least partially within the transducer port 1404. The physical couple between the handle 1408 and the transducer 1302, once attached, can be water-tight and, in some embodiments, can be aseptic. As explained above, the transducer 1302 imparts the physical forces to the waveguide 318 at the proper frequency and force and receives power from the battery 1700 through conductive power leads 1426. The transducer assembly 1302 is shown in greater detail in FIGS. 15 and 16.

Figure 15:
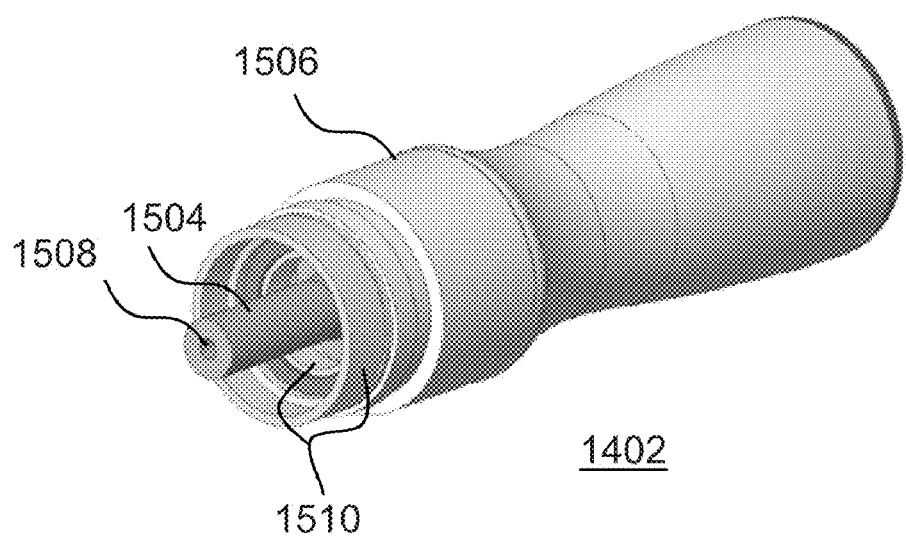
FIG. 15 is a perspective view of a transducer assembly removed from the exemplary handle of FIG. 14 in accordance with an exemplary embodiment of the present invention.

Referring to FIG. 15, the reusable cordless transducer assembly 1402 is shown separate from the device 1300. The inventive transducer assembly 1402 includes a shaft 1504 with an ultrasonic waveguide couple 1508 that is able to attach to a waveguide and, upon activation of the transducer shaft 1504, excite the attached waveguide, i.e., impart ultrasonic waves along the length of the waveguide. The transducer assembly 1402 also has a housing 1506 that protects and seals the internal working components (shown in FIG. 16) from the environment. It is advantageous for the transducer assembly 1402 to be selectively removable from the device 1300. As a separate component, the transducer assembly 1402 can be medically disinfected or sterilized, e.g., put in an autoclave, and used for multiple surgeries, while the less-expensive gun itself may be disposable. In addition, the transducer assembly 1402 can be used in multiple guns or in the same gun up to a desired maximum number of times before it is required to be disposed.

Figure 16:
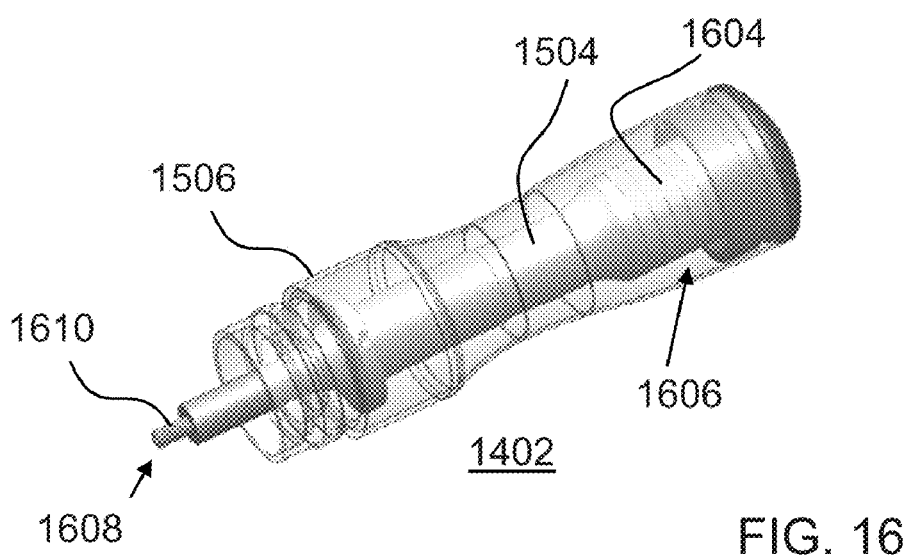
FIG. 16 is a perspective and partially hidden view of the transducer assembly of FIG. 15 in accordance with an exemplary embodiment of the present invention.

FIG. 16 shows one exemplary embodiment of the transducer assembly 1302. Within the housing 1506 is the movable shaft 1504. When an electric field is created in the piezoelectric crystal stack 1604 at one end 1606 of the shaft 1504, the shaft 1504 moves laterally within and relative to the housing 1506. In this embodiment, the waveguide coupler 1508 is male and includes threads 1610, which are used to secure the transducer assembly 1302 to the non-illustrated waveguide 318 by screwing the waveguide 318 onto the threads 1610 with an appropriate amount of torque. In contrast, in FIG. 15, the waveguide coupler 1508 was female allowing the waveguide to be screwed into the waveguide coupler 1508.

A novel feature of the transducer 1402 is its ability to mechanically and electrically connect at the same time. FIG. 15 shows an exemplary embodiment of electrical connector rings 1510 of the transducer 1402. As the transducer 1402 is being coupled by the waveguide couple 1508 to a waveguide attached to the handle 1408, the connector rings 1510 are brought into contact with, for example, a set of power contacts 4104, shown in FIG. 41. The power contacts 4104 places the piezoelectric crystal stack 1604 in contact with the power source 1700 of the handle 1408. This substantially simultaneous coupling can be configured to occur in all embodiments of the present invention.

The transducer assembly 1302 and the transducer assembly housing 1404 can be sealed so that, in the rare event of surgical fluids contacting the transducer assembly 1302, they will not introduce themselves into the interior of the housing 1506.

Figure 17:
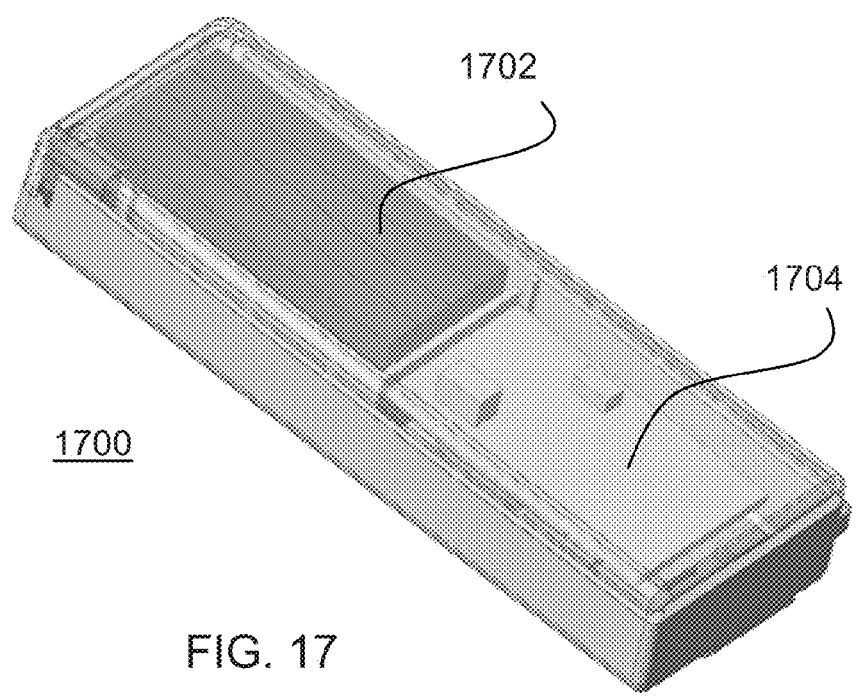
FIG. 17 is a perspective and partially hidden view of the pack shown in the handle of FIG. 14 in accordance with an exemplary embodiment of the present invention.

The gun 1300, according to an exemplary embodiment of the present invention, has, within its handle 1408, a power assembly 1700 (including power source 1702 and a generator 1704), referred to herein as a battery-and-generator assembly or "BAG" 1700, shown in detail in FIG. 17. The battery 1702 within the BAG 1700 can be a single battery or a plurality of battery cells operating as a unit. Both battery configurations (single or multiple cells) will be referred to herein as the "battery" 1702 herein.

The battery 1702 powers the generator 1704, which can include some or all of the components shown in FIG. 3 and described in detail above. Specifically, the generator 1704 powers the transducer and includes the processor 302, the switch 306 (e.g., a MOSFET power switch), the drive circuit 308 (PLL), the transformer 310, the signal smoothing/matching circuit 312, and the sensing circuit 314. The present invention's ability to provide all of the necessary reusable generator components of the ultrasonic cutting tool within the disposable handle 1408 of the gun-type device 1300 provides a great advantage over prior-art devices, which house a majority of the device components within the very expensive and heavy desktop box 202 shown in FIG. 2 and which also creates an expensive and bulky tether 208 between the device (FIGS. 1 and 2) and the box 202. The inventive circuit techniques of the present invention sever the dependency on high voltage (120 VAC) input power, a characteristic of all prior-art ultrasonic cutting devices, and utilizes only low-voltage switching throughout the wave-forming process.

In addition to the advantages of reduced cost, reduced size, elimination of a tethering cord for supplying power and carrying signals, and a constant motional voltage, the instant invention provides unique advantages for maintaining a sterile environment in an operating or other environment. More specifically, in exemplary embodiments of the present invention, the handle includes an aseptic seal. An "aseptic" seal, as used herein, means a seal that sufficiently isolates a compartment (e.g., inside the handle) and components disposed therein from a sterile field of an operating environment into which the handle has been introduced so that no contaminants from one side of the seal are able to transfer to the other side of the seal.

Figure 14:
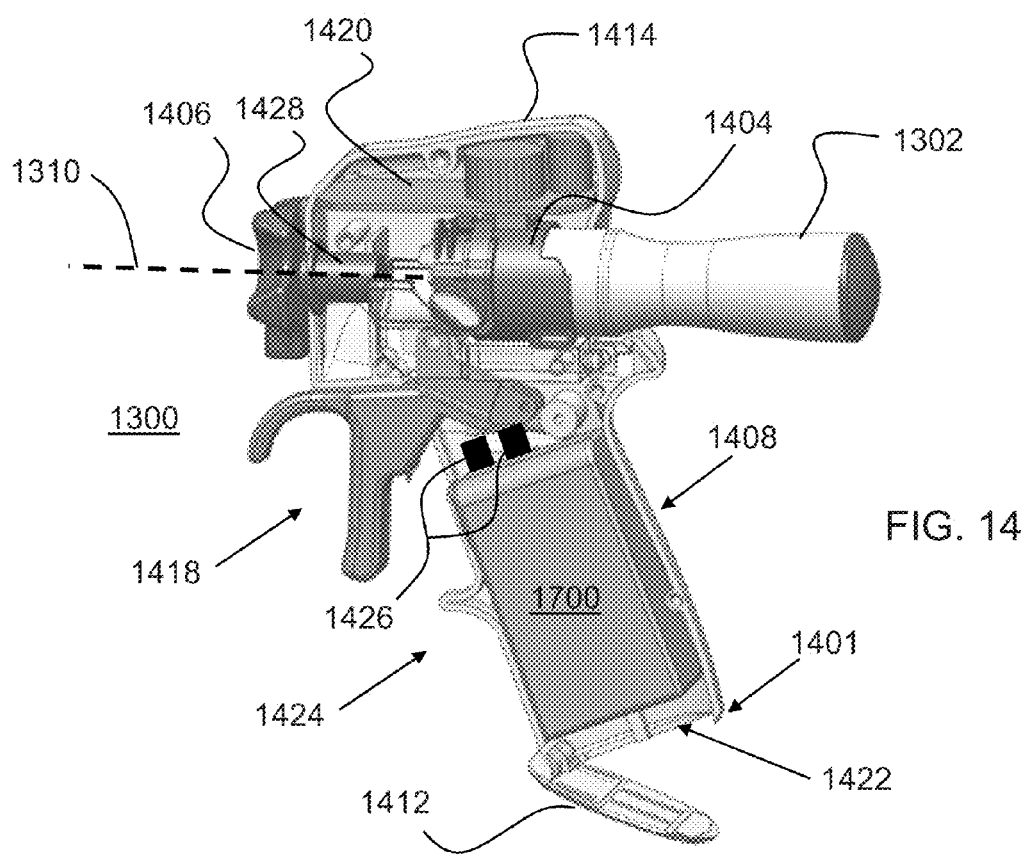
FIG. 14 is a side elevational view of the exemplary handle of FIG. 13 with the left-side shell removed and with the upper slide cover removed to show the integrated control, drive and matching components and removable power supply therein in accordance with an exemplary embodiment of the present invention.

As shown in FIG. 14, for example, the handle 1408 is also provided with a closable door 1412, for instance, at its bottom 1401. This provides a variety of possible assemblies. In one assembly, the gun body 1414, which includes the transducer coupling port 1404 and the triggering mechanisms 1418, is disposable and never used more than for a single surgery. This sub-assembly is generally the least expensive of all of the components of the device; in some cases, it is $1/100^{th}$ of the total cost of the device. The transducer 1302, which is much more expensive and is autoclavable, can be reused multiple times.

Figure 13:
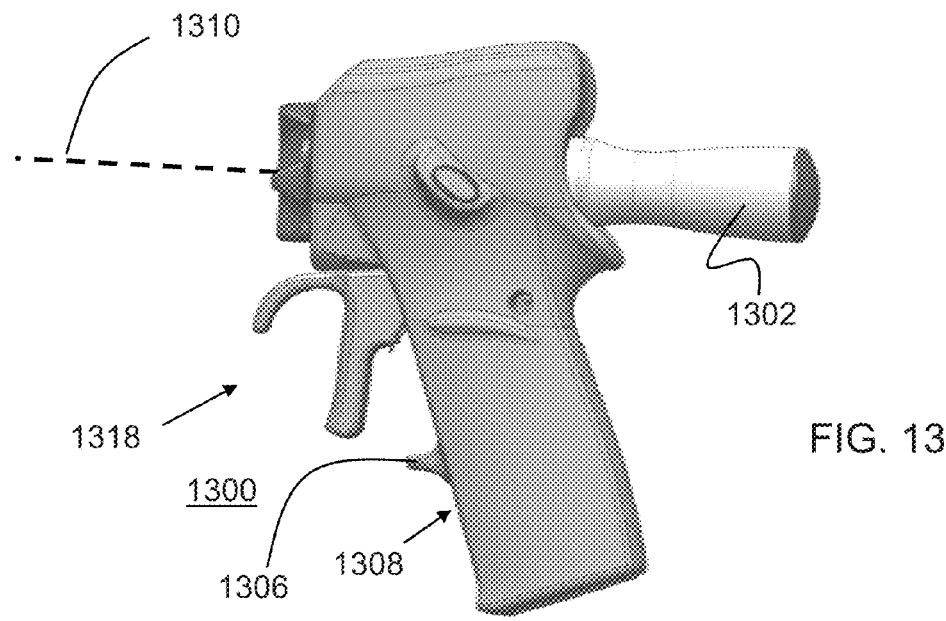
FIG. 13 is a side elevational view of a left side of an ultrasonic cutting device handle with fully integrated control, drive and matching components and removable transducer and power supply in accordance with an exemplary embodiment of the present invention.

An exemplary procedure for use of the device with the BAG 1700 is explained with regard to FIGS. 13 and 14. To start, a person in the sterile field opens a sealed package containing the new sterile gun body 1408 and removes it for use during the operation. The gun body 1408 can either already include the cannula 320 and waveguide 1310 (indicated with a dashed line) or can be coupled to a cannula 320 and waveguide 1310 after the package is opened. Next, the sterile (autoclaved) transducer assembly 1302 is inserted into the gun body 1408 and appropriately attached to the waveguide 1310. The surgeon then presents the underside of the gun body 1408 (with the door 1412 open) to the circulating nurse, who drops the BAG 1700 into the grip portion 1424 of the gun handle 1408 without contacting the exterior of the gun body 1408. Someone in the operating field (e.g., the surgeon) then closes the door 1412, thereby securing the non-sterile BAG 1700 within the gun 1300 through a sterile seal 1401 and preventing it from contaminating the sterile field. Because the removable BAG 1700 is sealed within the handle 1408, it is "outside" the sterile field during surgery.

Self-Contained Ultrasonic Device (SCUD)

Figure 18:
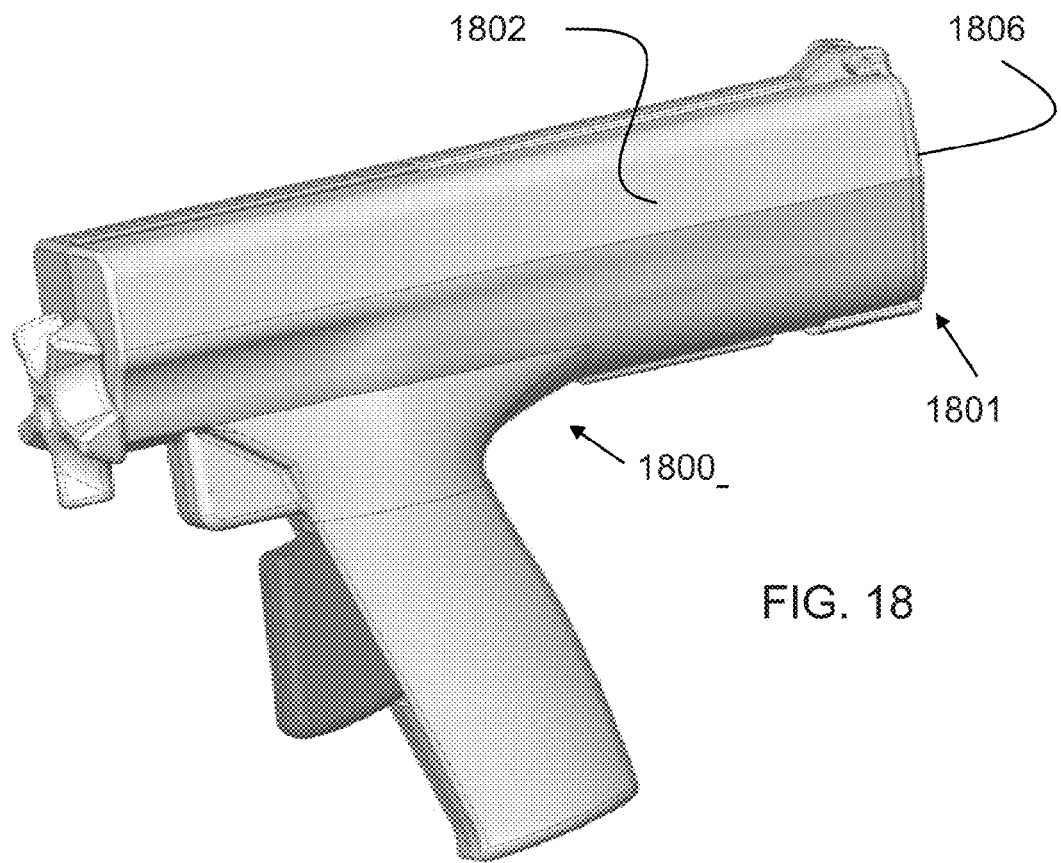
FIG. 18 is a side elevational view of a left side of an ultrasonic cutting device capable of holding in a top area a reusable pack that includes the battery, circuitry, and the transducer in accordance with an exemplary embodiment of the present invention.
Figure 19:
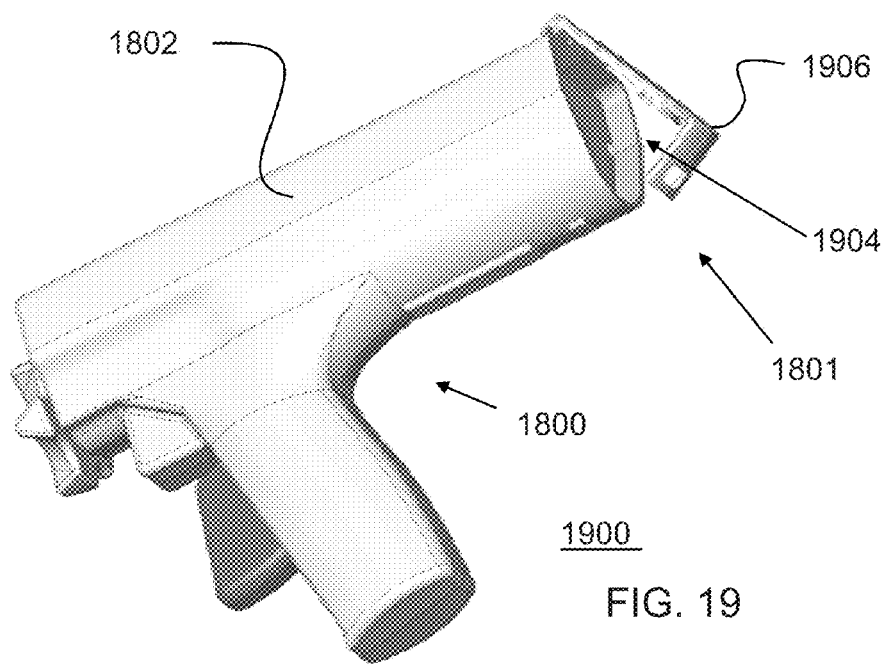
FIG. 19 is a side elevational view of a left side of the ultrasonic cutting device of FIG. 18 showing the access door in accordance with an exemplary embodiment of the present invention.

FIGS. 18 and 19 show yet another embodiment of the present invention in which the gun-shaped exterior body 1800 has a different shape than exterior body 1300 of FIGS. 13 and 14. The exterior body 1800 is shaped with a larger upper portion 1802. In this case, the generator, battery, and transducer are able to be inserted, either together as an assembly (referred to herein as an "ultrasonic-movement-generation assembly") or as separate components into a water-tight sealable cordless ultrasonic-movement-generation-assembly-holding compartment 1904 within the upper portion 1802 of the exterior body 1800. The interior of the compartment 1904 remains outside the sterile field during surgery with the aid of a sterile seal 1801. This insertion is performed through use of, as shown in FIG. 19, a door 1806, 1906 that can be opened and closed. When closed, the door 1806, 1906 seals the interior of the gun 1800 from the exterior environment of the gun 1800 and vice versa.

Figure 20:
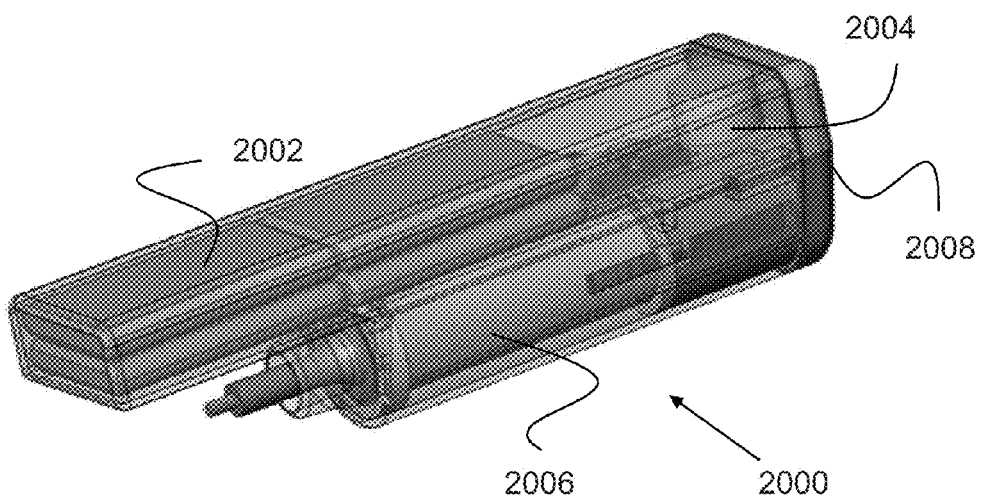
FIG. 20 is the removable, reusable pack used in the device shown in FIG. 18 and includes a battery, control circuit, drive circuit, matching circuit, and transducer.
Figure 21:
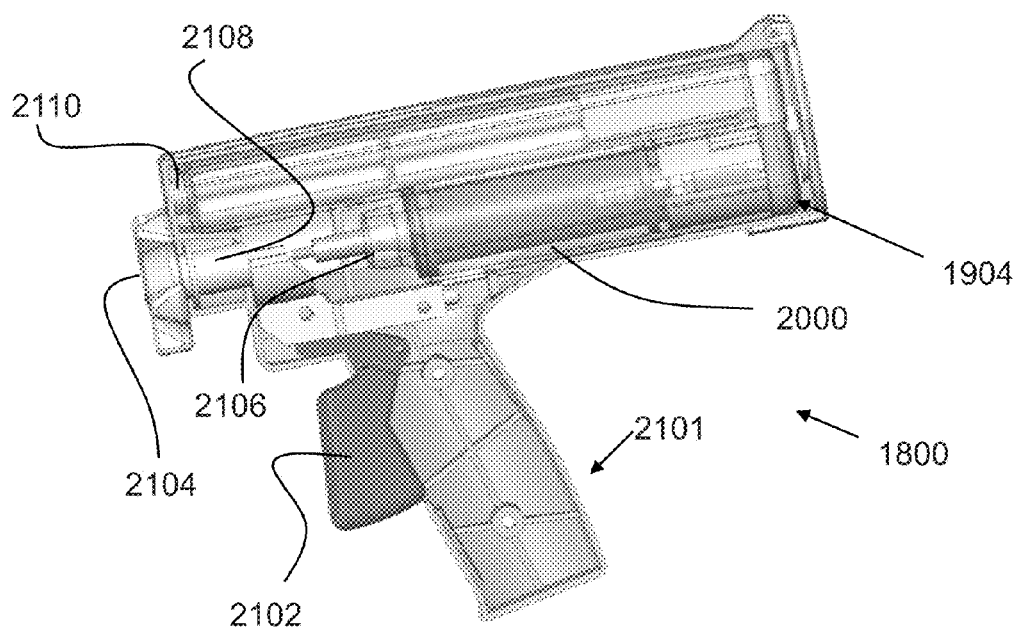
FIG. 21 is a side elevational view of a left side of an ultrasonic cutting device handle with fully integrated control, drive and matching components and removable power supply in accordance with an exemplary embodiment of the present invention.
Figure 22:
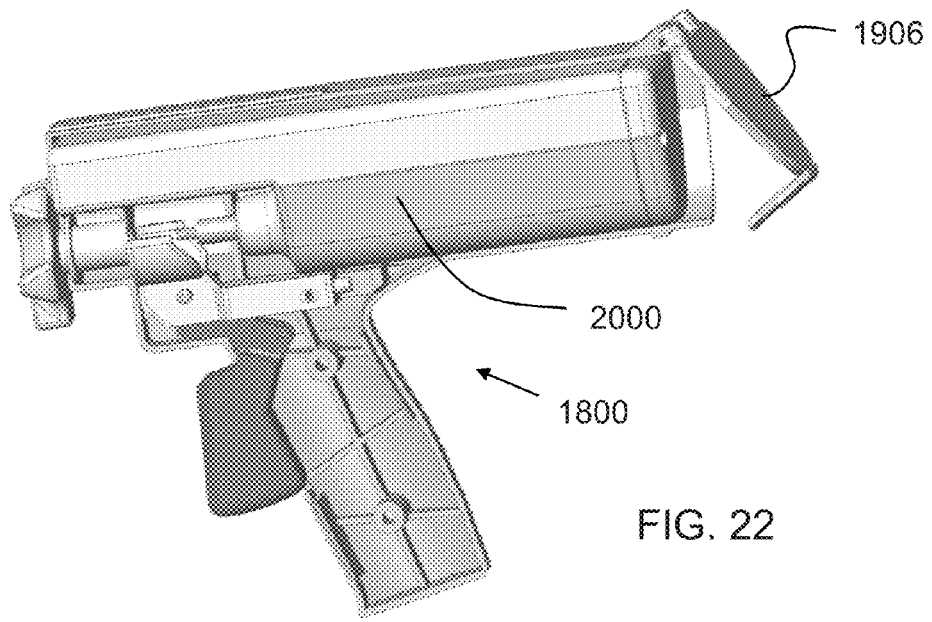
FIG. 22 is a side elevational view of the exemplary handle of FIG. 21 with the left-side shell removed and with the upper slide cover removed to show the integrated control, drive and matching components and removable power supply therein.

FIG. 20 shows an embodiment of the ultrasonic-movement-generation assembly 2000 that includes a battery 2002 (in this embodiment, similar to the embodiment of FIG. 17, the battery is a pack of batteries), a driving-wave generation circuit 2004 (i.e., generator), and a transducer 2006. The entire device 1900, shown in FIGS. 19, 21, and 22, is referred to herein as a Self-Contained Ultrasonic Device or "SCUD." The ultrasonic-movement-generation assembly 2000 can be easily inserted within the compartment 1904 of the disposable handle body 1800 and then sealed from the environment by the door 1806, 1906. Advantageously, in this exemplary embodiment, the ultrasonic-movement-generation assembly 2000, similar to the power source 1700, shown in FIG. 17, can be sterilized, but does not necessarily need to be sterile because it is shielded from the operating environment. This provides a tremendous advantage over prior art devices because the ultrasonic-movement-generation assembly 2000 and BAG 1700 do not have to be watertight or autoclavable. Without the requirements of being watertight and sterilizable, the electrical connectivity of the components can be easily and inexpensively obtained. For instance, when electrically connected components must be hermetically, or simply waterproof-sealed, the contacts need to be securely protected from moisture and from separation during the high temperature solutions to which they are exposed. For instance, leads would need to be soldered together or otherwise securely affixed to one another and wrapped with a protective coating to prevent rust/tarnishing and/or separation. This protective requirement is not present or at least not as stringent if the components can simply be slipped inside of an outer protective chamber, such as the handle of the ultrasonic gun 1300, 1800 of the present invention. These advantageous features reduce costs and failures, make troubleshooting much easier, and allow replacing or switching parts to be relatively simple. For instance, from time-to-time, a battery will "go bad" or not function properly. When a unit is fully sealed, opening it to replace the battery with another renders the device no longer hermetically sealed or, at a minimum, no longer reliably sealed. In contrast to such hermetically sealed devices, when the ultrasonic-movement-generation assembly 2000 (e.g., shown in FIG. 20) is made to be inserted into a sealed chamber, it can be configured to open easily and allow any component therein to be removed and exchanged as desired. Including all of the expensive components of the system in the reusable ultrasonic-movement-generation assembly 2000 allows for a simple and inexpensive design for the disposable ultrasonic gun portion of the system.

FIGS. 21 and 22 show the disposable handle body 1800 with the ultrasonic-movement-generation assembly 2000 inserted in the upper chamber 1904. The disposable handle body 1800 has a waveguide attachment dock 2104 disposed on an exterior of the body 1800, which is exposed to the environment and has a first couple 2108 operable to releasably physically couple a waveguide to the handle body 1800. The upper chamber 1904 is a water-tight, aseptically sealable, waveguide-movement-generation-assembly-holding compartment and has within its interior a waveguide-movement-generation assembly attachment dock 2106 that is operable to releasably physically couple the ultrasonic-movement-generation assembly 2000 to the handle 2101 and place the ultrasonic-movement-generation assembly 2000 in direct physical contact with an ultrasonic waveguide. The ultrasonic-movement-generation assembly 2000 is held in place by a door 1906 having an open position (shown in FIG. 22) that allows entry of the ultrasonic-movement-generation assembly 2000 into the chamber 1904 and removal of ultrasonic-movement-generation assembly 2000 from the chamber 1904. The door 1906 also has a closed position (shown in FIG. 21) that aseptically seals the interior from the exterior of the handle. In one exemplary embodiment, the chamber 1904 has a motion-generator-assembly ejector 2110 extending at least partially within the holding compartment 1904 and operable to activate (e.g., by movement of the door 1906 from the closed position to the open position) and at least partially eject the assembly 2000 from the holding compartment 1904.

Figure 25:
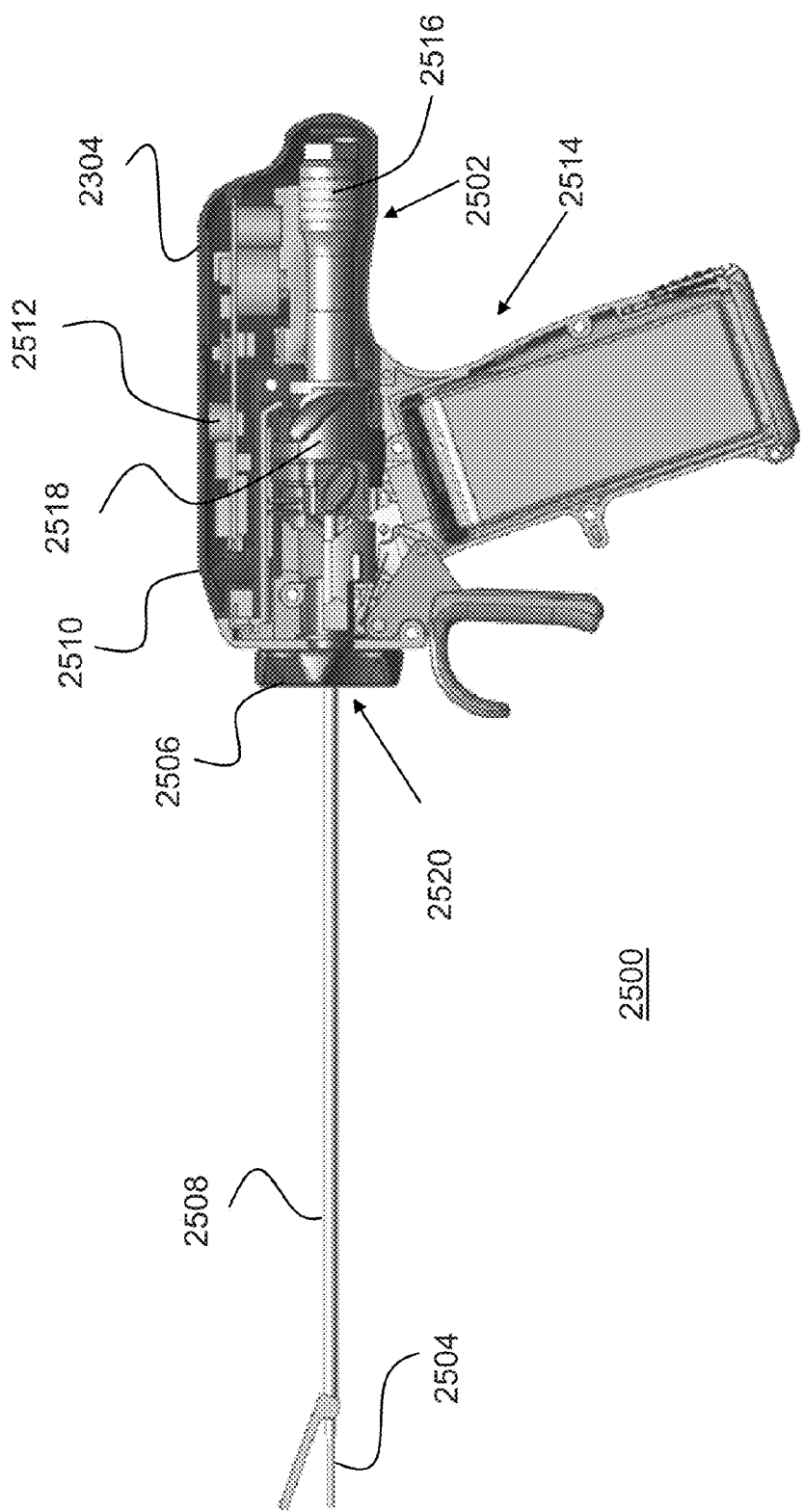
FIG. 25 is a side elevational view of an exemplary handle with the left-side shell removed to show a TAG, a removable power supply, and a blade and waveguide attached to the spindle in accordance with an exemplary embodiment of the present invention.

Once inserted, the gun 1800 is fully functional and ready to use with a waveguide (see, e.g., FIG. 25). The exemplary embodiment shown in FIGS. 18-22 allows the costliest portions of the gun to be reused as many times as desired and, advantageously, the portion of the device that is subject to fluids and other contaminates, i.e., the gun 1800, to be of low cost and disposed after the surgery.

Another advantage of a removable ultrasonic-movement-generation assembly 2000 or the BAG 1700 is realized when lithium-ion (Li) batteries are used. As previously stated herein, lithium batteries should not be charged in a parallel configuration of multiple cells. This is because, as the voltage increases in a particular cell, it begins to accept more charge faster than the other lower-voltage cells. Therefore, each cell must be monitored so that a charge to that cell can be controlled individually. When a lithium battery is formed from a group of cells, a multitude of wires extending from the exterior of the device to the battery 1702 is needed, at least one additional wire for each battery cell beyond the first. By having a removable ultrasonic-movement-generation assembly 2000 or BAG 1700, each battery cell can have its own exposed set of contacts and, when not present inside the device, each set of contacts can coupled to a corresponding set of contacts in an external, non-sterile battery-charging device.

Transducer-and-Generator Assembly (TAG)

FIGS. 23-30 and 42-45 show yet another exemplary embodiment 2300 of the present invention, which includes a disposable ultrasonic cutting tool handle 2301, a waveguide 2504, 2508, a waveguide-movement-generation assembly 2303, which includes the transducer and driving-wave generation circuit (generator shown in FIG. 24), and a battery 304. This embodiment, for ease of reference, is referred to herein as a Transducer-and-Generator assembly, or "TAG" 2300, which acronym refers to the contents of the removable waveguide-movement-generation assembly 2303.

The handle 2301 of the TAG 2300 includes a first handle body portion 2302 defining therein an aseptically sealable battery-holding compartment 2410 shaped to receive a removable battery 304 therein. The handle 2301 further includes a second handle body portion 2310 that is connected to, or integral with, the first handle body portion 2302. The second handle body portion 2310 has a waveguide attachment dock 2416 exposed to the environment and having a first couple 2418 operable to connect an ultrasonic waveguide 2504, 2508 thereto, as shown in FIG. 25. The handle 2301 also includes an ultrasonic-movement-generation assembly dock 4202 (shown in FIG. 42) exposed to the environment and shaped to connect the ultrasonic waveguide 2508 in the waveguide attachment dock 2418 to an ultrasonic-movement-generation assembly 2303 through the second handle body portion 2310. An electrical couple (such as couple 4106, shown in FIG. 41), connects the battery 304 within the battery-holding compartment 2410 to the ultrasonic-movement-generation assembly 2303 when the ultrasonic-movement-generation assembly 2303 is docked at the ultrasonic-movement-generation assembly dock 4202. As an alternative to this exemplary embodiment, the battery 304 can include part or all of the driving-wave generation circuit.

The removable ultrasonic-movement-generation assembly 2303 is a cordless (i.e., battery powered) assembly and has a selectively removable securing connector 4204 and an output couple 4206 operable to impart ultrasonic movement to the ultrasonic waveguide 2508 when the waveguide 2508 is connected thereto. The assembly 2303 includes a shell 2304, shown in FIG. 23, housing an ultrasonic generator 2404 and an ultrasonic transducer 2406, both shown in FIG. 24. The shell 2304 has a securing connection 4204 shaped to selectively removably connect to a first connector part 4208 of the ultrasonic surgical handle 2300, shown in FIG. 42. The connection 4204 can be a "dove-tail," as shown in the exemplary embodiment of the figures or any other coupling method that allows the ultrasonic-movement-generation assembly 2303 to be removably attached to the handle 2301. The transducer 2406 has an output couple 4206 operable to impart ultrasonic movement to an ultrasonic waveguide 2508 when the waveguide 2508 is connected thereto. In one embodiment, the output couple 4206 is a threaded connection that can be screwed onto or into a waveguide 2508. In addition, the ultrasonic-movement-generation assembly 2303 can be a sealed watertight and/or autoclavable assembly that can be used in a surgical procedure, sterilized, and then simply be coupled to a brand new handle 2300 to perform a second surgical procedure. As will be described, the TAG 2303 can take several different embodiments.

Figure 24:
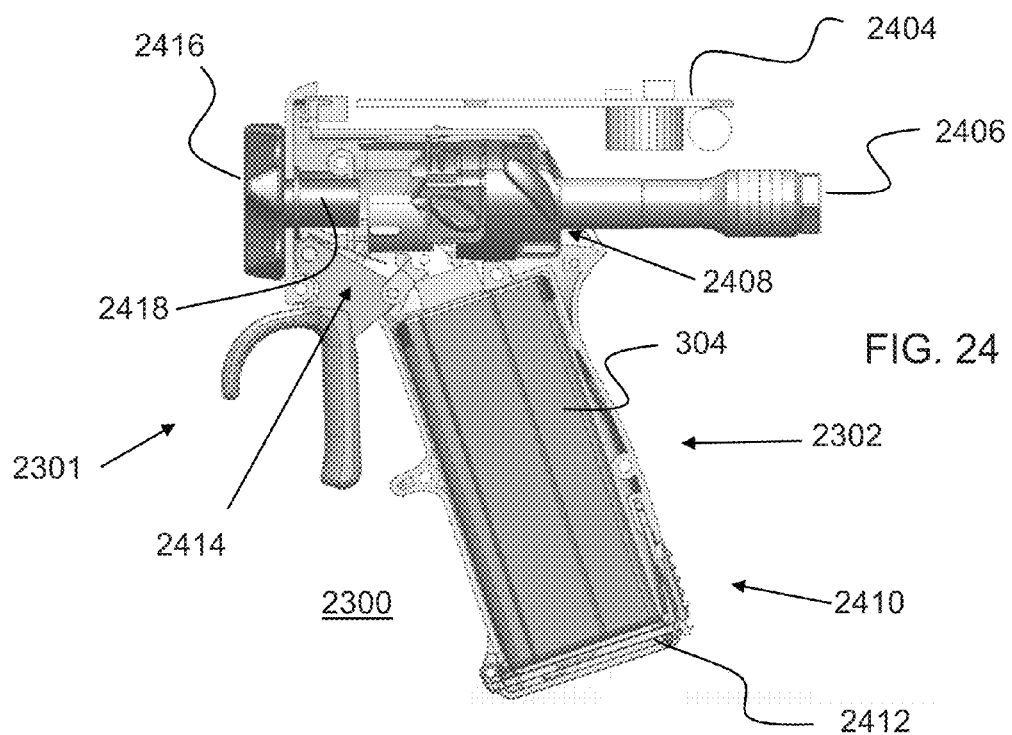
FIG. 24 is a side elevational view of the exemplary handle of FIG. 23 with the left-side shell removed and with the upper slide cover removed to show the integrated control, drive and matching components and removable power supply therein.

FIG. 24 is a cutaway view showing the interior of the TAG 2300 with the near-side (left side) cover of the handle 2301 and the shell 2304 of the ultrasonic-movement-generation assembly 2303 removed. Here, the power supply 304 (e.g., a battery) fits entirely within the first portion 2302 of the handle 2301. The cylindrical device 2406 shown in FIG. 24 is the transducer assembly, such as the transducer assembly 316 of FIG. 3. Located above the transducer assembly 2406 is the generator 2404. The two ultrasonic-movement-generation assembly components 2404, 2406, when placed inside the covering shell 2304, advantageously can be easily detached from the handle 2301 and sterilized or replaced as a complete unit. In one embodiment, the ultrasonic-movement-generation assembly components 2404, 2406 are hermetically sealed inside the cover 2304, rendering the ultrasonic-movement-generation assembly 2303 autoclavable so that it can be attached to and used with several different devices. The ultrasonic-movement-generation assembly 2303 is coupled to the second portion 2310 of the handle 2302 through a port 2408. The port 2408, when the ultrasonic-movement-generation assembly 2303 is removed, is visible and accessible from an exterior of the handle 2301. However, once the ultrasonic-movement-generation assembly 2303 is snapped onto the handle 2301, the handle 2301 and ultrasonic-movement-generation assembly 2303 could be shaped to create a water-tight seal with one another and prevent moisture on the exterior of either one of the handle 2302 and ultrasonic-movement-generation assembly 2303 from entering the junction between the handle 2301 and ultrasonic-movement-generation assembly 2303.

Figure 23:
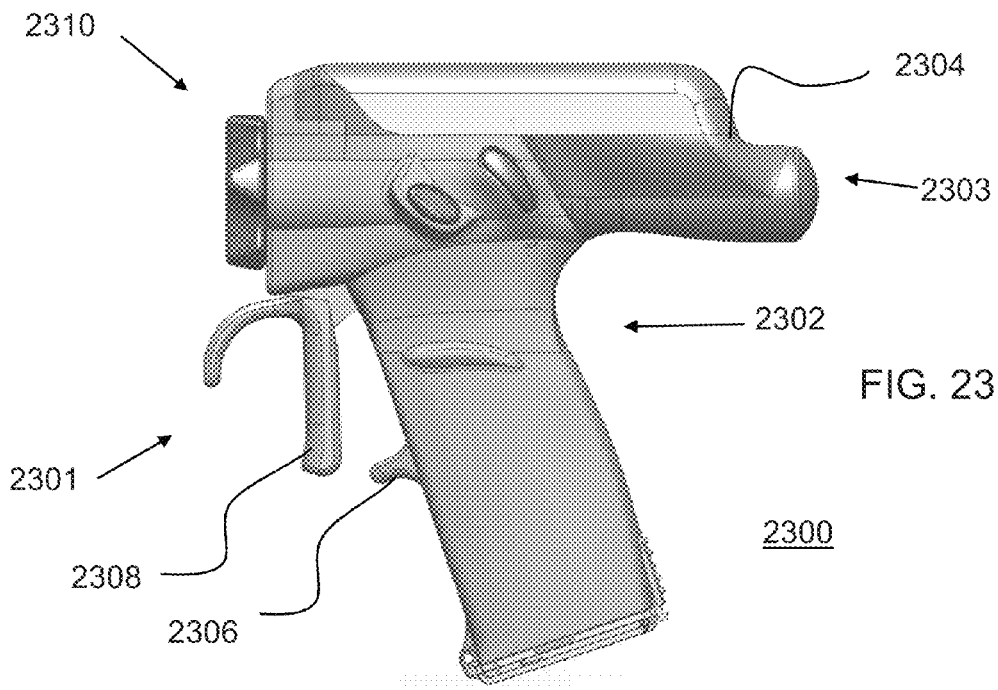
FIG. 23 is a side elevational view of a left side of an ultrasonic cutting device handle with fully integrated control, drive and matching components, and transducer in a removable module and also a removable battery pack in accordance with an exemplary embodiment of the present invention.

FIG. 24 also shows a battery door 2412 that, when opened, allows a battery 304 to be inserted into the battery-holding compartment 2410 and, when closed, as shown in FIG. 24, creates a water-tight seal (e.g., aseptic seal) between the interior of the handle 2302, shown in the cutaway view of FIG. 24, and the exterior of the handle 2302, shown in the elevational view of FIG. 23.

Once the ultrasonic-movement-generation assembly 2303 is coupled to the handle 2301, the driving-wave generation circuit, or "generator" 2404, is placed in electrical contact with the battery-holding compartment 2410 so that a battery 304, when inserted, can supply power to the ultrasonic-movement-generation assembly 2303. Additionally, referring now to FIG. 25, when an ultrasonic-movement-generation assembly 2502 is coupled to a handle 2514, the transducer 2516 is caused to be releasably physically coupled to a waveguide 2504, 2508 through the transducer attachment port 2518 and waveguide attachment port 2520. It is envisioned that the transducer assembly 2516 can be temporarily locked into a fixed rotational position so that the waveguide 2504 can be attached to the threads 1610 (see, e.g., FIG. 16) with sufficient force. This physical coupling between the waveguide 2504 and the transducer assembly 2516 allows the transducer assembly 2516 to impart movement to the waveguide 2504 when power is applied to the transducer assembly 2516.

The gun 2500 has a spindle 2506 that attaches to the waveguide 2508. The spindle 2506 has indentions that allow a surgeon to easily rotate the spindle 2506 and, therefore, the attached waveguide 2508 and transducer assembly 2516 that is attached to the waveguide 2508. Such a configuration is useful for obtaining the proper cutting-blade angle during surgery. To provide for this rotation, in one exemplary embodiment, the transducer assembly 2516 is able to rotate freely within the transducer housing 2510.

During initial coupling of the transducer assembly 2516 and waveguide 2504, all that is needed is that one of the transducer assembly 2516 and the waveguide 2504 remains relatively stationary with respect to the other. According to one exemplary embodiment of the present invention, when the transducer assembly 2516 is located inside the housing 2510—where it cannot be readily secured by the operator, for example, by holding it steady by hand when the waveguide 2508 is being secured—the ultrasonic-movement-generation assembly 2502 is provided with a button (not shown) that slides into a recess in the housing 2510 or, alternatively, by fixing the rotation of the transducer assembly 2516 at a maximum rotational angle so that, once the maximum rotation is reached, for example, 360 degrees of rotation, no additional rotation is possible and the waveguide 2504 can be screwed thereon. Of course, a maximum rotation in the opposite direction will allow the waveguide 2504 to be removed as well.

Figure 26:
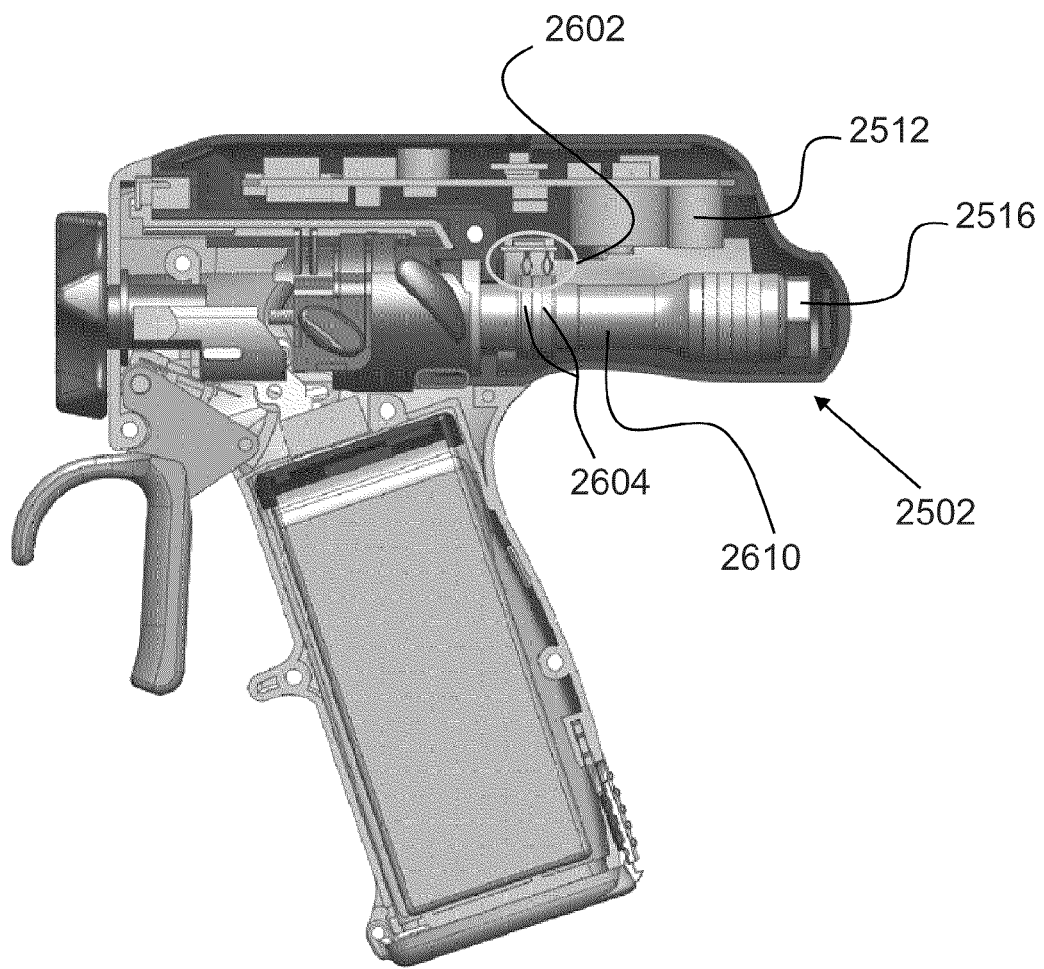
FIG. 26 is a side elevational view of an exemplary handle with the left-side shell removed to show electronic coupling between the generator and transducer assembly of the TAG in accordance with an exemplary embodiment of the present invention.
Figure 27:
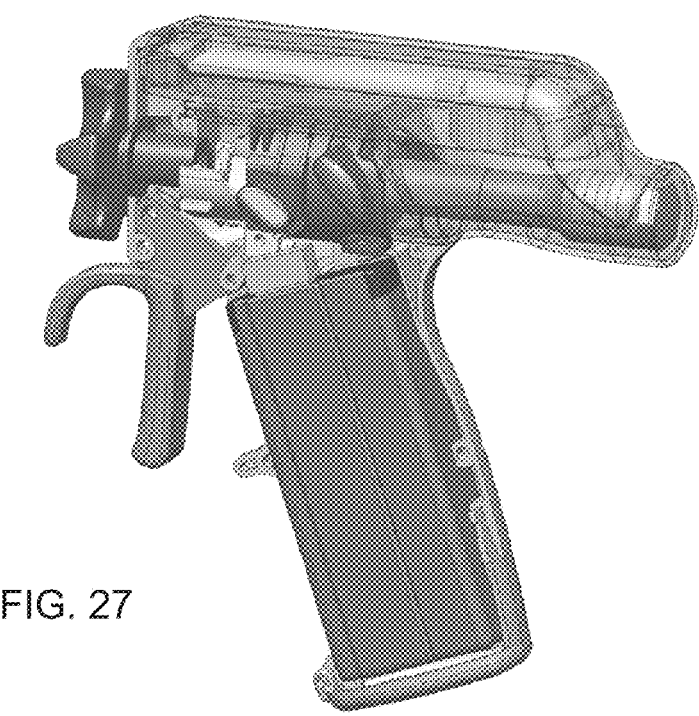
FIG. 27 is an enlarged side elevational view of the exemplary handle of FIG. 23 from the left side thereof with the left-side shell, the slide cover, and the battery pack removed, and with the trigger in an intermediate actuated position.
Figure 28:
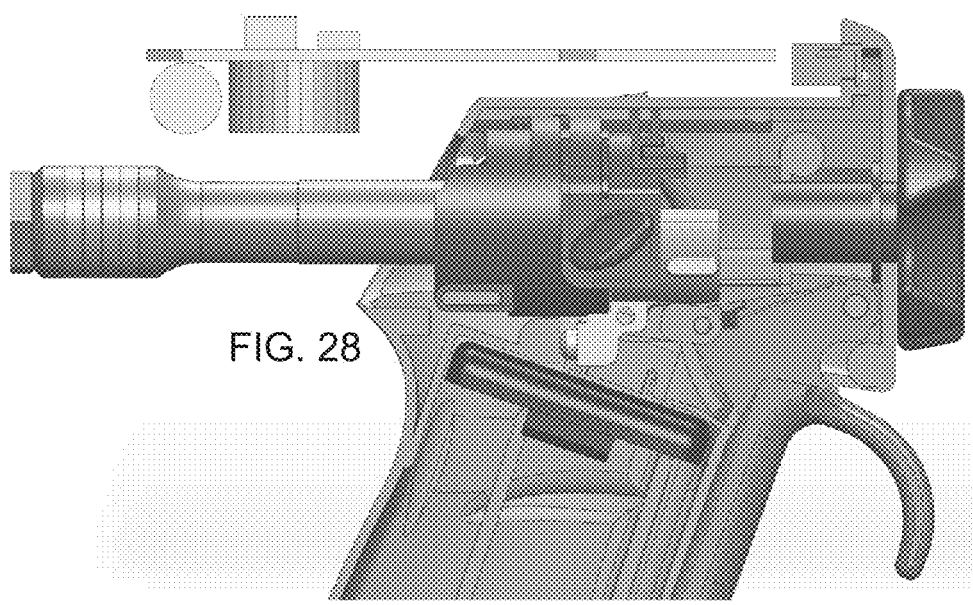
FIG. 28 is an enlarged side elevational view of the exemplary handle of FIG. 23 from the right side thereof with the right-side shell, the slide cover, and the battery pack removed, and with the trigger in a fully actuated position.
Figure 29:
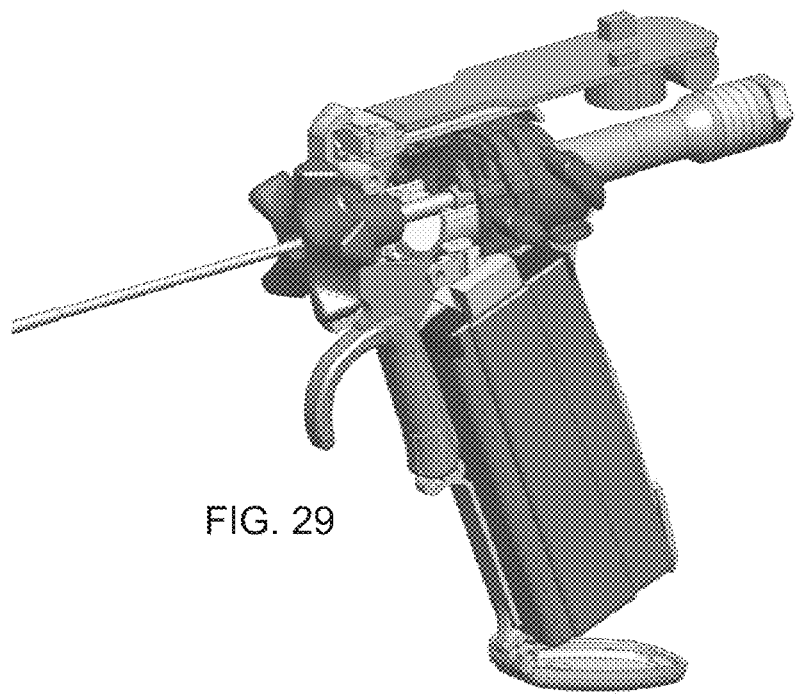
FIG. 29 is an enlarged side elevational view of the exemplary handle of FIG. 23 from the left side thereof with the shell and left-side slide cover removed.
Figure 30:
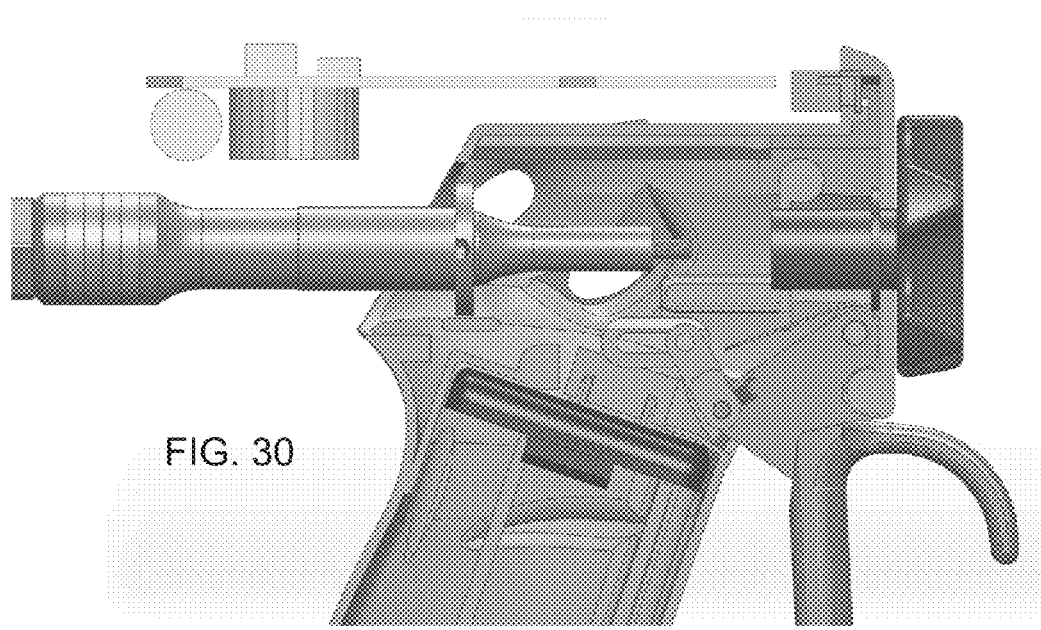
FIG. 30 is an enlarged side elevational view of the exemplary handle of FIG. 29 from the right side thereof also with internal trigger components removed.
Figure 31:
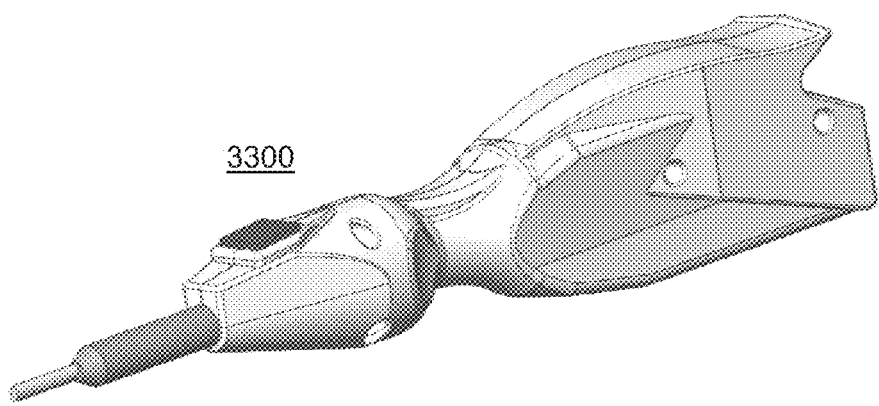
FIG. 31 is a perspective view from the front left side of a hand-held ultrasonic cutting pen device with fully integrated control, drive and matching components and removable power supply in accordance with an exemplary embodiment of the present invention.
Figure 32:
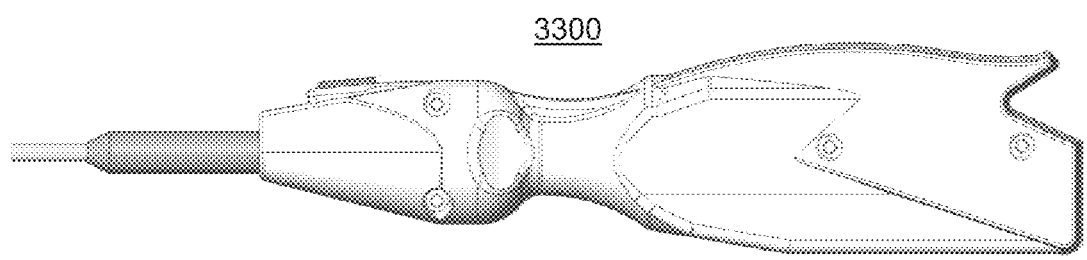
FIG. 32 is a side elevational view of the hand-held ultrasonic cutting pen device of FIG. 21 from the left side.
Figure 33:
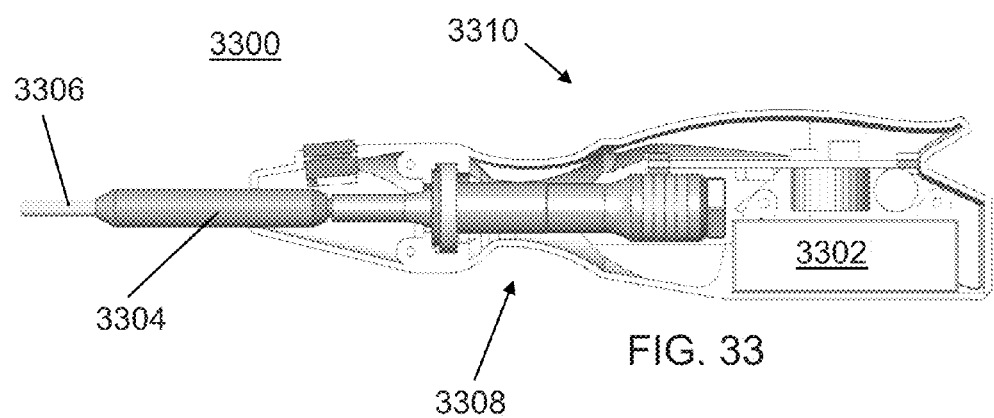
FIG. 33 is a side elevational view of the hand-held ultrasonic cutting pen device of FIG. 32 with the left-side shell removed.

FIG. 26 shows one example of how the generator assembly 2512 and transducer assembly 2516 are electrically coupled so that a physical rotation of the transducer assembly 2516 with respect to the generator assembly 2512 is possible. In this example, the generator assembly 2512 has a pair of contacts 2602 protruding from its underside, adjacent the transducer assembly 2516. Proximity of the transducer assembly 2516 to the generator assembly 2512 places one of the pair of contacts 2602 (circled) in physical communication with a pair of contact rings 2604 at the transducer body 2610 so that a driving signal can be steadily applied to the transducer assembly 2516 when needed. Advantageously, the pair of contacts 2602 maintains electrical contact regardless of an angle of rotation of the transducer assembly 2516. Therefore, the transducer assembly 2516 can rotate without any limitations as to the maximum angle or number of rotations. In one embodiment of the present invention, the waveguide-movement-generation assembly 2303 can include a battery 304.

This embodiment is advantageous, as it allows the handle portion 2302 to be made smaller or cheaper, as battery contacts are not necessary in the handle portion 2302.

Transducer

In another non-illustrated embodiment, the cover 2304 is not present and the transducer assembly 2516 and generator assembly 2512 assemblies are individually covered, i.e., sealed and autoclavable, with each cover being exposed and accessible to a user's fingers. With the main cover 2304 not present, an operator attaching the transducer assembly 2516 to the waveguide 2508 has direct access to the transducer assembly 2516 and is able to hold both the transducer assembly 2516 and the waveguide 2508 and turn either one relative to the other during coupling.

FIGS. 27-30 show more detailed views of exemplary embodiments of the device and the trigger mechanisms. It is noted that there is a difference between the activation trigger of the device shown in FIGS. 19-22 and the trigger shown in FIGS. 23-30. Specifically, in the device 1800 of FIGS. 19-22, and shown more particularly in FIG. 21, the upper handle portion 1802 is hollow. Because it is hollow, the trigger 2102 can be a thick object that, when squeezed, is able to retract at least partially into the interior of the handle 2101. The thick trigger 2102 has the advantage of preventing a user's fingers from getting pinched when the trigger 2102 is squeezed. In contrast to this embodiment, the embodiment of FIG. 24 includes a battery 304 within the interior of the hand grip 2302. Because the interior of the hand grip 2302 is filled with the battery 304, the trigger 2308 cannot retreat inside the hand grip 2302 when actuated, as does the trigger 2102 of FIG. 21. For this reason, the trigger 2308 is thinner than the trigger 2102 of FIG. 21 in the trigger actuation direction and simply moves toward the hand grip 2302 during actuation (it does not enter the interior of the hand grip 2302, or enters it only minimally).

Advantageously, to prevent a user's finger from getting caught between the trigger 1318, 1418, 2308 and the hand grip 1308, 1408, 2302, the trigger includes a protrusion 1306, 2306 extending from the hand grip 1308, 2302 and preventing the user's finger from moving up and under the trigger 1318, 2308. Not only does the protrusion 1306, 2306 prevent the user's finger from getting pinched and causing possible discomfort, the protrusion 1306, 2306 also prevents the user's finger from interfering with functioning of the trigger 1318, 2308.

In an alternative exemplary embodiment to the gun device, FIGS. 31 to 34 illustrate an entirely hand-held and fully self-contained cautery and cutting device 3300. This cutting device 3300 reduces the size of the power supply 3302 considerably. Here, in comparison to the previous embodiments, the waveguide 3304 is reduced in length. All of the power modification components (the control, drive, and matching circuits 304, 306, 308) and the power supply 3302 reside at the handpiece 3310. As in the other embodiments described above, the pen shaped device shown in FIGS. 31 to 34 could have, in accordance with one embodiment, a sealed body 3302, where the body 3302 housing the power modification components (the control, drive, and matching circuits 304, 306, 308) and the power supply 3302 is autoclavable and the waveguide 3304 is simply replaced for each procedure. Alternatively, the body 3102 could open up and receive the power modification components (the control, drive, and matching circuits 304, 306, 308) and the power supply 3302 in an aseptic transfer, similar to the device shown in FIG. 21 and described above.

In further exemplary embodiments of the present invention, the power supply can be separated from the handpiece and can, for example, be worn on a physician's belt. An example of such embodiments can be seen in FIGS. 34 to 38. In these embodiments, the base 3700, shown in FIG. 37, has a body 3706 that houses a self-contained power source (i.e., a battery) and a generator circuit operable to generate an output waveform and is sized to be handheld. The base 3700 is connected through a communications and power tether cord 3702, illustrated diagrammatically in the figures with a dashed line, to the pen-shaped ultrasonic waveguide handle 3600, shown in FIGS. 34-36. When in operation, the transducer 3602 within the handle 3600 is driven by a plurality of driving waves output from the waveform generator within the body 3706.

The base 3700 has a user interface 3704 that can be used to communicate data and carry out functions of the device, such as testing and operation. Through the user interface 3704, the device can be tested in the sealed package without even opening the package. For instance, in one embodiment, a user can press one or more non-illustrated buttons (physical or electronic) in a given sequence (e.g., 5 times in a row) and, thereby, cause the user interface 3704 to display a status of the battery and/or a status of the logic circuitry, all without having to remove it from the sealed package. This is helpful in case of a defect, such as a bad battery, as the purchaser would be able to return the device to the manufacturer before use and, thereby, prove non-use of the device to receive credit. In this embodiment, all of the power modification components (the power supply 304, the processor 302, the drive circuit 308, and the matching circuit 312) reside in the base 3700.

The base 3700 is also provided with a non-illustrated clothing attachment mechanism that can be a simple belt clip, or any other way of attaching a device to a wearer. The clothing attachment mechanism allows a surgeon or nurse to wear the base 3700 during a surgery so that the cord 3702 will always be of sufficient length, i.e., as long as his arm can reach, no matter where the surgeon is standing.

Figure 34:
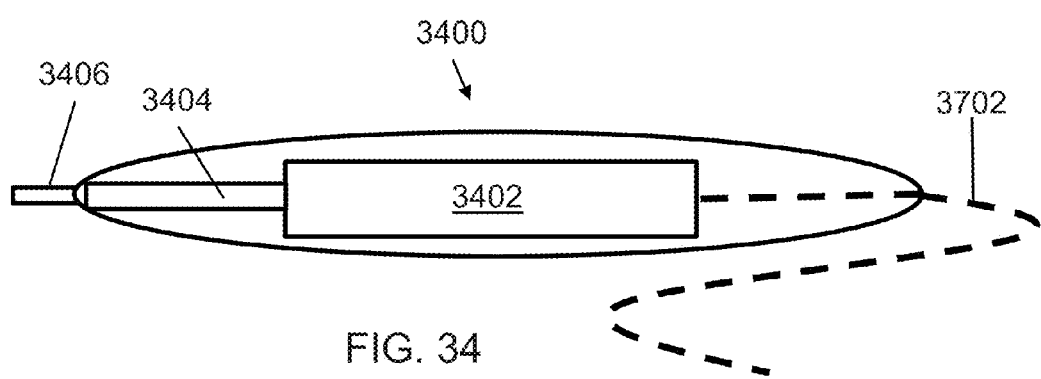
FIG. 34 is a diagrammatic illustration of a hand-held ultrasonic cutting pen device to be connected to a man-portable, control and power supply assembly in accordance with an exemplary embodiment of the present invention.
Figure 35:
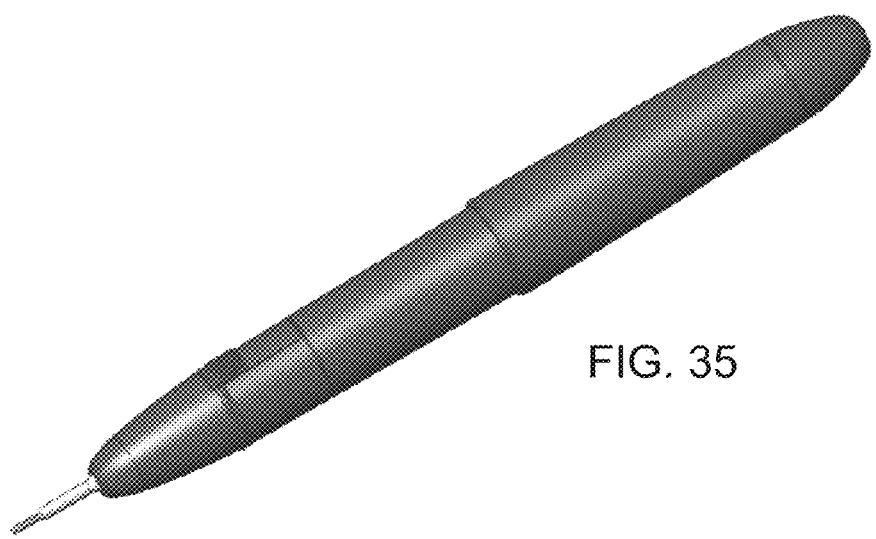
FIG. 35 is a perspective view of a hand-held ultrasonic cutting pen device to be connected to a man-portable, control and power supply assembly in accordance with an exemplary embodiment of the present invention.
Figure 36:
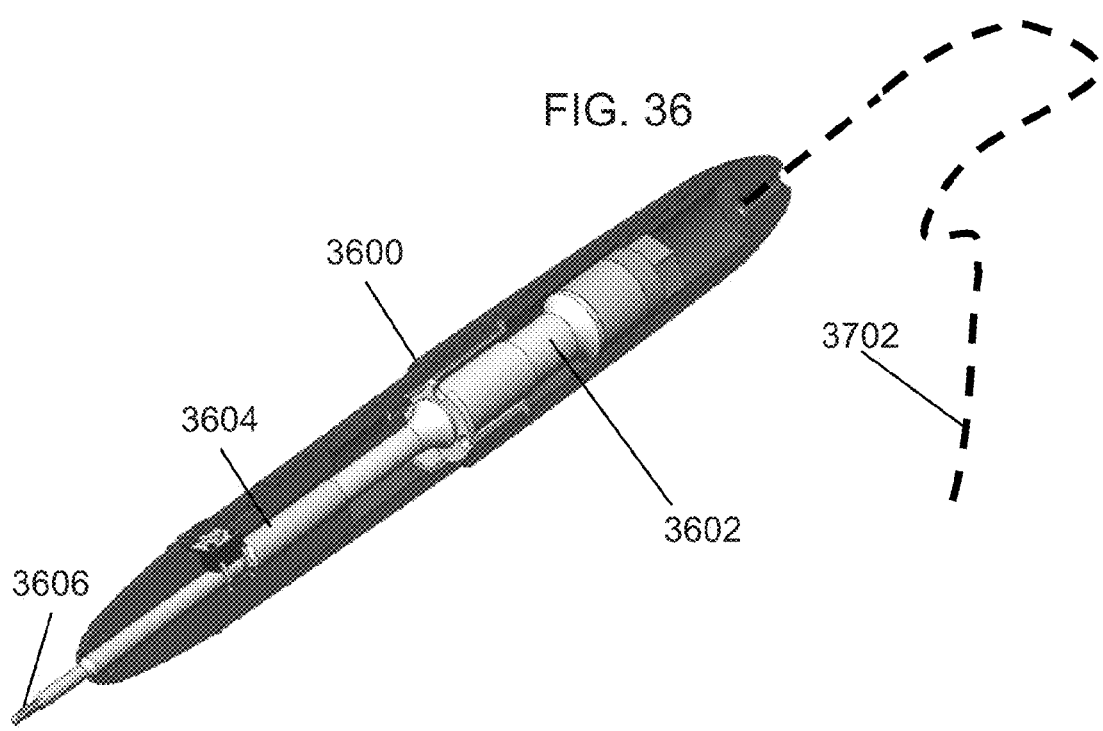
FIG. 36 is a perspective view of the hand-held ultrasonic cutting pen device of FIG. 35 with a left-half shell removed.
Figure 37:
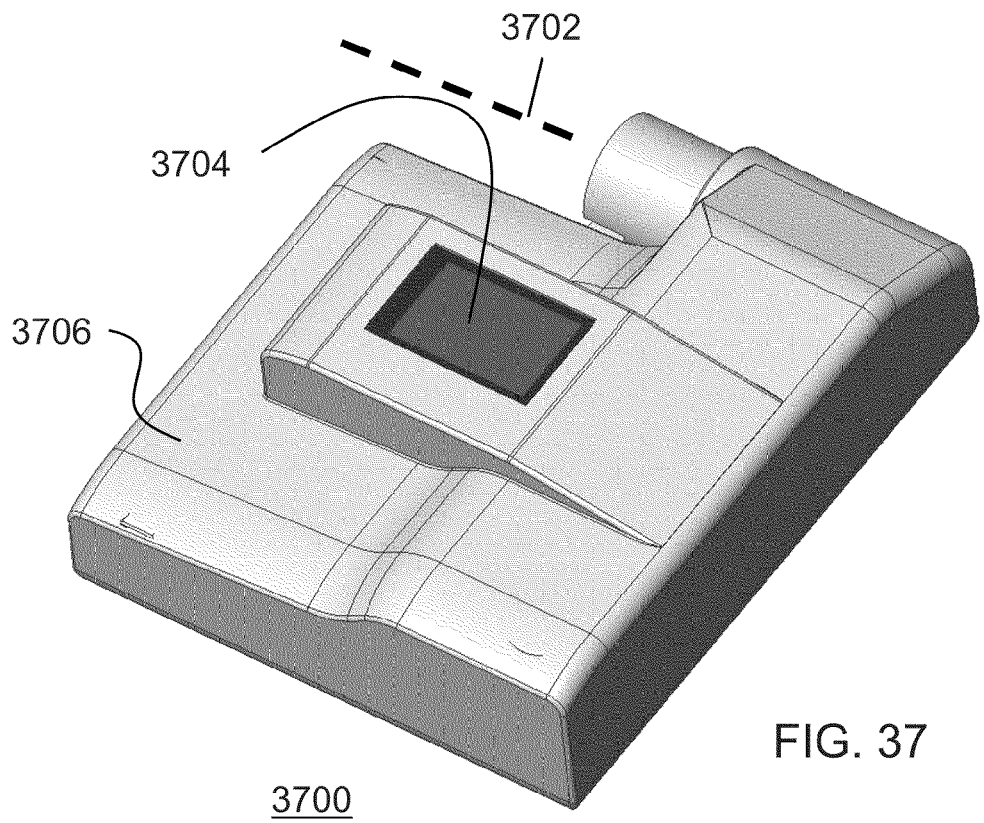
FIG. 37 is a perspective view of a man-portable, control and power supply assembly to be connected to a hand-held ultrasonic cutting pen device in accordance with an exemplary embodiment of the present invention.
Figure 38:
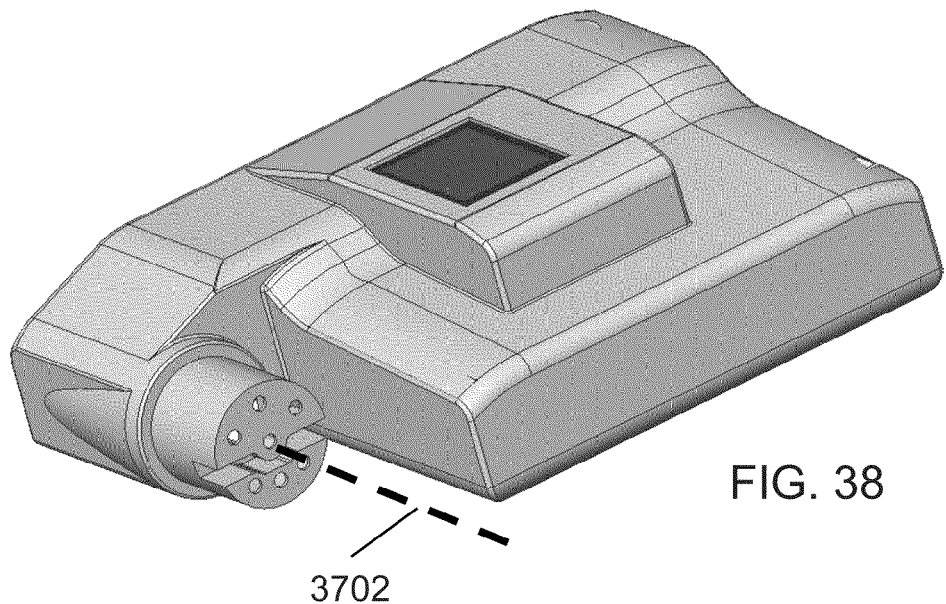
FIG. 38 is a different perspective view of the man-portable, control and power supply assembly of FIG. 37.

For ease of use, the cautery/cutting device 3400 is shaped to fit into a surgeon's hand. The shape illustrated in FIG. 34 is, therefore, only exemplary. Another exemplary shape for the pen device 3600 is shown in FIGS. 35 and 36 and is similar to a writing pen so that the surgery can be carried out with the device 3600 to approximate writing—a process that is comfortable to most physicians. The pen 3400, 3600 includes all of the transducer components—the transducer 3402, 3602, the protective cannula 3404, 3604, and the waveguide 3406, 3606.

In various other embodiments of the present invention, one or more of the components, together or separate, can be removed from or exchanged between the handpiece 2300, 3300, 3400, 3600 and the base 3700 for service, replacement, storage, inspection, or other purposes as desired.

The component(s) of the devices described herein (whether separately, as a unit, or a frame to which they are connected to one another) can implement a confirmation process for ensuring that the various component(s) can or should be used in or with the device. For instance, the components can perform a check (possibly with encryption) to see whether they match the particular handpiece 2300, 3300, 3400, 3600 or base 3700, i.e., to see if they have the correct manufacturer/model number to work with the part in which or to which it is connected.

In an exemplary safety embodiment for any of the configurations of the invention, the system can have a safety mechanism where the surgeon using the device is grounded to the circuit 300. In the event the waveguide 318, 3306, 3406, 3606 accidentally makes contact with the surgeon, the device senses this grounding and immediately ceases movement of the waveguide 318, 3306, 3406, 3606, thereby instantly preventing the surgeon from cutting him/herself. Because the hand-held instrument 2300, 3300, 3400, 3600, 3700 is not connected to earth ground, it will be possible to provide a safety circuit that can sense contact with the surgeon and interrupt ultrasonic power delivery. For example, a capacitive contact patch located on the hand grip 2302, 3310, 3400, 3600, 3700 is connected to a capacitive-touch sensing circuit (such as is used for capacitive switching and known to those in the art) and disposed to detect contact of the working tip with the surgeon. When such contact is detected, the drive circuit of the instrument will be shut down to avoid applying cutting energy to the surgeon. Such a sensing circuit would be impractical in systems of the prior art, where the handpiece is connected to a large piece of earth-grounded electrical equipment.

Figure 39:
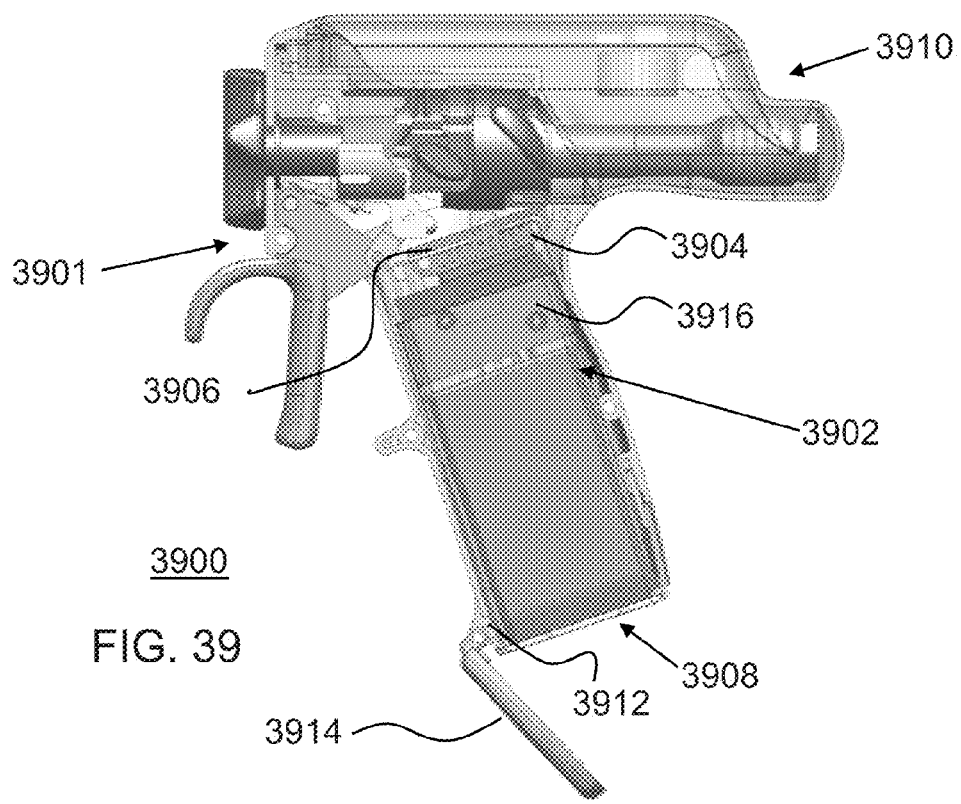
FIG. 39 is a side elevational view of an exemplary handle with the left-side and upper shell removed to show a waveguide-movement-generation assembly and a smart battery in accordance with an exemplary embodiment of the present invention.

FIG. 39 shows another exemplary embodiment of the present invention, which includes a "smart" or "intelligent" battery 3902. The smart battery 3902 is used to power a surgical or other device, such as the gun 3900. However, the smart battery 3902 is not limited to the gun 3900 and, as will be explained, can be used in a variety of devices, which may or may not have power (i.e., current and voltage) requirements that vary from each other. The smart battery 3902 is advantageously able to identify the particular device to which it is electrically coupled. It does this through encrypted or unencrypted identification methods. For instance, the battery 3902 can have a connection portion, such as portion 3904 shown in FIG. 39. The gun's handle 3901 can also be provided with a device identifier 3906 communicatively coupled to the battery-holding compartment 3908 and operable to communicate at least one piece of information about the handle 3901. This information can pertain to the number of times the handle 3901 has been used, the number of times a TAG unit 3910 has been used, the number of times a waveguide (not shown) has been used, the type of waveguide connected to the handle 3901, the type or identity of TAG 3910 connected to the handle 3901, or many other characteristics. When the battery 3902 is inserted in the handle 3901, the connection portion 3904 makes communicating contact with the device identifier 3906. The handle 3910, through hardware, software, or a combination thereof, is able to transmit information to the smart battery assembly 3902. This communicated identifier is received by the connection portion 3904 of the smart battery assembly 3902.

In one embodiment, once the smart battery assembly 3902 receives the information, the communication portion 3904 is operable to control the output of the battery assembly 3902 to comply with the device's specific power requirements. By integrating a microcontroller 3916 in the communication portion 3904 of the battery assembly 3902, it is no longer required that a programmable device be placed in the disposable handle portion 3901. As a result, the handle may be sterilized by gamma radiation, which is more economical than other sterilization measures.

In accordance with another embodiment, the battery-holding compartment 3908 has a battery ejector device 3912 that extends at least partially within the battery-holding compartment 3908 and is able to cause at least a portion of the battery 3902 to be ejected from the battery-holding compartment 3908. This prevents an operator from having to reach his or her potentially soiled or otherwise non-sterile fingers inside the device in order to remove the battery assembly 3902. In one embodiment, the battery-holding compartment 3908 is activated by a movement of the door from the closed position to the open position. In other words, once the door is opened, the battery 3902 partially ejects out of the compartment 3908.

In some exemplary embodiments of the present invention, the transducer assembly 1302, shown in FIG. 15, contains additional circuit components, such as the tank circuit 312 shown in FIG. 3. In practice, the tank circuit 312 is tuned to match the transducer to which it feeds. Therefore, transducers and tank circuits are best matched if they remain as a pair and are not placed in combination with other device. In addition, if each transducer assembly 1302 had its own tank circuit, the smart battery 3902 could feed different frequencies to the different transducer assemblies 1302, the frequencies being respectively matched to a particular blade and waveguide assembly. Two popular frequencies for ultrasonic surgery devices are 55 kHz and 40 kHz.

In one exemplary embodiment, the communication portion 3904 includes a processor, such as processor 302, and a memory, such as memory 326, which may be separate or a single component. The processor 302, in combination with the memory 326, is able to provide intelligent power management for the gun device 3900. This embodiment is particularly advantageous because an ultrasonic device, such as device 300, has a power requirement (frequency, current, and voltage) that may be unique to the device 300. In fact, device 300 may have a particular power requirement or limitation for one dimension or type of waveguide 318 and a second different power requirement for a second type of waveguide having a different dimension, shape, and/or configuration.

If a set of different devices having different waveguides exists, then each of the waveguides would have a respective maximum allowable power limit. Exceeding the power limit overstresses the waveguide and eventually causes it to fracture. One waveguide from the set of waveguides will naturally have the smallest maximum power tolerance. Because the prior-art batteries lack intelligent battery power management, the output of prior-art batteries must be limited by a value of the smallest maximum allowable power input for the smallest/thinnest/most frail waveguide in the set that is envisioned to be used with the device/battery. This would be true even though larger, thicker waveguides could later be attached to that handle and, by definition, allow a greater force to be applied.

This limitation is also true for maximum battery power. If one battery is designed to be used in multiple devices, its maximum output power will be limited to the lowest maximum power rating of any of the devices in which it is to be used. With such a configuration, one or more devices or device configurations would not be able to maximize use of the battery because the battery does not know the device's limits.

In contrast thereto, exemplary embodiments of the present invention utilizing the smart battery 3902 are able to intelligently circumvent any previous limitation of ultrasonic devices. The smart battery 3902 can produce one output for one device or a particular device configuration and the same battery 3902 can later produce a different output for a second device or device configuration. This universal smart battery surgical system lends itself well to the modern operating room where space and time are at a premium. By having a single battery pack that operates many different devices, the nurses can easily manage the storage and retrieval of the packs. Advantageously, the smart battery system requires only one type of charging station, thus increasing ease and efficiency of use and decreasing cost.

In addition, other devices, such as an electric stapler, may have a completely different power requirement than that of the ultrasonic device 300. With the present invention, a single smart battery 3902 can be used with any one of an entire series of devices and is able to tailor its own power output to the particular device in which it is installed. In one embodiment, this power tailoring is performed by controlling the duty cycle of a switched mode power supply, such as buck, buck-boost, boost, or other configuration, integral with or otherwise coupled to and controlled by the smart battery 3902.

In other exemplary embodiments, the smart battery 3902 can dynamically change its power output during device operation. For instance, in vessel sealing devices, power management is very important. In these devices, large constant current values are needed. The total power output needs to be adjusted dynamically because, as the tissue is sealed, its impedance changes. Embodiments of the present invention provide the smart battery 3902 with a variable maximum current limit. The current limit can vary from one application (or device) to another, based on the requirements of the application or device.

Figure 44:
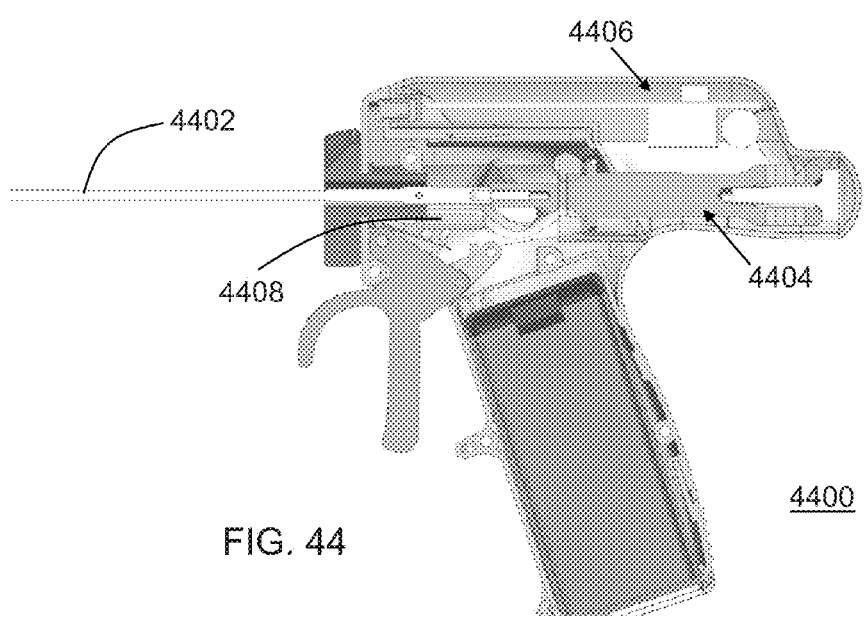
FIG. 44 is a side elevational cutaway view of the exemplary handle of FIG. 25 with the left-side shell removed to show connection details between the waveguide and waveguide-movement-generation assembly in accordance with an exemplary embodiment of the present invention.

More specifically, referring to FIG. 44, an ultrasonic surgical device 4400 has an ultrasonic waveguide 4402 with one of a set of different waveguide types. An ultrasonic transducer 4404 is physically coupled to the waveguide 4402 and is operable to impart ultrasonic movement to the ultrasonic waveguide 4402. A cordless ultrasonic-movement-generation assembly 4406 is connected to either the waveguide or the transducer and is operable to generate and deliver a driving-wave frequency and a driving-wave power to the transducer 4404. Because the device 4400 is able to accept and drive waveguides 4402 of varying dimensions, the device 4400 is provided with a waveguide detector 4408 coupled to the ultrasonic-movement-generation assembly 4406 and operable to detect the type (e.g., the dimensions) of the waveguide 4402 attached to the transducer 4404 and to cause the ultrasonic-movement-generation 4406 assembly to vary the driving-wave frequency and/or the driving-wave power based upon the detected waveguide type. The waveguide detector 4408 can be any device, set of components, software, electrical connections, or other that is/are able to identify at least one property of a waveguide 4402 connected to the device 4400.

In a further exemplary embodiment, the smart battery 3902 stores in its memory 326 a record of each time a particular device is used. This record can be useful for assessing the end of a device's useful or permitted life. For instance, once a device is used 20 times, all such batteries 3902 connected to the device will refuse to supply power thereto—because the device is defined as a "no longer reliable" surgical instrument. Reliability is determined based on a number of factors. One factor can be wear; after a certain number of uses, the parts of the device can become worn and tolerances between parts exceeded. This wear can lead to an unacceptable failure during a procedure. In some exemplary embodiments, the smart battery 3902 can recognize which parts are combined and even how many uses each part has experienced. For instance, looking at FIG. 14, if the battery 1700 is a smart battery, it can identify both the gun 1300, as well as the particular transducer assembly 1302. A memory within the smart battery 3902 can record each time the transducer assembly 1302 is operated. If each transducer assembly 1302 has an individual identifier, the smart battery 3902 can keep track of each transducer assembly's use and refuse to supply power to that transducer assembly 1302 once the gun 1300 or the transducer assembly 1302 exceeds its maximum number of uses. The TAG, stapler, vessel sealer, etc. circuitry can include a memory chip which records this information also. This way, any number of smart batteries can be used with any number of TAGs, staplers, vessel sealers, etc. and still be able to determine the total number of uses, or the total time of use (through use of clock 330), or the total number of actuations etc. of each TAG, stapler, vessel sealer etc.

Figure 40:
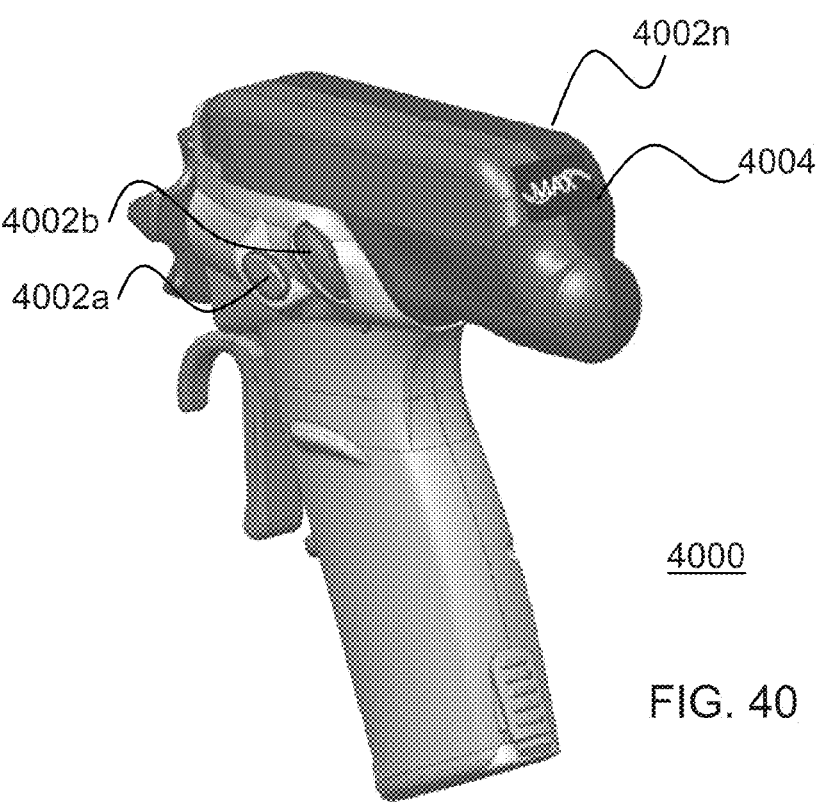
FIG. 40 is a perspective view of a left side of an ultrasonic cutting device handle with fully integrated control, drive and matching components, and transducer in a removable module, a removable battery pack, control buttons, and a display screen in accordance with an exemplary embodiment of the present invention.

Referring now to FIG. 40, another embodiment of the present invention is shown. In the embodiment of FIG. 40, the device 4000 is provided with a plurality of buttons 4002a-n, although not all can be seen in the left-side view of FIG. 40. These buttons can have various functions that pertain to operation of the device 4000. As explained above, previous devices were tethered by a cord 208 to a desktop box 202. If a prior-art device wished to add an additional function, associated with a button, then an additional communication wire would need to be added to the non-changeable strand of wires in the tether 208. The addition of wires renders the tether even less desirous, as the surgeon must work with and support the ever-increasing bundle of wires. The present invention is impervious to this disadvantage because all communication is contained within the handle itself and no external wires are needed. The device 4000 will generally operate the same and weigh the same, no matter how many buttons are added.

In accordance with yet another embodiment, the present invention is provided with a display screen 4004 that conveys visual information to an operator. The visual information can be, for instance, the number of uses a particular waveguide has been subjected to, the battery voltage, the status of the device, such as indicating a non-engaged condition of the device components, button states, warnings, and many others.

Figure 45:
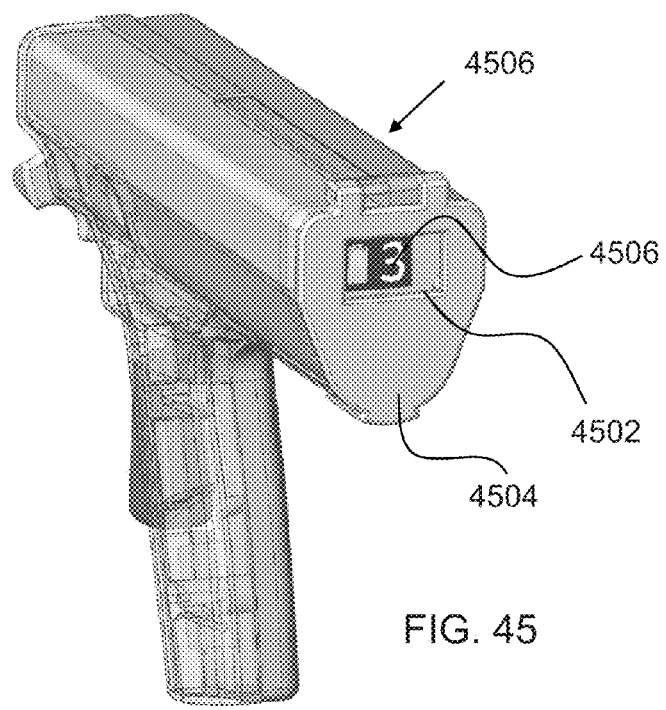
FIG. 45 is a rear perspective view of the SCUD of FIG. 22 with a display included on the waveguide-movement-generation assembly and a see-through window on the waveguide-movement-generation assembly access door allowing viewing of the display and in accordance with an exemplary embodiment of the present invention.

The present invention, according to an embodiment, as shown in FIG. 45, has a window 4502 on the compartment door 4504 that allows a user to view a display screen 4506 on a movement-generation assembly within the compartment 4508.

Figure 46:
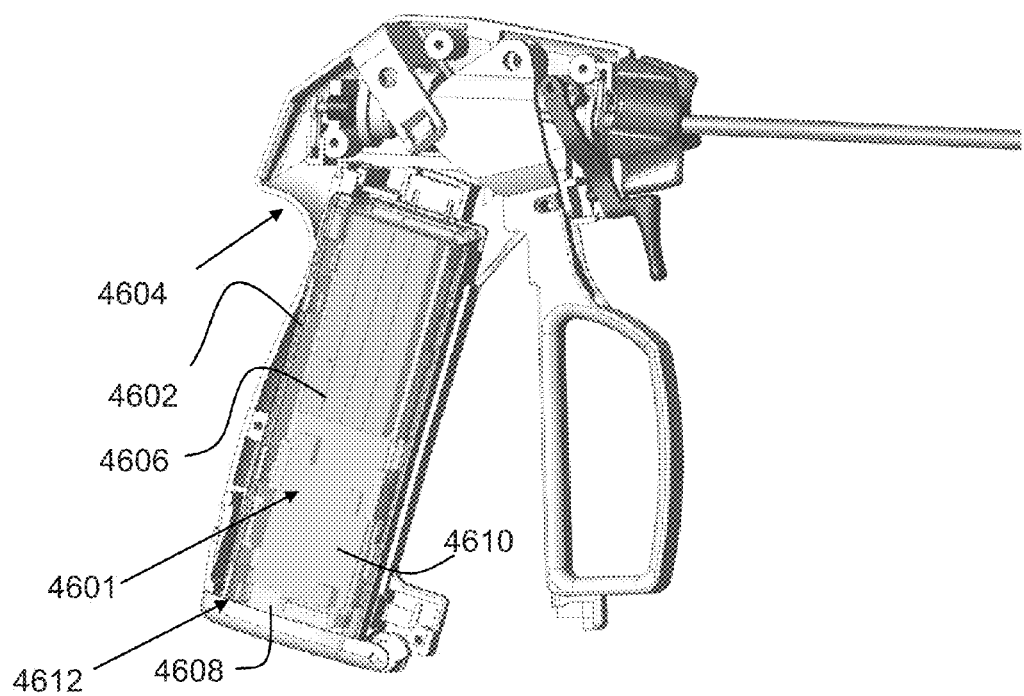
FIG. 46 is a side elevational view of an exemplary handle with the right-side shell removed to show an ultrasonic waveguide driving assembly having integrated power source, power source control circuit, and ultrasonic waveform-generating circuit in accordance with an exemplary embodiment of the present invention.

In one embodiment of the present invention, as shown in FIG. 46, the ultrasonic surgical device 4600 includes a cordless unitary housing 4602 sized to fit within a surgical instrument handle 4604. The housing 4602 houses a self-contained power source 4606 and a power source control circuit 4608 that is electrically coupled to the power source 4606 and is operable to control distribution of power from the power source 4606. The housing 4602 also holds an ultrasonic waveform-generating circuit 4610 electrically coupled to the control circuit 4608 and operable to output a waveform sufficient to drive an ultrasonic transducer of the ultrasonic surgical instrument 4600. In this embodiment, the ultrasonic waveguide driving assembly 4601 can be inserted into the inexpensive handle 4604, used for a single surgery, the handle 4604 disposed of, and the assembly can then be inserted and used in multiple other handles to perform additional surgeries. In this embodiment, all of the expensive components are reused and do not need to be aseptically sealed since they are contained within a battery-holding compartment 4612 of the handle 4604 and are never exposed to the operating environment.

Figure 47:
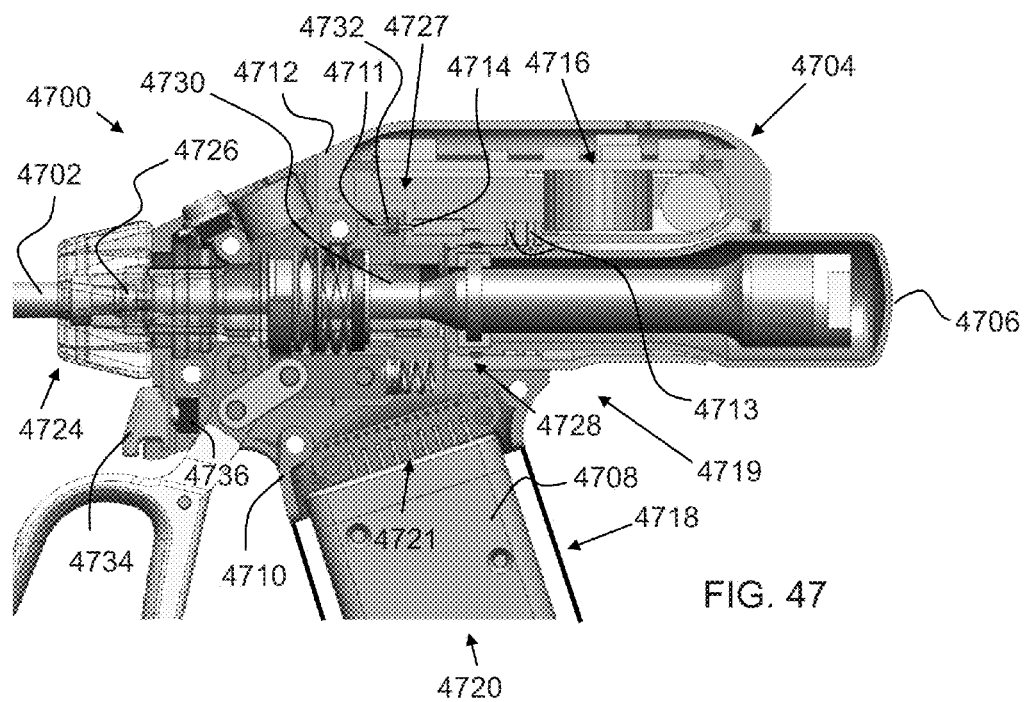
FIG. 47 is a side elevational view of an exemplary ultrasonic surgical assembly with the left-side shell removed to show a separately insertable and rotatable transducer with an exposed portion in accordance with an exemplary embodiment of the present invention.

FIG. 47 shows yet another embodiment of the present invention where, in this case, the transducer remains separate from the ultrasonic-signal-generator assembly, which allows it to be grasped when the waveguide is being attached to the transducer. The inventive ultrasonic surgical assembly 4700 includes an ultrasonic waveguide 4702, an ultrasonic-signal-generator assembly 4704, an ultrasonic transducer 4706, a removable battery 4708, and a surgical handle 4710.

The ultrasonic-signal-generator assembly 4704 includes a shell 4712, a selectively removable securing connector 4714 on the shell 4712, an ultrasonic-driving-wave-signal generating circuit 4716 housed within the shell 4712, power contacts 4711 electrically coupling the ultrasonic-driving-wave-signal generating circuit 4716 to the battery 4708, and output contacts 4713 supplying an ultrasonic driving wave produced by the ultrasonic-driving-wave-signal generating circuit 4716 when in operation.

The surgical handle 4710 includes a first handle body portion 4718 and an attached second hand body portion 4719. The first handle body portion 4718 defines therein an aseptically sealable battery-holding compartment 4720 that is selectively exposed to the environment and is able to aseptically removably hold therein the removable battery 4708. Contacts 4721 within the compartment 4720 electrically connect the battery 4708 therein to the ultrasonic-signal-generator assembly 4704.

The second handle body portion 4719 has a waveguide attachment dock 4724, which is exposed to the environment and has a first couple 4726 operable to selectively removably rotatably secure the ultrasonic waveguide 4702 to the second handle body portion 4719. The second handle body portion 4719 also has a transducer attachment dock 4728 which opposes the waveguide attachment dock 4724. The transducer attachment dock 4728 is exposed to the environment and has a second couple 4730 operable to selectively removably rotatably secure the ultrasonic transducer 4706 to the second handle body portion 4719 and to the ultrasonic waveguide 4702 when the ultrasonic waveguide 4702 is coupled to the waveguide attachment dock 4724. The couples 4726 and 4730 can simply be aligned passageways that place the waveguide 4702 into axial alignment with the transducer 4706. Of course, the couples 4706 and 4730 can provide more structure, such as threads, that actually hold the waveguide 4702 and/or transducer 4706 to the handle or to each other.

Additionally, the second handle body portion 4719 has an ultrasonic-signal-generator assembly dock 4727 that is exposed to the environment and shaped to removably secure the securing connector 4714 of the ultrasonic-driving-wave-signal generating circuit 4716 to the second handle body portion 4719. The assembly dock 4727 also aligns the ultrasonic-driving-wave-signal generating circuit 4716 so that, when the circuit 4716 and the transducer 4706 are connected to the second handle body portion 4719, the ultrasonic-driving-wave-signal generating circuit 4716 and the transducer 4706 are electrically connected.

Advantageously, the ultrasonic transducer 4706 is rotatable with respect to the second handle body portion 4719 and the waveguide attachment dock 4724 is shaped to rotatably connect the ultrasonic waveguide 4702 in the waveguide attachment dock 4724 to the ultrasonic transducer 4706 in the transducer attachment dock 4728 through the second handle body portion 4719. In this way, the waveguide attachment dock 4724 and the transducer attachment dock 4728 directly physically couple the ultrasonic waveguide 4702 and the ultrasonic transducer 4706 and permit a corresponding rotation of the ultrasonic transducer 4706 with respect to the second handle body portion 4719 when at least one of the ultrasonic waveguide 4702 and the ultrasonic transducer 4706 rotates.

Although not shown in the view of FIG. 47 (but shown in FIGS. 39 and 46), the battery compartment 4720 has a compartment door 3914 that is connected movably to the second handle body portion 4719 and has an open position permitting entry and removal of the removable battery 4708 respectively into and from the compartment 4720 and a closed position aseptically sealing the compartment 4720 from the environment. A set of conductive power leads 4721 in the battery-holding compartment 4720 are shaped to electrically connect the battery 4708 to the ultrasonic-signal-generator assembly 4704 at least when the battery 4708 is sealed in the battery-holding compartment 4720.

In a further exemplary embodiment, the assembly 4700 includes a memory 4732 electrically connected at least to the ultrasonic-signal-generator assembly dock 4727. The memory 4732 stores a record of each time the device is used. This record can be useful for assessing the end of the device's useful or permitted life. For instance, once the device is used twenty (20) times, the device can be programmed to no longer function (e.g., because the device is, then, a "no longer reliable" surgical instrument). The memory 4732 can also store a number of uses of the device's peripherals. For example, after a certain number of uses, the parts of the device can become worn and tolerances between parts exceeded. This wear can lead to an unacceptable failure during a procedure. In some exemplary embodiments, the memory 4732 stores a record of the parts that have been combined with the device and how many uses each part has experienced.

In some embodiments, as explained above, the memory 4732 is on the battery and the handle body is provided with a device identifier that is communicatively coupled to the battery-holding compartment and is operable to communicate to the smart battery at least one piece of information about the ultrasonic surgical assembly 4700, such as the use history discussed in the preceding paragraph, a surgical handle identifier, a history of previous use, and/or a waveguide identifier.

Figure 48:
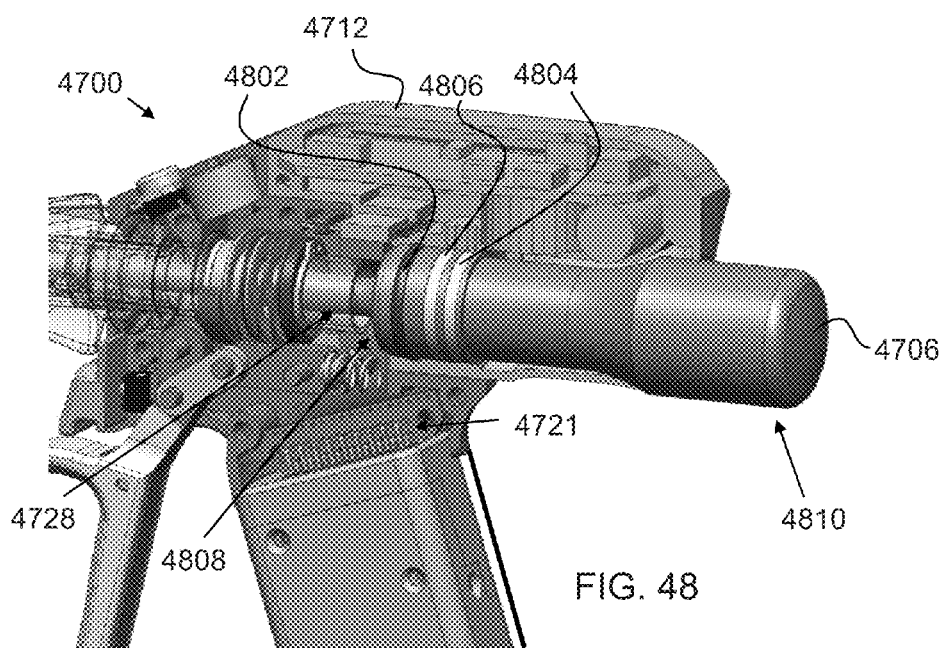
FIG. 48 is a perspective view of the ultrasonic surgical assembly of FIG. 47.

The perspective view of the assembly 4700 in FIG. 48 shows an O-ring 4802 around the transducer 4706. The O-ring 4802 helps protect and seal the interior of the device 4700 from liquids that enter around the shell 4712. Once the transducer 4706 is inserted into the transducer attachment dock 4728, the O-ring 4802 also holds the transducer 4706 in place. FIG. 48 further shows a view of a pair of transducer input contacts 4804, 4806 that electrically couple to the connectors 4713 to provide the driving signal to the transducer 4706.

Figure 49:
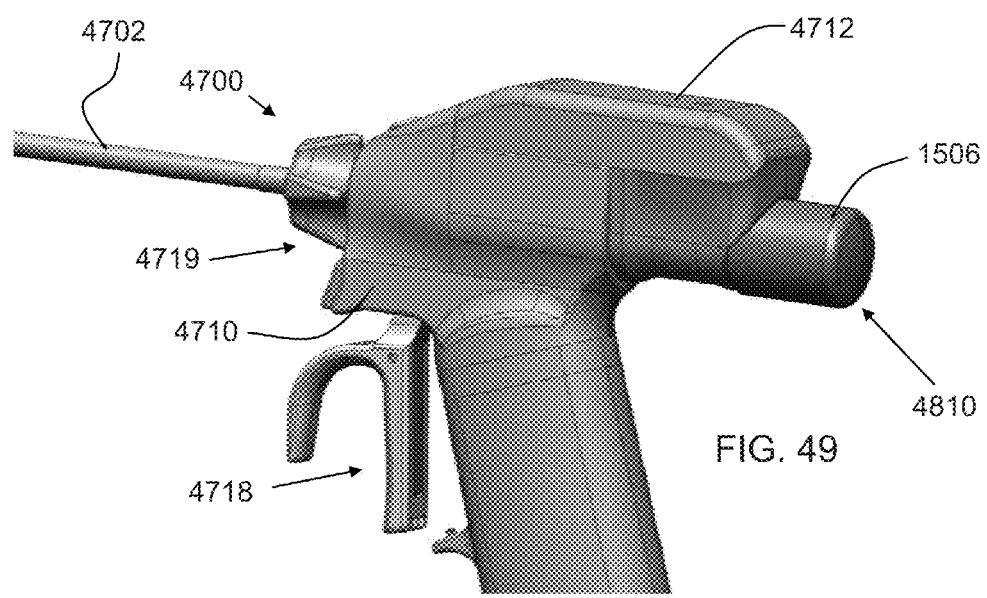
FIG. 49 is a perspective view of the fully assembled ultrasonic surgical assembly of FIGS. 47 and 48.

FIG. 49 is a perspective view of the inventive ultrasonic surgical assembly 4700 fully assembled. The ultrasonic-signal-generator shell 4712 covers and obscures the details of the ultrasonic-signal-generator assembly 4704, the transducer housing 1506 obscures the details of the transducer 1606, and the handle body 4710 obscures the interior elements of the handle portions 4718, 4719.

Figure 50:
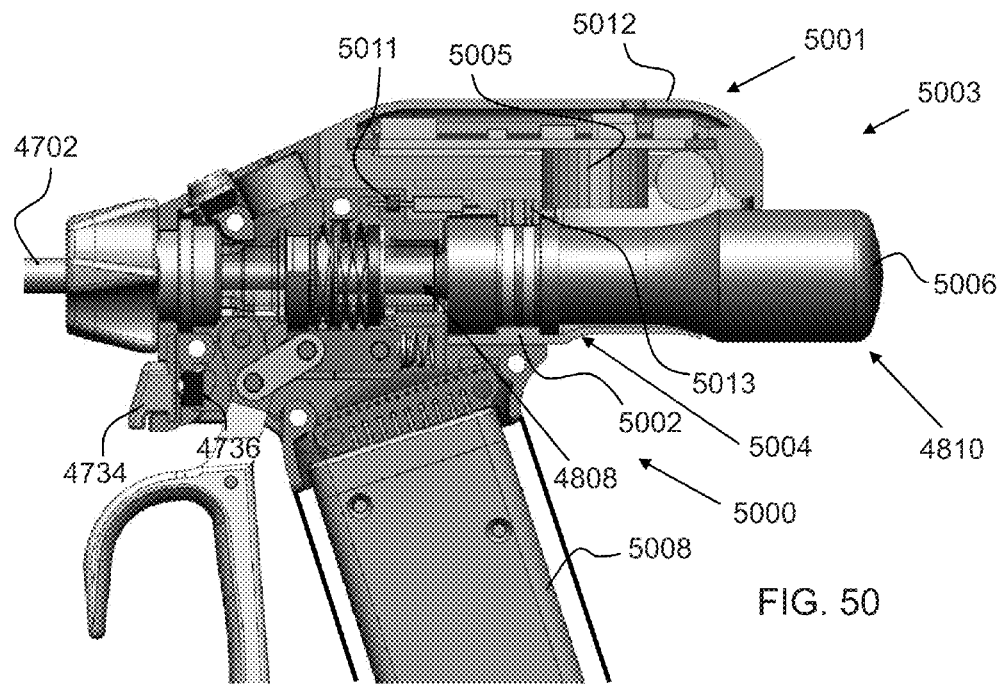
FIG. 50 is a side elevational view of an exemplary ultrasonic surgical assembly with the left-side shell removed to show a rotatable transducer with an exposed portion in accordance with an exemplary embodiment of the present invention.

FIG. 50 shows an elevational view of a variation of the ultrasonic surgical assembly shown in FIGS. 47 and 48. The ultrasonic-signal-generator assembly 5001 includes a shell 5012, an ultrasonic-driving-wave-signal generating circuit 5005 housed within the shell 5012, power contacts 5011 electrically coupling the ultrasonic-driving-wave-signal generating circuit 5005 to the battery 5008, and output contacts 5013 supplying an ultrasonic driving wave produced by the ultrasonic-driving-wave-signal generating circuit 5005 when in operation.

In the embodiment of FIG. 50, the transducer 5006 is provided with an annular channel 5004 that aligns with a wall 5002 on the interior of the ultrasonic-signal-generator shell 5012. The transducer channel 5004 and the wall 5002 prevent the transducer 5006 from moving laterally with respect to the ultrasonic-driving-wave-signal generating circuit 5005 (and longitudinally with respect to the waveguide 4702), while continuing to allow the transducer 5006 to rotate within the ultrasonic-signal-generator assembly 5001. In this embodiment, the transducer 5006 and the ultrasonic-signal-generator assembly 5001, similar to the embodiments of FIGS. 23 to 30, 39, 40, and 42 to 44, create a single, removable ultrasonic-movement generation assembly 5003, except that, in this embodiment, the transducer 5006 can be grasped, at an exposed proximal end 4810, by the user's hands during attachment and detachment to the waveguide 4702 and during use of the device to position the end effector 2504 (not shown in this view) of the waveguide 4702.

FIGS. 47 to 50 also show a button 4734 that places the ultrasonic surgical assembly 4700 into an ultrasonic operating mode, which causes ultrasonic motion at the waveguide 2504. More specifically, depression of the button 4734 causes electrical contacts within a switch 4736 to close, thereby completing a circuit between the battery 4708 and the ultrasonic-driving-wave-signal generating circuit 4716 so that electrical power is applied to the transducer 4706. Of course, the description of closing electrical contacts in a circuit is, here, merely an exemplary statement of switch operation. There are many alternative embodiments that can include opening contacts or processor-controlled power delivery that receives information from the switch 4736 and directs a corresponding circuit reaction based on the information.

Figure 53:
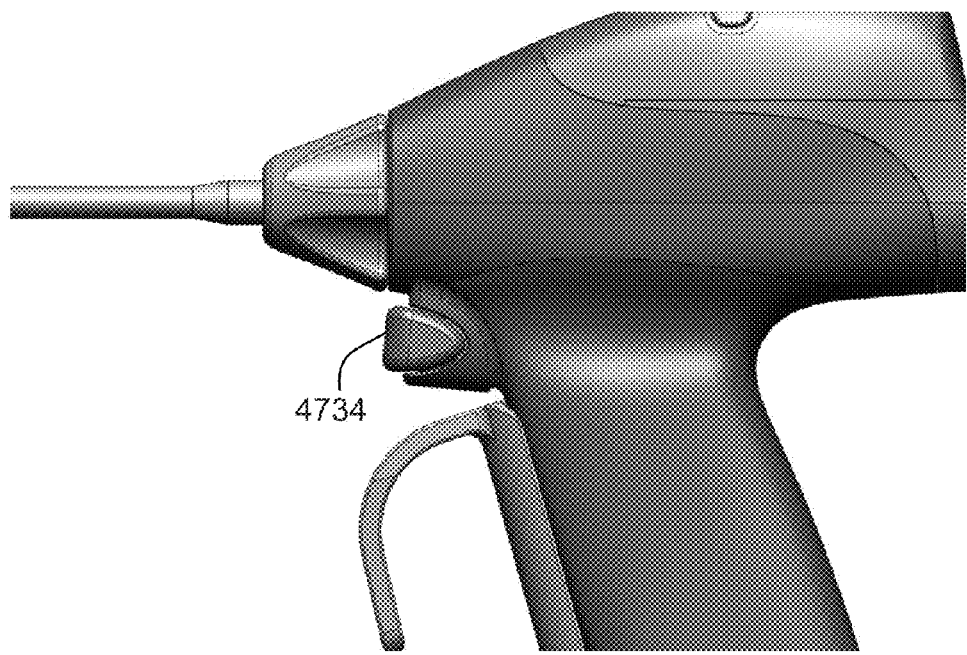
FIG. 53 is a fragmentary, left side elevational view of an exemplary ultrasonic surgical assembly with a functional two-stage button and switch in accordance with an exemplary embodiment of the present invention.
Figure 54:
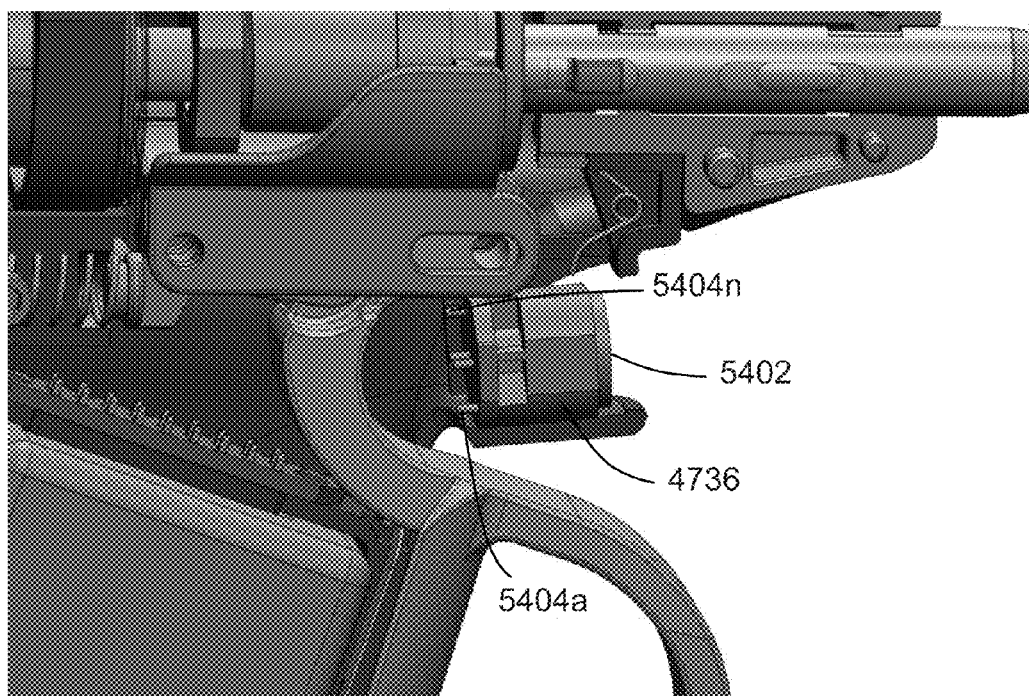
FIG. 54 is a fragmentary, perspective view of the exemplary ultrasonic surgical assembly of FIG. 53 from the right side with the right-side shell removed to show the two-stage switch according to an exemplary embodiment of the present invention.

FIG. 53 shows the button 4734 from a side elevational view and FIG. 54 provides a cutaway perspective view of the interior of the handle body 4710, revealing a more detailed view of the switch 4736. In a first embodiment, depression of a plunger 5402 of the switch 4736 activates the switch and initiates a switch state change. In this embodiment, the switch 4736 is provided with a plurality of contacts 5404*a-n*. Depression of the plunger 5402 results in the state change of the switch 4736 and a corresponding change of position or contact between two or more of the plurality of contacts 5404*a-n*. If a circuit is connected through the switch 4736, i.e., the switch 4736 controls power delivery to the transducer 4706, the state change will either complete or break the circuit, depending on the operation mode of the switch 4736.

Figure 55:
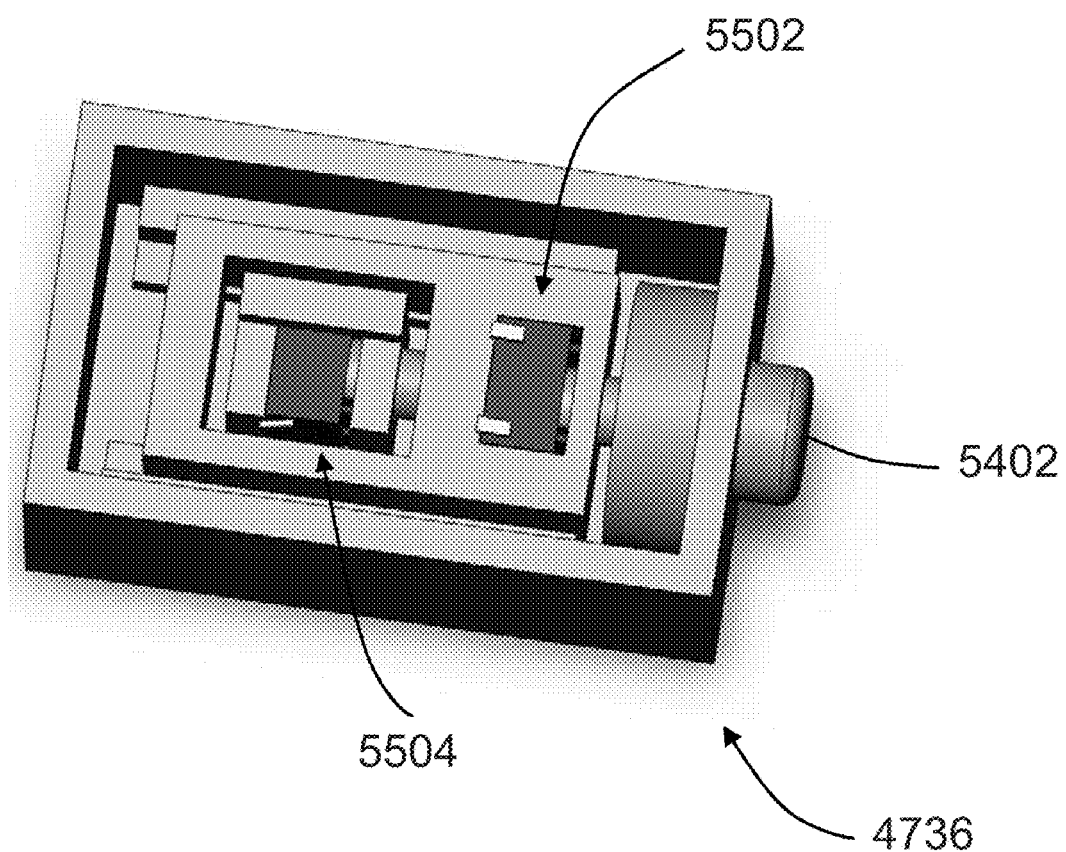
FIG. 55 is a perspective view of a two-stage switch with its cover removed exposing two sub-switches according to an exemplary embodiment of the present invention.

FIG. 55 shows an exemplary embodiment of the switch 4736 that provides two switching stages. The switch 4736 includes two sub-switches 5502 and 5504. The sub-switches 5502 and 5504 advantageously provide two levels of switching within a single button 5402. When the user depresses the plunger 5402 to a first distance, the first sub-switch 5502 is activated, thereby providing a first switch output on the contacts 5404*a-n* (not shown in this view). When the plunger 5402 is depressed further, the second sub-switch is activated, resulting in a different output on the contacts 5404*a-n*. An example of this two-stage switch 4736 in actual use would be for the ultrasonic-driving-wave-signal generating circuit 4716 to have two possible output power levels available that result in two different motion displacement values of the waveguide 2504. Activation of the first sub-switch 5502 can initiate the first output power level from the ultrasonic-driving-wave-signal generating circuit 4716 and activation of the second sub-switch could result in a second power level, most likely higher, to be output from the ultrasonic-driving-wave-signal generating circuit 4716. The sub-switches 5502 and 5504 being configured in a stack, shown in FIG. 55, advantageously make it easy and intuitive for an operator to move from the first switch mode, i.e., first power level, to the second switch mode, i.e., second power level, by simply squeezing the plunger 5402 of the button 4734 with increased force.

In one embodiment of the sub-switches 5502 and 5504, spring force could be utilized, with each spring having a different spring-force rating. When the plunger 5402 is initially depressed, the first spring in the first sub-switch 5502 begins to compress. Because a second spring located in the second sub-switch 5504 is stiffer than the first spring, only the first sub-switch 5502 is caused to change switching states. Once the first sub-switch 5502 is depressed a sufficient distance to change switching states, further (greater) force applied to the plunger 5402 causes the second stiffer spring to depress and for the second sub-switch 5504 to change states.

In practice, ultrasonic cutting devices, such as ones employing the present invention, encounter a variety of tissue types and sizes and are used in a variety of surgical procedure types, varying from precise movements that must be tightly controlled to non-delicate cutting material that requires less care. It is therefore advantageous to provide two ultrasonic cutting power levels that allow an operator to select between a low-power cutting mode and a higher-power cutting mode. For example, in the low-power cutting mode, i.e., only the first sub-switch 5502 is depressed, causing the tip of the waveguide 2504 to move at about 0.002 inches of displacement. In the higher-power cutting mode, i.e., both the first and second sub-switches 5502 and 5504 (or just 5504) are depressed, causing the tip of the waveguide 2504 to move at about 0.003 inches of displacement, providing a more robust cutting tool that can move through tissue at a quicker rate or cut though tougher, more dense, matter more rapidly than the lower-power setting. For example, cutting through mesentery is generally performed at a more rapid rate at higher power, whereas vessel sealing can be performed at lower power and for a longer period of time.

The present invention, however, is in no way limited to stacked switches and can also include switches that are independent of each other. For instance, the shape of the button 4734 may have a first portion that makes contact with a first low-power switch and a second portion that, upon further movement of the button, makes contact with a second high-power switch. The present invention includes any multiple-stage switch that engages different stages by movement of a single button.

In one embodiment of the present invention, the switch 4736 provides a physical resistance analogous to a compound bow. Compound bows, which are well known for shooting arrows at a high rate of speed, have a draw-force curve which rises to a peak force and then lets off to a lower holding force. By recreating this physical effect with the second sub-switch 5504, the user of the device will find moving into and engaging the first sub-switch 5502 to be rather easy, while moving into the higher-power mode, initiated by depression of the second sub-switch 5504 requiring a higher depression force, to be an occurrence that takes place only by the operator consciously applying an increased force. Once the higher depression force is overcome, however, the force required to hold the second sub-switch 5504 in the depressed position decreases, allowing the operator to remain in the higher-power mode, i.e., keeping the button depressed, without fatiguing the operator's finger. This compound-bow-type effect can be accomplished in a variety of ways. Examples include an offset cam, overcoming a pin force or other blocking object, software control, and many others.

In one embodiment of the present invention, the switch 4736 produces an audible sound when the switch 4736 moves from the first mode to the second higher-power mode. The sound notifies the operator of entry into the higher-power mode. The notification can advantageously prevent unintended operation of the inventive ultrasonic device.

Furthermore, the inventive two-stage button allows an operator complete control of any surgical task without requiring the operator to focus their visual attention on the instrument itself. In other words, the operator does not have to look to ensure (s)he is preparing to push the proper button, as only one button is used.

Figure 51:
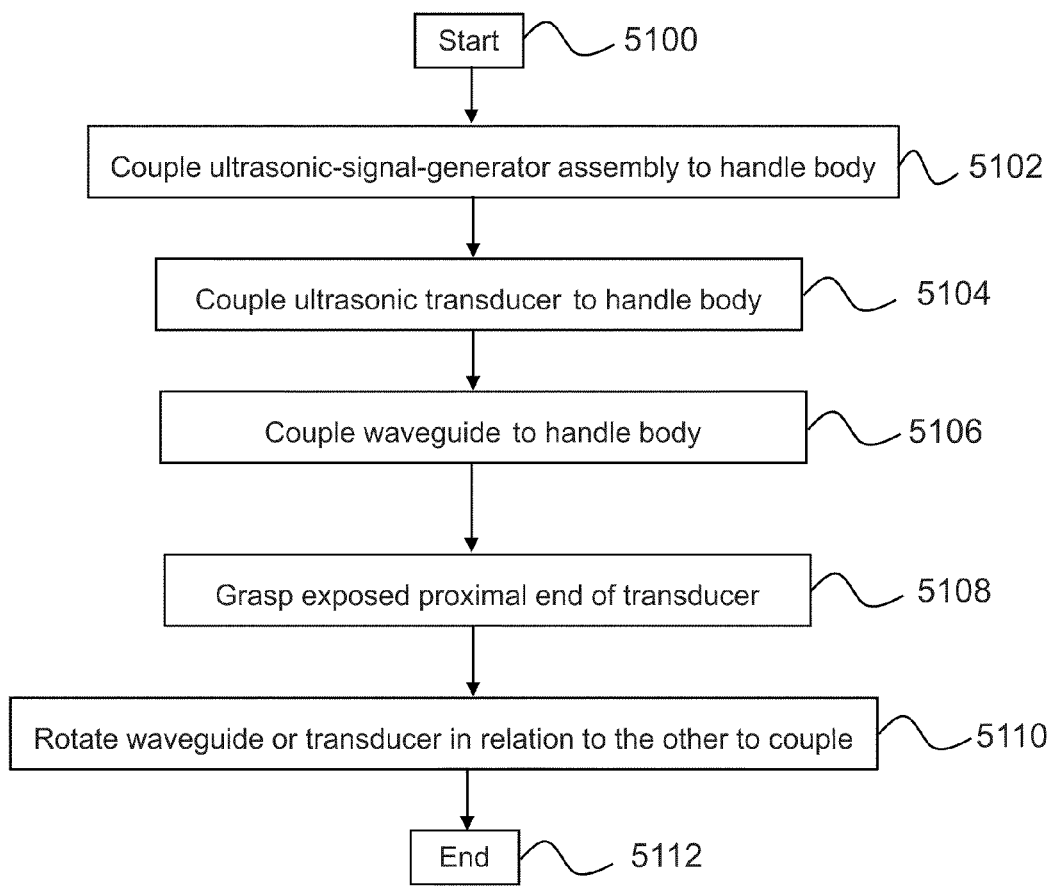
FIG. 51 is a process flow diagram showing a method for assembling an ultrasonic surgical assembly with a separate ultrasonic-signal-generation assembly and transducer in accordance with an exemplary embodiment of the present invention.

FIG. 51 is a process flow diagram illustrating exemplary steps for use of the present invention. The process begins at step 5100 and moves directly to step 5102 where an ultrasonic surgical assembly 4700 is assembled by first coupling an ultrasonic-signal-generator assembly 4704 to a handle body 4710. In step 5104, an ultrasonic transducer 4706 is coupled to the handle body 4710 by inserting it below or through the ultrasonic-signal-generator assembly 4704 so that its ultrasonic-movement-producing distal end 4808 (shown in FIG. 48) is inserted into the transducer attachment dock 4728. In step 5106, a waveguide 4702 is coupled to the handle body 4710 by inserting the waveguide 4702 into the waveguide attachment dock 4724. It should be noted that the steps 5102-5106 do not have to be in the sequence just presented and can be in any order without affecting the present invention.

In step 5108, a user grasps the proximal end 4810 of the ultrasonic transducer 4706. As shown in FIG. 49, grasping the proximal end 4810 of the ultrasonic transducer 4706 is simple, because the proximal end 4810 extends beyond the ultrasonic-signal-generator shell 4712 that shields the ultrasonic-signal-generator assembly 4704. Next, in step 5110, either the waveguide 4702 or the ultrasonic transducer 4706 is rotated with respect to the other to fixedly couple the waveguide 4702 to the ultrasonic-movement-producing distal end of the transducer 4706. The coupling is accomplished, for example, through the distal threaded end 1610 of the transducer, as shown in FIG. 16, and a non-illustrated opposing set of threads in the proximal end of the waveguide 4702. Once coupled, both the ultrasonic transducer 4706 and the waveguide 4702 rotate in relation to the handle body 4710 and the ultrasonic-signal-generator assembly 4704.

Because the ultrasonic transducer 4706 is completely separable from the ultrasonic-signal-generator assembly 4704, in an additional optional step, any of the components can be individually removed and replaced. For instance, the ultrasonic transducer 4706 can be removed from the waveguide 4702 and the handle body 4710 and a replacement ultrasonic transducer 4706 can be attached to the waveguide 4702 and handle body 4710. The process ends at step 5112.

Figure 52:
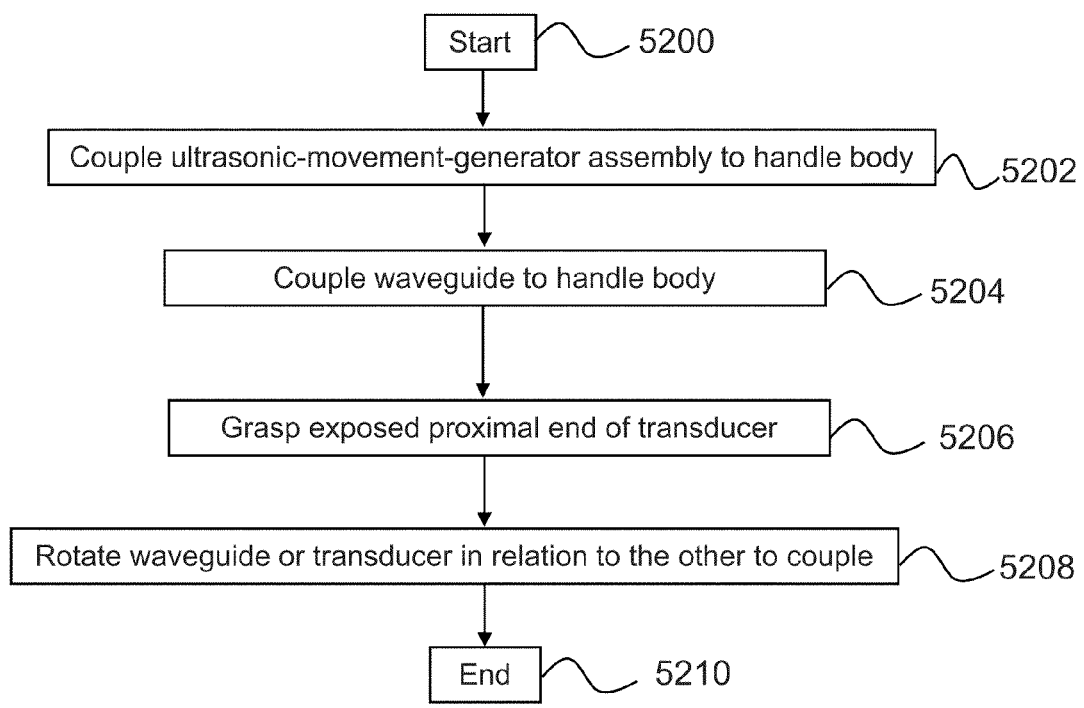
FIG. 52 is a process flow diagram showing a method for assembling an ultrasonic surgical assembly with an ultrasonic-movement-generation assembly that includes an ultrasonic-signal-generation assembly and a transducer in accordance with an exemplary embodiment of the present invention.

FIG. 52 shows a process flow diagram that pertains to the embodiment of the ultrasonic surgical assembly 5000 shown in FIG. 50. As explained above, the difference between the ultrasonic surgical assembly 4700 of FIGS. 47 to 49 and the ultrasonic surgical assembly 5001 of FIG. 50 is that, in the embodiment of FIG. 50, the ultrasonic transducer 5006 is part of the ultrasonic-movement-generation assembly 5001. Therefore, the process flow diagram of FIG. 52 shares several steps with the process flow diagram of FIG. 51. The process begins at step 5200 and moves directly to step 5202 where the ultrasonic-movement-generator assembly 5001, which includes both the ultrasonic-signal-generation assembly 5001 and the ultrasonic transducer 5006, is coupled to the handle body 4710. In step 5204, the waveguide 4702 is coupled to the handle body 4710 by inserting the waveguide 4702 into the waveguide attachment dock 4724. It should be noted that the steps 5202 and 5204 do not have to be in the sequence just presented and can be in any order without affecting the present invention.

In step 5206, a user grasps the proximal end 4810 of the ultrasonic transducer 5006. Once assembled, the embodiment of FIG. 50 is similar to the embodiment shown in FIG. 49. Grasping the proximal end 4810 of the ultrasonic transducer 5006 is simple, because the proximal end 4810 extends beyond the ultrasonic-signal-generator shell 5012 that shields the ultrasonic-signal-generator assembly 5001. Next, in step 5208, either the waveguide 4702 or the ultrasonic transducer 5006 is rotated with respect to the other to fixedly couple the waveguide 4702 to the ultrasonic-movement-producing distal end of the transducer 5006. Once coupled, both the ultrasonic transducer 5006 and the waveguide 4702 rotate in relation to the handle body 4710 and the ultrasonic-signal-generator assembly 5001. The process ends at step 5210.

As has been described, the present invention provides a small and efficient hand-held ultrasonic cutting device that is self-powered and, therefore, cordless. Alternatively, and/or additionally, the invention has a separate body-worn pack that houses any combination of the control electronics and the self-contained power supply. In either embodiment, the expensive set-top box is eliminated entirely. The invention provides low-voltage or battery-voltage switching or waveforming stages prior to the transducer. Advantageously, the device allows a user to operate completely free of cords or other tethering devices. The present invention, by "marrying" all of the frequency sensitive components within one place (e.g., the handle), also eliminates any inductive losses that occur between prior art set-top boxes and handpieces—a disadvantage suffered by all prior-art ultrasonic cautery/cutting devices. Because of the close coupling between the drive circuit 308 and the matching network 312, the overall power modification circuit is tolerant of higher Q factors and larger frequency ranges.

The present invention provides additional advantages in the way the device is kept sterile. Because the inventive device is a fraction of a size of the prior art devices, the driving circuit can be placed within the handle. The handle, transducer, waveguide, and blade are sterilized and the handle has a door that opens, allowing the battery and driving circuits, which are outside the sterile field, to be dropped inside the handle. When the door is closed, the non-sterile portions are sealed within the handle.

Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments, and it is intended that the appended claims cover any and all such applications, modifications, and embodiments within the scope of the present invention.

What is claimed is:

1. A method for operating a surgical device, comprising: providing
    a control circuit operable to carry out at least two operational conditions of the surgical device; and
    effecting the at least two operational conditions with a two-stage switch electrically connected to the control circuit, a first stage of the switch effecting a first of the at least two operational conditions and a second stage of the switch effecting a second of the at least two operational conditions different from the first operational condition, the two-stage switch having a variable resistance such that:
        the first stage occurs when a first depression force is applied to the switch;
        the second stage occurs when a second depression force greater than the first depression force is applied to the switch; and
        a holding force lower than at least the second depression force is required to maintain the switch in the second stage.

2. The method according to claim 1, which further comprises:
    providing a handle of the surgical device with a self-contained power supply; and
    controlling an amount of power delivered from the power supply with the control circuit.

3. The method according to claim 2, wherein the first operational condition is a first amount of power delivered from the power supply and the second operational condition is a second amount of power delivered from the power supply.

4. The method according to claim 2, which further comprises delivering a first amount of power from the power supply in the first operational condition and delivering a second amount of power different from the first amount from the power supply in the second operational condition.

5. The method according to claim 4, wherein the first amount of power is less than the second amount.

6. The method according to claim 1, which further comprises:
effecting the first and second operational conditions using at least one electrical contact of the two-stage switch to electrically close the control circuit.

7. The method according to claim 1, which further comprises:
effecting the first and second operational conditions using at least one electrical contact of the two-stage switch to electrically break the control circuit.

8. The method according to claim 1, which further comprises:
switching between the first and second stages by changing a position of the two-stage switch.

9. The method according to claim 1, wherein the two-stage switch is in the first stage when placed in a first position by applying the first depression force.

10. The method according to claim 9, wherein the two-stage switch is in the second stage when placed in a second position by applying the second depression force.

11. The method according to claim 10, wherein the first and second positions are operably connected in a stacked configuration.

12. The method according to claim 1, which further comprises: switching to the first stage by applying the first depression force to partially depress the two-stage switch.

13. The method according to claim 12, which further comprises: switching to the second stage by applying the second depression force to fully depress the two-stage switch.

14. The method according to claim 8, which further comprises:
coupling a plunger to the two-stage switch; and
changing the position of the two-stage switch by applying pressure to the plunger.

15. The method according to claim 14, wherein the plunger is spring-biased.

16. The method according to claim 14, which further comprises:
applying a variable amount of pressure to the plunger to cause the two-stage switch to change position.

17. The method according to claim 16, wherein an amount of pressure needed to position the two-stage switch in the first stage is less than the amount of pressure needed to position the two-stage switch in the second stage.

18. The method according to claim 1, wherein the two-stage switch is comprised of at least a first sub-switch and a second sub-switch, the first sub-switch effecting the first stage and the second sub-switch effecting the second stage.

* * * * *